(12) United States Patent
Mastrangelo et al.

(10) Patent No.: US 11,899,004 B2
(45) Date of Patent: Feb. 13, 2024

(54) SYSTEMS AND METHODS FOR MONITORING OCEAN-BASED CARBON DIOXIDE REMOVAL DEVICES AND ACCUMULATION OF A TARGET PRODUCT

(71) Applicant: Running Tide Technologies, Inc., Portland, ME (US)

(72) Inventors: Luca Mastrangelo, Scarborough, ME (US); William Johnson, Marion, MA (US); Josh Hill, Marion, MA (US); Timothy J. Dyson, South Berwick, ME (US); Jacob F. Hagler, Portland, ME (US); Charles B. W. Halvorson, Portland, ME (US); Philipp Max Werminghausen, Boston, MA (US); Andrew Clyde Thompson, Biddeford, ME (US)

(73) Assignee: Running Tide Technologies, Inc., Portland, ME (US)

( * ) Notice: Subject to any disclaimer, the term of this patent is extended or adjusted under 35 U.S.C. 154(b) by 0 days.

(21) Appl. No.: 18/156,615

(22) Filed: Jan. 19, 2023

(65) Prior Publication Data

US 2023/0152292 A1 May 18, 2023

Related U.S. Application Data

(63) Continuation of application No. PCT/US2022/079746, filed on Nov. 11, 2022.
(Continued)

(51) Int. Cl.
*G01N 33/18* (2006.01)
*G01N 21/64* (2006.01)
(Continued)

(52) U.S. Cl.
CPC ......... *G01N 33/1826* (2013.01); *B63B 22/20* (2013.01); *B63B 35/00* (2013.01);
(Continued)

(58) Field of Classification Search
USPC ......................................................... 73/61.51
See application file for complete search history.

(56) References Cited

U.S. PATENT DOCUMENTS 4,051,810 A 10/1977 Breit
4,133,141 A 1/1979 Lee
(Continued)

FOREIGN PATENT DOCUMENTS

CA 2804792 A1 1/2012
CN 1208552 A 2/1999
(Continued)

OTHER PUBLICATIONS

International Search Report and Written Opinion in PCT/US2022/079746, dated Mar. 21, 2023, 13 pages.
(Continued)

*Primary Examiner* — Clayton E. LaBalle
*Assistant Examiner* — Warren K Fenwick
(74) *Attorney, Agent, or Firm* — Cooley LLP

(57) ABSTRACT

An apparatus includes a first member having a housing that encloses a power source and a controller, a second member coupled to the first member that is seeded with a target product, and a sensing module coupled to the first member to allow power from the power source to be transmitted to the sensing module and sensor data from the sensing module to be transmitted to the controller. The sensing module including a sensor oriented toward at least a portion of the second member. The sensor configured to obtain sensor data associated with at least one characteristic of the target product.

10 Claims, 30 Drawing Sheets

Related U.S. Application Data

(60) Provisional application No. 63/278,243, filed on Nov. 11, 2021.

(51) Int. Cl.
- *B63B 22/20* (2006.01)
- *B63B 79/15* (2020.01)
- *B63B 35/00* (2020.01)
- *H04N 23/50* (2023.01)

(52) U.S. Cl.
CPC .......... *B63B 79/15* (2020.01); *G01N 21/645* (2013.01); *H04N 23/50* (2023.01)

(56) References Cited

U.S. PATENT DOCUMENTS

| | | | |
|---|---|---|---|
| 4,235,043 A | 11/1980 | Harasawa et al. | |
| 4,395,970 A | 8/1983 | Kunkle et al. | |
| 5,309,672 A | 5/1994 | Spencer et al. | |
| 5,846,423 A | 12/1998 | Jensen | |
| 6,056,919 A | 5/2000 | Markels, Jr. | |
| 6,062,170 A | 5/2000 | Finch et al. | |
| 6,230,646 B1 | 5/2001 | Berry et al. | |
| 6,244,218 B1 | 6/2001 | McNeil | |
| 6,343,567 B1 | 2/2002 | McNeil et al. | |
| 6,539,894 B1 | 4/2003 | Byrne et al. | |
| 6,892,672 B2 | 5/2005 | Klein | |
| 7,690,247 B1* | 4/2010 | Lapota | G01C 13/00 73/61.51 |
| 7,722,842 B2 | 5/2010 | Park et al. | |
| 7,836,633 B2 | 11/2010 | Wilcox | |
| 7,905,055 B2 | 3/2011 | Wilcox | |
| 8,114,374 B2 | 2/2012 | Blencoe et al. | |
| 11,382,315 B2 | 7/2022 | Merrill et al. | |
| 2002/0162515 A1 | 11/2002 | Boyd | |
| 2004/0158478 A1 | 8/2004 | Zimmerman | |
| 2006/0162667 A1 | 7/2006 | Papadoyianis et al. | |
| 2007/0209278 A1 | 9/2007 | Becker | |
| 2009/0118859 A1 | 5/2009 | Whaley et al. | |
| 2009/0151240 A1 | 6/2009 | Kayama et al. | |
| 2009/0210295 A1 | 8/2009 | Edholm et al. | |
| 2010/0154298 A1 | 6/2010 | Albus et al. | |
| 2011/0289840 A1 | 12/2011 | Bakken | |
| 2012/0011050 A1 | 1/2012 | Lambert | |
| 2012/0199078 A1 | 8/2012 | Krone et al. | |
| 2015/0020445 A1 | 1/2015 | Grajcar | |
| 2015/0173317 A1 | 6/2015 | Ordway et al. | |
| 2015/0196002 A1* | 7/2015 | Friesth | A01G 7/045 315/297 |
| 2016/0029579 A1* | 2/2016 | Carscallen | A01G 9/249 47/62 R |
| 2016/0121009 A1 | 5/2016 | Farr et al. | |
| 2016/0319395 A1 | 11/2016 | Bu et al. | |
| 2018/0116139 A1 | 5/2018 | Karta | |
| 2018/0170486 A1 | 6/2018 | Sinclair et al. | |
| 2019/0141925 A1 | 5/2019 | Le Berre | |
| 2019/0377946 A1 | 12/2019 | Genty et al. | |
| 2020/0338497 A1 | 10/2020 | McDaniel | |
| 2021/0112786 A1 | 4/2021 | Fries et al. | |
| 2021/0177998 A1 | 6/2021 | Brown et al. | |
| 2021/0267214 A1 | 9/2021 | Farmer et al. | |
| 2021/0345589 A1* | 11/2021 | Merrill | A01G 33/00 |
| 2022/0295761 A1* | 9/2022 | Merrill | A01K 61/70 |
| 2023/0106744 A1* | 4/2023 | Chalfin | G06Q 10/00 423/220 |

FOREIGN PATENT DOCUMENTS

| | | | |
|---|---|---|---|
| CN | 204168860 U | | 2/2015 |
| CN | 204350803 U | | 5/2015 |
| CN | 204350804 U | * | 5/2015 |
| CN | 204350809 U | | 5/2015 |
| CN | 204350864 U | | 5/2015 |
| CN | 204634737 U | | 9/2015 |
| CN | 204634741 U | | 9/2015 |
| CN | 104996327 A | | 10/2015 |
| CN | 104996347 A | | 10/2015 |
| CN | 105028250 A | * | 11/2015 |
| CN | 105028250 A | | 11/2015 |
| CN | 104082120 B | | 1/2016 |
| CN | 108147544 A | | 6/2018 |
| JP | H0965795 A | | 3/1997 |
| JP | 2002119161 A | | 4/2002 |
| JP | 2005348696 A | | 12/2005 |
| JP | 2006288207 A | | 10/2006 |
| JP | 2008061509 A | | 3/2008 |
| JP | 2008148575 A | | 7/2008 |
| RU | 126327 U1 | | 3/2013 |
| WO | WO-2006030042 A1 | | 3/2006 |
| WO | WO-2014138982 A1 | | 9/2014 |
| WO | WO-2016162774 A1 | | 10/2016 |
| WO | WO-2018115339 A1 | | 6/2018 |
| WO | WO-2019140462 A1 | | 7/2019 |
| WO | WO-2021231471 A1 | | 11/2021 |
| WO | WO-2021255714 A1 | | 12/2021 |
| WO | WO-2022081826 A1 | | 4/2022 |
| WO | WO-2023056459 | | 4/2023 |
| WO | WO-2023086957 | | 5/2023 |

OTHER PUBLICATIONS

Final Office Action in U.S. Appl. No. 17/834,457, dated Feb. 8, 2023, 23 pages.

International Preliminary Report on Patentability for International Application No. PCT/US2021/054952, dated Apr. 27, 2023, 8 pages.

Duarte, C. M. et al., "Can Seaweed Farming Play a Role in Climate Change Mitigation and Adaptation?" Frontiers in Marine Science, vol. 4, Article 100 (Apr. 2017), 8 pages, Retrieved from the Internet: https://doi.org/10.3389/fmars.2017.00100.

Goodwin, B., "GigaFarm Project Specification Document," 5273_Kombu, Phase 1.0, (Date Unknown), 12 pages.

International Search Report and Written Opinion for International Application No. PCT/US2022/077404, dated Dec. 12, 2022, 23 pages.

International Search Report and Written Opinion for International Application No. PCT/US2021/031833, dated Aug. 11, 2021, 13 pages.

International Search Report and Written Opinion for International Application No. PCT/US2021/054952, dated Jan. 19, 2022, 15 pages.

Krause-Jensen, D. et al., "Substantial role of macroalgae in marine carbon sequestration," Nature Geoscience, vol. 9, Issue 10, pp. 737-742 (Oct. 2016); published online Sep. 2016. https://doi.org/10.1038/ngeo2790.

Mooney-McAuley, K. M. et al., "Best Practice Guidelines for Seaweed Cultivation and Analysis," Report WP1A5.01, Energetic Algae ("EnAlgae"), Jun. 2016, 38 pages.

Office Action for U.S. Appl. No. 17/342,143 dated Nov. 24, 2021, 22 pages.

Peeples, T., "An inside look into blue evolution's seaweed hatchery," [Online], Blue Evolution, 2019, 5 pages, Retrieved from the Internet: URL: https://www.blueevolution.com/recipesblog/inside-look-seaweed-hatchery.

Redmond, S. et al., "Aquaculture in Shared Waters Kelp Aquaculture," Island Institute, Apr. 2015, 4 pages.

Stanford Environmental Health & Safety, "Information on Alkali Metals," [Online], Retrieved from the Internet: https://ehs.stanford.edu/reference/information-alkali-metals, Retrieved on Feb. 9, 2022, 4 pages.

Uykun, C., "Above-Ground Biomass and Carbon Estimations and Recommendations for Forests in Turkey," Michigan Technological University, Dissertations, Master's Theses and Master's Reports, 2018, 57 pages.

Walker, T., "Kelp farming in Alaska traces roots to hatcheries," [Online], Hatchery International, Oct. 2019, 5 pages, Retrieved from the Internet: URL: https://www.hatcheryinternational.com/kelp-farming-success-in-alaska-traces-roots-to-hatcheries/.

(56) References Cited

OTHER PUBLICATIONS

International Search Report and Written Opinion for International Application No. PCT/US2023/061782, dated Jun. 13, 2023, 13 pages.
International Search Report and Written Opinion for International Application No. PCT/US2023/064919, dated Jun. 26, 2023, 14 pages.
Anonymous, "Calcium Carbonate in Paint, Coatings, and Adhesives (PCA) Applications," OMYA Newsletter Summer 2011, 4 pages, retrieved online at https://www.omya.com/Documents/Vermont/Summer%202011.pdf.
Clark, S., "Rationale for Buoyant Flake Ocean Fertilization," Climate Game Changers, Jun. 18, 2018, 38 pages, retrieved online at https://climategamechangers.org/wp-content/uploads/Rationale-for-Buoyant-Flake-Ocean-Fertilisation.pdf.
Fernandez-Mendez M., et al., "Composition, Buoyancy Regulation and Fate of Ice Algal Aggregates in the Central Arctic Ocean", PLOS ONE, vol. 9, No. 9, Sep. 10, 2014 (Sep. 10, 2014), p. e107452, DOI: 10.1371/journal.pone.0107452.
International Search Report and Written Opinion for International Application No. PCT/US2023/064917, dated Jun. 26, 2023, 11 pages.

\* cited by examiner

10 

```
┌─────────────────────────────────────────────────────────────────┐
│ Release into a body of water a deployment including passive     │
│ substrates seeded with a target product and a sensor buoy       │
│                              11                                  │
└─────────────────────────────────────────────────────────────────┘
                                │
                                ▼
┌─────────────────────────────────────────────────────────────────┐
│ Obtain sensor data associated with at least one characteristic   │
│ of a target product of the sensor buoy                          │
│                              12                                  │
└─────────────────────────────────────────────────────────────────┘
                                │
                                ▼
┌─────────────────────────────────────────────────────────────────┐
│ Allow the passive substrates and the target product seeded      │
│ thereon to sink as a result of the passive substrates            │
│ transitioning from a positively buoyant state to a negatively   │
│ buoyant state                                                    │
│                              13                                  │
└─────────────────────────────────────────────────────────────────┘
                                │
                                ▼
┌─────────────────────────────────────────────────────────────────┐
│ Determine, based on the sensor data, an amount of biomass       │
│ accumulation associated with the target product of the sensor   │
│ buoy when the passive substrates transition to the negatively   │
│ buoyant state                                                    │
│                              14                                  │
└─────────────────────────────────────────────────────────────────┘
                                │
                                ▼
┌─────────────────────────────────────────────────────────────────┐
│ Determine a carbon sequestration capacity associated with the   │
│ target product of the passive substrates based at least in part │
│ on the amount of biomass accumulation associated with the       │
│ target product of the sensor buoy                               │
│                              15                                  │
└─────────────────────────────────────────────────────────────────┘
```

FIG. 23

SYSTEMS AND METHODS FOR MONITORING OCEAN-BASED CARBON DIOXIDE REMOVAL DEVICES AND ACCUMULATION OF A TARGET PRODUCT

CROSS-REFERENCE TO RELATED APPLICATIONS

This application is a continuation of International Patent Application No. PCT/US2022/079746, filed Nov. 11, 2022, entitled "Systems and Methods for Monitoring Ocean-Based Carbon Dioxide Removal Devices and Accumulation of a Target Product," which claims priority to and the benefit of U.S. Provisional Patent Application Ser. No. 63/278,243, filed Nov. 11, 2021, entitled "Systems and Methods for Monitoring Accumulation of a Target Product," the disclosure of each of which is incorporated herein by reference in its entirety.

BACKGROUND

This disclosure relates generally to ocean-based systems for capturing and sequestering greenhouse gases, and more particularly, to systems and methods for monitoring ocean-based carbon dioxide removal devices and/or accumulation of a target product and for storing and/or sending data associated with such monitoring.

Human activity has increased atmospheric carbon dioxide ($CO_2$) by approximately 50% (from about 280 to about 420 ppm) over the past 200-300 years due to the combustion of fossil fuels, land use changes, and other industrial processes. These anthropogenic increases in atmospheric $CO_2$ are causing a variety of environmental and societal problems, including global warming, increased wildfires, increased droughts, increased severity and frequency of storms, sea level rise, melting glaciers, and ocean acidification.

In general, the global carbon cycle operates through a variety of response and feedback mechanisms between the Earth's primary carbon reservoirs, namely the marine and terrestrial biospheres, the atmosphere, the ocean, and sediments/rocks. With respect to atmospheric carbon dioxide, the carbon cycle can be broken down into two distinct, but overlapping, components: the fast carbon cycle and the slow carbon cycle. The fast carbon cycle encompasses the movement of carbon via photosynthesis and respiration, as well as the continuous exchange of $CO_2$ amongst the biosphere, atmosphere, and ocean. The fast carbon cycle is dynamic and volatile, and it can be best understood as the flow of carbon through living ecosystems. In contrast, the slow carbon consists of the movement of carbon via gravity, pressure, chemical weathering, ocean currents, etc. These processes move carbon from living ecosystems into geological and/or deep-ocean reservoirs such as sediments, mineral deposits (e.g., oil, gas, coal), and deep waters. Slow carbon cycle reservoirs evolve very slowly.

One of the greatest challenges facing humanity in the 21st century is to develop scalable methods for removing and sequestering $CO_2$ from the atmosphere and/or upper ocean to limit the environmental and socio-economic damage that is associated with increasing $CO_2$ levels. Without human influence, carbon moves from the slow carbon cycle to the fast carbon cycle over millions of years through volcanic activity (e.g., driven by the subduction and melting of limestones and oil and gas-bearing rocks), and over intermediate timescales through ocean upwelling. Natural carbon cycling between the atmosphere, ocean, biosphere, and geologic reservoirs, in both the fast and slow carbon cycles, is generally balanced in a manner that promotes stable climates, ocean chemistry, and ecosystems. These geologic timelines, however, are much too slow to address the challenges we face today due to anthropogenic increases in atmospheric $CO_2$.

In an attempt to abate $CO_2$ emissions (and/or other greenhouse gas emissions), governments and regulatory authorities have established greenhouse gas emissions caps and have allowed organizations to comply with the emissions caps by purchasing, for example, carbon credits and/or offsets. Carbon credits can be bought and sold as amounts of carbon sequestered using carbon sequestration technology. Companies that achieve preset carbon offsets (e.g., becoming "carbon neutral") are often rewarded with financial incentives and/or tax benefits, which can be used to subsidize future projects for the reduction of greenhouse gas emissions.

Ocean-based interventions such as human cultivation of marine mass and/or other target products and sinking it/them to the ocean floor have shown promise as carbon sequestration technologies. Predicting the growth of marine species (and hence, its capacity to sequester carbon dioxide) and/or predicting the outcome of other interventions can enable a carbon sequestration capacity of such interventions to be bought and/or sold as carbon credits in a suitable market such as commodities market, futures market, etc. Some existing methodologies to assess and/or predict the growth of marine species and/or the outcome of other interventions generally rely on human observation and are often imprecise, inaccurate, labor intensive, and/or impracticable for large scale deployments. Sensors and/or other devices can be used to monitor the growth of marine mass and/or the status of other carbon removal interventions but monitoring devices in a suitable body of water such as an ocean can present unique challenges.

Accordingly, there is a need for improved methods and systems for monitoring ocean-based carbon dioxide removal devices and/or accumulation of marine mass and for storing and/or sending data associated with such monitoring.

SUMMARY

In some embodiments, an apparatus for monitoring ocean-based carbon dioxide removal devices and/or accumulation of a target product includes a first member having a housing that encloses a power source and a controller, a second member coupled to the first member and being seeded with a target product, and a sensing module coupled to the first member to allow power from the power source to be transmitted to the sensing module and sensor data from the sensing module to be transmitted to the controller. The sensing module including a sensor oriented toward at least a portion of the second member. The sensor configured to obtain sensor data associated with at least one characteristic of the target product.

BRIEF DESCRIPTION OF THE DRAWINGS

FIG. 23 is a flowchart illustrating a method of monitoring ocean-based carbon dioxide removal devices and/or accumulation of a target product, according to an embodiment.

DETAILED DESCRIPTION

Figure 1A:
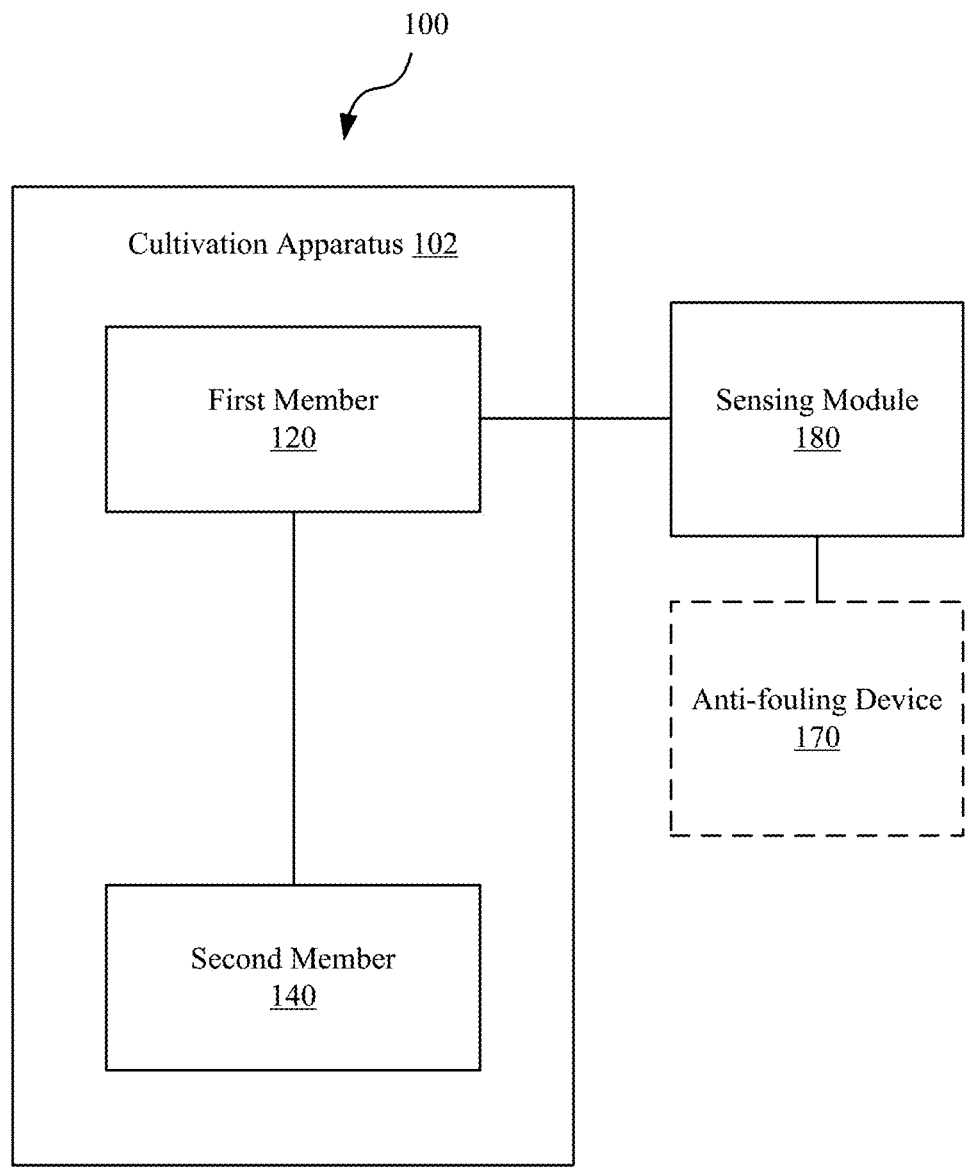
FIG. 1A is a schematic illustration of a cultivation apparatus included in a system for monitoring target product accumulation, according to an embodiment.

Systems and methods for monitoring ocean-based carbon dioxide removal devices and/or accumulation of a target product and for storing and/or sending data associated with such monitoring are described herein. Carbon dioxide removal ("CDR"), as described herein, is any activity that moves carbon from the rapidly cycling reservoir of carbon dioxide in the atmosphere into storage within a slow carbon cycle reservoir. Carbon removal is additive, durable, and quantifiable through direct measurements of mass transfers. When combined with rebuilding and conserving ecosystems that promote fast cycle carbon sinks, restorative carbon removal can both enhance the productivity of the fast carbon cycle while also moving carbon from the fast to slow carbon cycle. To be atmospherically significant, however, it is generally desirable for carbon sequestration technologies to be capable of capturing carbon at a multi-gigaton scale.

The ocean presents a potentially powerful mechanism for nature-based CDR. For example, the surface ocean is continually exchanging carbon dioxide with the atmosphere, annually fluxing about 100 Gigaton ("Gt") of $CO_2$ across the air/water exchange. In the photic zone (i.e., the region of a body of water that receives enough sunlight to allow for photosynthesis), it also fixes about Gt $CO_2$ in net primary production. Most of this carbon remains in the fast carbon cycle, but the ability of the ocean to capture and concentrate carbon dioxide from the air, albeit temporarily, may provide a lever for nature-based CDR. Moreover, the deep ocean is a substantial carbon sink—durably holding about 37,000 Gt $CO_2$ in dissolved carbon away from atmospheric mixing for hundreds to thousands of years. However, the natural mechanism of carbon transfer from surface-ocean atmospheric flux to deep sea storage is relatively limited, resulting in about 10 Gt $CO_2$ annual sequestration. Thus, "ocean CDR" or "ocean-based CDR," as described herein, represents a set of systems, methods, and/or engineering interventions to amplify this transfer of carbon from fast carbon cycle (e.g., at the surface of the ocean) to the slow carbon cycle (e.g., in or at deep ocean).

Embodiments and methods described herein, in general, are configured to perturb the chemistry and/or chemical properties of the surface ocean (or a surface layer of any other body of water), such that those perturbations result in dissolution of atmospheric carbon into the ocean and/or amplification of ocean transfer of carbon from fast carbon cycles to slow carbon cycles. For example, increasing the yield of photosynthetic biomass in the surface ocean produces a chemical perturbation through the uptake and removal of dissolved inorganic carbon (DIC) from the water. Another such example is the direct addition of dissolved or dissolving alkaline material to the water, changing its pH. These perturbations, when applied to targeted areas of the surface ocean, may result in carbon sequestration of commercial quality.

Examples of ocean-based CDR can include but are not limited to the cultivation, accumulation, and sequestration of marine biomass; chemical weathering of alkaline minerals and/or fluids; enhancing ocean alkalinity and/or mineralization; and/or the like. Any of the embodiments and/or methods described herein can be used to monitor and/or otherwise collect data associated with one or more ocean-based CDR intervention(s) such as any of those described in U.S. Provisional Application No. 63/401,959 ("the '959 provisional"), filed Aug. 29, 2022, entitled "Ocean Based Carbon Removal Systems and Method of Using the Same," the disclosure of which is incorporated herein by reference in its entirety. For example, in some implementations, the embodiments and/or methods described herein can be used to monitor and/or collect data associated with the cultivation, accumulation, and/or sequestration of marine biomass. While this implementation is described in detail herein, it should be understood that the embodiments and/or methods described herein are not limited to such implementations. Any of the embodiments and/or methods described herein can be implemented—or can be adapted for implementation—in any suitable ocean-based CDR intervention(s) such as any of those described in the '959 provisional.

Ocean-based CDR using marine biomass generally includes providing, at least temporarily, a structure, substrate, platform, or other means for cultivating one or more marine species ("target product(s)"), allowing the target product(s) to accumulate biomass, and sequestering the target product(s) after a desired amount of accumulation (e.g., by sinking the biomass with or without the substrate to the bottom of a body of water such as the ocean). "Target product(s)," as described herein, includes and/or encompasses a wide variety of species including but not limited to microalgae, macroalgae, plankton, marine bacteria, archaea filter feeders (such as oysters or clams), and/or crustaceans either for the purpose of cultivation and/or for sequestering carbon dioxide.

Many target products (e.g., macroalgae) show promise as a carbon sequestration pathway as their wild growth currently contributes to naturally occurring carbon sequestration to the seafloor. Target product cultivation has the potential to improve this sequestration rate significantly due to increased cultivation productivity and increased sinking/sequestration rate relative to these naturally occurring phenomena. Target products can be cultivated in oceans, estuaries, lakes, rivers, and/or any other suitable body of water. These target products can be allowed to grow and accumulate biomass. Biomass may be corporeally retained or eroded (allowed to naturally break off and sink) into the water. When biomass/target products sink, they contribute to carbon sequestration. Therefore, after accumulation of biomass reaches a certain threshold value, the target products are allowed (or caused) to sink to the bottom of the body of water (e.g., the sea-floor, ocean-floor, etc.), thereby effectively sequestering the carbon dioxide associated with the accumulated target product.

In some implementations, cultivation can include seeding a substrate or structure with a target product, deploying the seeded substrate in a body of water such as open ocean, and allowing biomass to accumulate until reaching a certain threshold value. After accumulating a desired or threshold amount of biomass, the target product is allowed (or caused) to sink to the ocean floor, thereby effectively sequestering an amount of carbon dioxide captured by the target product via photosynthesis. Various devices, systems, and/or methods associated with the cultivation and sequestration of target products and/or the substrates or other structures supporting or being seeded therewith can include but are not limited to, for example, those described in the '959 provisional; U.S. Pat. No. 11,382,315 ("the '315 patent"), filed Jun. 8, 2021, entitled, "Systems and Methods for the Cultivation of Target Product;" U.S. patent application Ser. No. 17/957,681 ("the '681 application"), filed Sep. 30, 2022, entitled "Systems and Methods for Quantifying and/or Verifying Ocean-Based Interventions for Sequestering Carbon Dioxide;" U.S. Provisional Application No. 63/323,285 ("the '285 provisional"), filed Mar. 24, 2022, entitled "Floating Substrates for Offshore Cultivation of Target Products and Methods of Making and Using the Same;" and/or U.S. Provisional Application No. 63/323,286 ("the '286 provisional"), filed Mar. 24, 2022, entitled "Floating Substrates Including Carbonaceous Coatings for Offshore Cultivation of Target Products and Methods of Making and Using the Same," the disclosures of which are incorporated herein by reference in their entireties.

Since target products are cultivated in water bodies, particularly remote areas of an ocean or other large body of water where they may best accumulate biomass, it is desirable to configure and/or design the cultivation devices, apparatus, substrates, structures, etc. to be able to withstand and/or tolerate harsh environmental conditions and weather conditions such as water turbulence, over exposure to sunlight, saltwater breaches, etc. Accordingly, it may be desirable to deploy a number of cultivation apparatus that are relatively inexpensive and that passively float on the water until the target product accumulates a desired amount of biomass at which point the cultivation apparatus and target product are allowed to sink. In addition, to sequester atmospherically significant amounts of carbon it may be desirable to deploy a system having a large number of such passive cultivation apparatus (e.g., hundreds, thousands, tens of thousands, hundreds of thousands, or more).

However, monitoring accumulation of the target products cultivated in or by the system and/or otherwise controlling, coordinating, and/or relaying data to or from the deployed system can be challenging. For example, most components (e.g., electrical and/or electronic components such as sensors, etc.) used for monitoring marine mass need a source of power. Power drawdown by the components can make power source(s) a limiting resource in water bodies. Additionally, sensors and other components used for monitoring marine mass are generally rely on remote human monitoring and can be susceptible to failure due to seawater breaches, turbulence, overexposure to sunlight, fouling (e.g., as a result of residue, biofilm, slime, and/or the like), etc., which may shorten the life of structures and/or may affect the quantity and/or quality of data being collected.

To overcome these challenges, systems and methods are described herein for monitoring ocean-based carbon dioxide removal devices and/or accumulation of target products and for storing and/or sending data associated with such monitoring. In general, the embodiments described herein can be floatable sensor buoys or the like that can include, for example, a power source, a controller, and a sensing module. Such an arrangement can allow the sensor buoys to monitor and/or otherwise collect data associated with a system deployed in a body of water (e.g., a deployment of passive cultivation apparatus), an amount of biomass accumulated by the target product cultivated by the system, and/or environmental condition(s) in an area where the system is deployed (e.g., a portion of the ocean). In some implementations, the monitoring and/or data collected can be used to determine and/or predict an amount of carbon dioxide that can be sequestered by the overall system. The embodiments can be retrievable allowing them to be used in multiple deployments. On the other hand, in some implementations, the embodiments can include one or more features, components, and/or devices that enable the sensor buoy to be remotely scuddled (e.g., if it floats into a shipping lane or for any other reason).

In some embodiments, the embodiments and/or systems described herein can include a first member configured to monitor the accumulation of the target product(s) seeded on a second member. The first member can provide buoyancy, at least temporarily, to various components of the system and to at least partially house various components such as a power source, a controller (and/or other electronics), and/or the like. The power source can be configured to provide power to the controller (and/or other electronics) and at least one sensing module configured to obtain sensor data that can be representative of one or more characteristics associated with biomass accumulation of the target product seeded on or in the second member. The controller and/or other electronics can receive the sensor data and/or any other suitable data associated with the system and/or the deployment environment and, in turn, can use the data to determine and/or predict an amount of accumulation of the target product seeded on or in the second member. In some implementations, the determination and/or prediction of the accumulation can be used to determine, infer, and/or predict an amount of biomass accumulation for all the target product cultivated by the system (e.g., all the target product seeded on the individual passive cultivation apparatus in a deployment).

In some embodiments, an apparatus for monitoring accumulation of a target product includes a first member having a housing that encloses a power source and a controller, a second member coupled to the first member and being seeded with a target product, and a sensing module coupled to the first member to allow power from the power source to be transmitted to the sensing module and sensor data from the sensing module to be transmitted to the controller. The sensing module including a sensor oriented toward at least a portion of the second member. The sensor configured to obtain sensor data associated with at least one characteristic of the target product.

In some embodiments, an apparatus for monitoring accumulation of a target product includes a support structure, a first member, a second member, a sensing module, and a scuttling device. The first member has a housing coupled to the support structure and a one way valve in communication with an inner volume of the housing. The second member is coupled to the first member and the support structure. The second member is configured to be seeded with the target product. The sensing module coupled to the support structure such that a sensor of the sensing module is oriented toward at least a portion of second member. The sensor is configured to obtain sensor data associated with at least one characteristic of the target product. The scuttling device is coupled to the support structure and includes a chamber that defines an inner volume in communication with the inner volume of the housing via the support structure. The scuttling device includes a plug movably coupled to the chamber and a motor disposed in the inner volume of the chamber. The motor is configured to move the plug from a closed state in which the chamber is sealed allowing the apparatus to maintain positive buoyancy in a body of water to an open state in which the plug allows a flow of water into the inner volume of the chamber. The one way valve of the first member is configured to allow a flow of air out of the inner volume of the housing as water flows into the inner volume of the chamber, thereby allowing the apparatus to become negatively buoyant.

In some embodiments, a method includes releasing a deployment of passive substrates into a portion of a body of water. The passive substrates are seeded with a target product. The deployment also includes a sensor buoy. The sensor buoy includes a first member configured to at least temporarily maintain a positive buoyancy of the sensor buoy, a second member seeded with the target product, and a sensing module having a sensor oriented toward at least a portion of the second member. The method includes obtaining sensor data associated with at least one characteristic of the target product of the second member. The passive substrates and the target product seeded thereon are allowed to sink as a result of the passive substrates transitioning from a positively buoyant state to a negatively buoyant state. When the passive substrates transition to the negatively buoyant state, an amount of biomass accumulation associated with the target product of the second member is determined based on the sensor data and a carbon sequestration capacity associated with the target product of the passive substrates is determined based at least in part on the amount of biomass accumulation associated with the target product of the second member.

The terminology used herein is for the purpose of describing particular embodiments only and is not intended to limit the full scope of the claims. Unless defined otherwise, all technical and scientific terms used herein have the same meanings as commonly understood by one of ordinary skill in the art.

As used in this specification, the singular forms "a," "an," and "the" include plural referents unless the context clearly dictates otherwise. For example, the term "a member" is intended to mean a single member or a combination of members, "a material" is intended to mean one or more materials, or a combination thereof. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims, are generally intended as "open" terms (e.g., the term "including" should be interpreted as "including but not limited to," the term "having" should be interpreted as "having at least," etc.). For example, the terms "comprise(s)" and/or "comprising," when used in this specification, are intended to mean "including, but not limited to." While such open terms indicate the presence of stated features, integers (or fractions thereof), steps, operations, elements, and/or components, they do not preclude the presence or addition of one or more other features, integers (or fractions thereof), steps, operations, elements, components, and/or groups thereof, unless expressly stated otherwise.

As used herein the term "and/or" includes any and all combinations of one or more of the associated listed items. Said another way, the phrase "and/or" should be understood to mean "either or both" of the elements so conjoined (i.e., elements that are conjunctively present in some cases and disjunctively present in other cases). It should be understood that any suitable disjunctive word and/or phrase presenting two or more alternative terms, whether in the description, claims, or drawings, contemplate the possibilities of including one of the terms, either of the terms, or both terms. Other elements may optionally be present other than the elements specifically identified by the "and/or" clause, whether related or unrelated to those elements specifically identified. Thus, as a non-limiting example, a reference to "A and/or B" can refer to "A" only (optionally including elements other than "B"), to "B" only (optionally including elements other than "A"), to both "A" and "B" (optionally including other elements), etc.

As used herein, "or" should be understood to have the same meaning as "and/or" as defined above. For example, when separating items in a list, "or" or "and/or" shall be interpreted as being inclusive (e.g., the inclusion of at least one, but also including more than one of a number or list of elements, and, optionally, additional unlisted items). Only terms clearly indicated to the contrary, such as when modified by "only one of" or "exactly one of" (e.g., only one of "A" or "B," "A" or "B" but not both, and/or the like) will refer to the inclusion of exactly one element of a number or list of elements.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements, unless expressly stated otherwise. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B" or "at least one of A and/or B") can refer to one or more "A" without "B," one or more "B" without "A," one or more "A" and one or more "B," etc.

All ranges disclosed herein are intended to encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member and/or a fraction of an individual member where appropriate.

As used herein, the terms "about," "approximately," and/or "substantially" when used in connection with stated value(s) and/or geometric structure(s) or relationship(s) is intended to convey that the value or characteristic so defined is nominally the value stated or characteristic described. In some instances, the terms "about," "approximately," and/or "substantially" can generally mean and/or can generally contemplate a value or characteristic stated within a desirable tolerance (e.g., plus or minus 10% of the value or characteristic stated). For example, a value of about 0.01 can include 0.009 and 0.011, a value of about 0.5 can include 0.45 and 0.55, a value of about 10 can include 9 to 11, and a value of about 100 can include 90 to 110. Similarly, a first surface may be described as being substantially parallel to a second surface when the surfaces are nominally parallel. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the terms "about," "approximately," and/or "substantially" can be used herein to account for such tolerances and/or considerations.

Referring to the drawings, FIG. 1A is a schematic illustration of a system 100 for monitoring target product accumulation, according to an embodiment. The target product can be cultivated on or in a cultivation apparatus 102 deployed in a suitable body of water (e.g., estuary, ocean, etc.). As discussed above, target product(s) can include and/or encompass a wide variety of species including but not limited to microalgae, macroalgae, plankton, marine bacteria, archaea filter feeders (such as oysters or clams), and/or crustaceans. The target product can be grown on the cultivation apparatus 102 deployed in a suitable water body. The cultivation apparatus 102 can be any suitable shape, size, and/or configuration. In some embodiments, for example, the cultivation apparatus 102 can be similar to or substantially the same as any of the cultivation apparatus described in the '315 patent and/or the '681 application (incorporated by reference above).

For example, the cultivation apparatus 102 can include a first member 120 (e.g., a buoy) and a second member 140. In some implementations, the cultivation apparatus 102 can optionally include a release component configured to temporarily couple the first member 120 and the second member 140 and to allow the first member to separate, disconnect, release, and/or decouple from the second member 140 in response to one or more criteria being satisfied (e.g., after a desired amount of time, target product accumulation, and/or the like). The cultivation apparatus 102 can include a first member 120 (also referred to as a "buoy") to provide buoyancy to various components of the cultivation apparatus 102 and monitor the accumulation of one or more target product coupled to and/or seeded on a second member 140 of the cultivation apparatus 102. A sensing module 180 can be coupled to or otherwise integrated with the cultivation apparatus 102. In some embodiments, the sensing module 180 can be mechanically coupled to the cultivation apparatus 102. For example, the sensing module 180 can be coupled to the first member 120 via a support structure (not shown in FIG. 1A). The sensing module 180 can be configured to sense, detect, measure, and/or quantify one or more characteristics and/or images relevant to the accumulation and/or growth of the target product disposed on the cultivation apparatus 102. In some embodiments, a portion of the cultivation apparatus 102 (e.g., the first member 120), the cultivation apparatus 102, and/or the sensing module 180 can be in communication with one or more external device (s), external processor(s), server(s), etc., via one or more network(s), as further described in FIG. 1D.

The first member 120 of the cultivation apparatus 102 can be any suitable shape, size, and/or configuration. In some embodiments, the first member can be at least structurally and/or functionally similar to the first members described in detail in the '315 patent and/or the '681 application. For example, one or more portions of the first member 120 can be formed of a porous and/or hollow material configured to provide buoyancy to or for the cultivation apparatus 102. In some embodiments, one or more portions of the first member 120 can be formed of a material relatively permeable to oxygen, carbon dioxide, water, and water-soluble nutrients to enable growth of target product. In some embodiments, one or more portions of the first member 120 can be formed of a relatively transparent material configured to allow absorption of visible light.

In some implementations, the first member 120 or buoy of the cultivation apparatus 102 can be seeded with and/or configured to receive a species of target product (e.g., macroalgae gametophytes and/or sporophytes) that becomes positively buoyant as the target product matures. In other implementations, the first member 120 can be seeded with and/or configured to receive a species of target product that is and/or that becomes negatively buoyant as the target product matures. In other implementations, the first member 120 need not be seeded with and/or configured to receive a target product. For example, in some implementations, only the second member 140 is seeded with a target product while the first member 120 acts, at least temporarily, as a buoy or the like that is not seeded with a target product. As such, the first member 120 can be a buoy or the like that can include and/or house any number of components, controllers, sensors, imaging devices, communication devices, radios, etc. configured to collect data associated with the cultivation apparatus 102 and/or an environment in which the cultivation apparatus 102 is deployed (e.g., an area of the ocean), to process, analyze, compress, condition, transform, etc. the collected data, and/or to transmit the data to, for example, another first member, acting as a node of a mesh network, and/or the one or more external device(s), external processor(s), server(s) (e.g., server 110 in FIG. 1D), as described in further detail herein.

In some embodiments, the first member 120 can include an attachment mechanism that can at least temporarily mechanically couple the first member 120 to a support structure (not shown in FIG. 1A) and/or the second member 140. For example, a distal end portion of the first member 120 can include loops, rings, hooks, etc. The support structure can be disposed directly below and/or can extend from the first member 120 such that the attachment mechanism couples the support structure to the first member 120. The second member 140 (e.g., a proximal end portion of the second member 140) can be at least temporarily coupled to the attachment mechanism via a chain and/or a link. The second member 140 can be positioned such that the second member 140 is parallel to and adjacent to the support structure. Alternatively, the support structure can be integrated with or otherwise attached to the first member 120 and the second member 140 can be coupled to the attachment mechanism of the first member 120. For example, the support structure can be welded to the first member 120 and the second member 140 can be temporarily coupled to the first member 120 via the attachment mechanism, a release mechanism, and/or any other coupling method.

The second member 140 is configured to be seeded with one or more species of the target product and can provide a structure that allows the cultivation and/or accumulation of the target product as the target product matures. The second member 140 can be any suitable shape, size, and/or configuration. For example, in some embodiments, the shape, size, and/or configuration of the second member 140 can be similar to or substantially the same as the shape, size, and/or configuration of the first member 120 or buoy. In other embodiments, the shape, size, and/or configuration of the second member 140 can be different than the shape, size, and/or configuration of the first member 120 or buoy. In some embodiments, the second member 140 can be and/or can include one or more seeding lines and/or the like. In some embodiments, the second member 140 can be similar to or substantially the same as any of the second members described in detail in the '315 patent and/or the '681 application.

In some implementations, the cultivation apparatus 102 can be used to seed one or more species of a target product(s) that may be utilized in carbon sequestration. For example, in some instances, at least the second member 140 of the cultivation apparatus 102 can be seeded with a target product species (e.g., macroalgae gametophytes and/or sporophytes), and once seeded, the cultivation apparatus 102 can be deployed on oceans, lakes, rivers, estuaries, and/or any other suitable body of water. In some embodiments, at least the second member 140 of the cultivation apparatus 102 can be negatively buoyant and/or can be seeded with target product(s) that become negatively buoyant as they mature. The first member 120 of the cultivation apparatus 102 can be configured such that the cultivation apparatus 102 is positively buoyant when initially deployed, allowing at least a portion of the cultivation apparatus 102 to float for a predetermined period after deployment, and then allowing at least a portion of the cultivation apparatus 102 (e.g., at least the second member 140) to gradually sink as the negatively buoyant target product seeded on the second member 140 grows and obtains biomass.

In some embodiments, the second member 140 can be at least temporarily coupled to the first member 120 via a release component and/or the like, as described in detail in the '315 patent and/or the '681 application. For example, in some embodiments, such a release component can couple the second member 140 to the first member 120 while the target product seeded on the second member 140 grows to maturity. After a desired amount of growth and/or accumulation of the target product, the release member can be configured to degrade and/or otherwise mechanically separate, disconnect, detach, release and/or decouple from the first member 120 and/or the second member 140. For example, the release component can be configured to detach, release, and/or decouple after a predetermined amount of time has elapsed, after the selected species of target product has grown and/or obtained a predetermined amount of mass, and/or after a signal or group of signals operable to actuate the release component have been received. In some implementations, the detaching, releasing, and/or decoupling can allow the first member 120 (and any target product attached thereto and/or electrical or electronic components disposed therein) to float and the second member 140 (and any target product attached thereto) to sink. The first member 120 can be then retrieved and/or reused while the second member 140 sinks to the bottom of the body of water (e.g., ocean), which in turn, can sequester carbon dioxide captured by and/or associated with the grown target product. In implementations in which the first member 120 is seeded, the target product can be harvested and used and/or sold for any suitable purpose. In some implementations, including the electronic components (e.g., sensors, imaging devices, tracking devices, communication devices, compute devices, and/or any other of the devices described above) in or on the first member 120 that is configured to float after being detached can allow the components to be reused in another deployment. In some instances, the first member 120 can be retrieved, and data associated with the cultivation apparatus 102 and/or the target product that is stored in a memory device or the like can be downloaded and/or retrieved.

The sensing module 180 of the cultivation apparatus 102 can be any suitable device and/or assembly or combination of devices configured to sense one or more characteristics associated with the target product accumulation and/or the environmental conditions where the cultivation apparatus 102 is deployed. The sensing module 180 and/or at least a portion thereof can be positioned at and/or near the distal end portion of the second member 140. For example, the sensing module 180 can include and/or can be coupled to a support structure and/or frame such that the sensing module 180 is positioned at or near the distal end portion of the second member 140. In some implementations, the support structure can be coupled to the first member 120 and can extend therefrom to be parallel and/or adjacent to the second member 140 such that one or more sensors are disposed at or near the distal end portion of the second member 140. In some embodiments, the support structure can allow the second member 140 to couple at least temporarily to the support structure via a release member, link (e.g., chain, etc.), and/or the like. In some embodiments, the frame of the sensing module 180 can orient one or more sensors towards the target product. More specifically, the one or more sensors of the sensing module 180 can be coupled to, integrated with, or otherwise attached to the frame, which in turn, can orient the one or more sensors such that each sensor can capture sensor data from at least a section of the target product and/or from the second member 140.

The sensing module 180 can include any number of devices, sensors, image and/or video capture devices, and/or assembly or combination of devices configured to sense and/or collect data (or configured to facilitate the sensing or collecting of data) associated with the target product accumulation and/or the environmental conditions where the cultivation apparatus 102 is deployed. For example, in some embodiments, the sensing module 180 can include one or more sensors configured to sense, detect, and/or measure water temperature, irradiance, dissolved oxygen concentration, pH, concentration of nutrients in the water, concentration of dissolved carbon in the water, water salinity, target product (e.g., plant) size, target product density, photosynthetic energy conversion of the target product (e.g., via chlorophyll fluorescence and/or the like), and/or other characteristics related to target product growth, the cultivation apparatus 102, and/or the environment in which the cultivation apparatus 102 is deployed. The one or more sensors can provide data, which in turn, can be used to determine, quantify, calculate, model, etc. the accumulation of biomass and/or an amount of carbon that can be captured and sequestered by the target product, as described in detail in the '315 patent and/or the '681 application.

For example, in some embodiments, the sensing module 180 can include pressure-release depth sensors configured to measure, and/or record the sinking rate of one or more portions of a cultivation apparatus 102. The pressure-release depth sensors can be configured to measure, and/or record the sinking rate as a function of time after the cultivation apparatus 102 is seeded with target product and deployed on oceans, lakes, rivers, and/or any other suitable body of water. For example, the pressure-release depth sensors can be configured to measure the sinking rate of the cultivation apparatus 102, decouple from the cultivation apparatus 102 once the cultivation apparatus 102 reaches a predetermined depth threshold, return to the surface, and emit the sinking rate information recorded via satellite or other wireless communication. In some instances, the sinking rate of the cultivation apparatus 102 can be used to quantify the mass and related carbon captured and/or sequestered. In some instances, the pressure-release depth sensors of the sensors can be used to determine whether the cultivation apparatus 102 has sunk below a predetermined depth or threshold associated with and/or suitable for the permanent sequestration carbon.

In some embodiments, the sensors can be configured to sense, detect, and/or monitor target product growth, mass generation, and/or mass yield upon the cultivation apparatus 102 being seeded with target product, and being deployed on oceans, lakes, rivers, and/or any other suitable body of water. In some embodiments, the sensors can include underwater cameras or other imaging technologies configured to image, record, and/or monitor any number of target products (e.g., plants and/or heterokonts like kelp, macroalgae, etc.), number of fronds per target product, frond dimensions, and/or density associated to target product growth. For example, in some embodiments the sensors can include a stereoscopic camera system equipped with two or more lenses including separate image sensors to simulate human binocular vision and thus facilitate obtaining images with perception of depth. In some embodiments, the stereoscopic camera system can be equipped with one or more rectilinear lenses, fisheye lenses, and/or anamorphic lenses configured to produce detailed images of the target product growing on the cultivation apparatus 102.

In some embodiments, the stereoscopic camera system can be configured to perform multiple image post processing steps. For example, in some embodiments, the stereoscopic camera system can include a post processing step to analyze the images generated by the lenses and identify and/or correct distortions using algorithms that estimate distortion parameters and camera matrix through the use of, for example, a Levenberg-Marquardt solver and/or any other suitable curve fitting methods. In some embodiments, the stereoscopic camera system can include multiple post processing steps such as color correction, brightness/contrast, sharpness, backscatter removal, cropping and the like. In some implementations, the post processing steps can include analyzing the image data using computer vision and/or other machine learning techniques to determine characteristics of the target product represented in the image data. In some embodiments, the stereoscopic camera system can capture the raw image data and transmit the data to the first member 120, which in turn, can perform any of the post processing steps just described.

In some embodiments, the sensors can also include cameras equipped with Photosynthetically Active Radiation (PAR) sensors or other irradiance measuring devices configured to measure photosynthetic light levels in air and water in the 400 to 761 nm range (or any other suitable range of wavelength). The PAR sensors can be configured to measure photosynthetic photon flux density (PPFD) or the power of electromagnetic radiation in the visible light spectral range in micromoles of photons per square meter per second. The data captured by the PAR sensors or other devices can be used to estimate, determine, and/or quantify the intensity of solar light that is available to the target product disposed on the cultivation apparatus 102 for photosynthesis, and thus estimate and/or infer the relative health of the target product and/or the rate of growth of target product as well as other marine organisms. Similarly, the sensors can also include chlorophyll fluorometers configured to detect light that is re-emitted by chlorophyll molecules as part of the process of photosynthetic energy conversion. In some implementations, the sensors can include a combination of PAR sensors, fluorometers, and/or any other suitable sensor.

The images, and/or sensor data captured and/or recorded by the sensors (e.g., cameras, PAR sensors, fluorometers, etc.) can be used to quantify and/or estimate, at least in part, the mass accumulated on the cultivation apparatus 102, an amount of mass eroded from the cultivation apparatus 102 (e.g., allowed to naturally break off and sink), and/or changes in the mass (e.g., rate of mass accumulation). The images and/or sensor data can, for example, provide insights that facilitate evaluating the relative health of the target product. In some embodiments, the images and/or sensor data captured and/or recorded by the sensors can be transmitted to the first member 120 via the support structure. In some instances, the image data and/or the like captured and/or recorded by the sensors can be analyzed manually (e.g., manual annotation by a user) to determine the amount of mass on the cultivation apparatus 102, the rate of growth of target product, and/or the amount of $CO_2$ effectively captured by the mass accumulated on the cultivation apparatus 102. For example, in some embodiments, the sensors can initiate image capture (e.g., capture or record images and/or videos of the target product attached to and/or otherwise associated with the cultivation apparatus 104 at different points in time), post process those images (e.g., adjust color, brightness/contrast, sharpness, backscatter removal, removal of noise, cropping and the like) and transmit the images and/or videos (e.g., to the first member) for data extraction or annotation by a user, and statistical analysis of the extracted data. In other instances, the image data (or other sensor data) captured and/or recorded by the sensors can be analyzed or annotated using computer vision algorithms (e.g., executed on or by controller included in the first member 120).

While examples of sensors and/or cameras are described above, it should be understood that they have been provided as example only and not limitation. The sensing module 180 can include sensors and/or devices in addition or as an alternative to those specifically described above. In some embodiments, the sensing module 180 of the cultivation apparatus 102 can include a first type, set, and/or combination of sensors, which a sensing module of a different cultivation apparatus in a deployment can include a second type, set, and/or combination of sensors that is different from the first. Accordingly, the sensing module of one or more cultivation apparatus included in a deployment can be selected and/or configured to collect any desired data associated with a target product, environment conditions, and/or any other data.

In some embodiments, the sensing module 180 can include and/or can be connected with an anti-fouling device 170, as shown in FIG. 1A. The anti-fouling device can be configured to detect, inhibit, prevent, and/or minimize the degradation, contamination, and/or fouling of the various components of the sensing module 180 (e.g., sensor(s)) due to accumulation and/or growth of marine microorganisms, plants, algae, or small animals, as well as the microbiologically influenced corrosion (MIC) generated by metabolites of such marine microorganisms. Some known anti-fouling devices for cleaning under water structures involve the use of mechanical cleaning methods such as using brushes and wipers. Wiper or brush based anti-fouling systems are purely mechanical methods and often not feasible for sensors with sensitive components. For example, wiper or brush material (s) are selected carefully to avoid and/or minimize scratching the surface or other parts of sensors. Copper is a commonly used material for wipers and/or brushes in under water anti-fouling systems. However, with mechanical structures such as rotating brushes or wipers in anti-fouling systems, the moving parts present in unforgiving ocean environment(s) can push the parts to failure either through mechanical breakage, corrosion, or fouling of the moving part itself. In addition, brushes or wipers may not be able to clear a sensor window or surface of all or substantially all highly adhesive slime-type residues. Furthermore, copper may not be suitable for all applications like the optical window of a sensor and so it may be limited in effectiveness. In addition, copper is likely to corrode/dissolve/chip away, thereby reducing its antifouling capabilities.

Thus, in some implementations, the anti-fouling device(s) 170 described herein can be static devices (e.g., a device with no moving parts), making it/them suitable for deployment (e.g., long-term deployment) in oceanic environments and/or the like. For example, FIG. 1A shows an implementation of the anti-fouling device 170 connected and/or integrated with the sensing module 180. The anti-fouling device 170 can be any suitable static device configured to detect, inhibit, prevent, and/or minimize deterioration, contamination, and/or fouling of one or more portions, surfaces, windows, etc. of one or more sensors of the sensing module 180.

For example, in some embodiments, the sensing module 180 can include a sensor configured as a fluorometer and/or the like, which can include a detection light source such as a Light-Emitting-Diode (LED) lamp configured to emit a beam of light (e.g., in at least a portion of the visible spectrum) toward the target product (e.g., one or more microorganisms, plants, algae, small animals, etc.). In response, fluorophores of the target product can emit fluorescence, which in turn, can be detected by one or more detectors such as a charge-coupled device (CCD), an electron-multiplying charge coupled device (EM-CCD), and/or a complementary metal oxide semiconductor (CMOS) detector. The detectors can quantify the intensity of a fluorescence signal that can be used to evaluate the accumulation of marine microorganisms on the sensors.

In some implementations, the sensing module 180 can be coupled to, can include, and/or can be integrated with the anti-fouling device 170. For example, the anti-fouling device 170 can be and/or can include a secondary light source configured to emit a beam of light in the ultraviolet spectrum (e.g., between 250 nm and 280 nm) to one or more lenses, surfaces, windows, and/or other components of the sensor (e.g., fluorometer). In some instances, the UV light emitted by the anti-fouling device 170 can remove at least a fraction of the marine microorganisms, biofilm, and/or other biological debris accumulated on the lenses, surfaces, windows, etc. of the sensors due to the microorganism's low tolerance to the frequency and/or wavelengths of UV radiation generated by the UV light source of the anti-fouling device 170. As described in further detail herein with respect to specific embodiments, the anti-fouling device 170 can be integrated into and/or with any number of sensors, allowing the anti-fouling device 170 to "clean" the sensors or lenses thereof, while not interfering with the detection capabilities of the sensors.

Figure 1B:
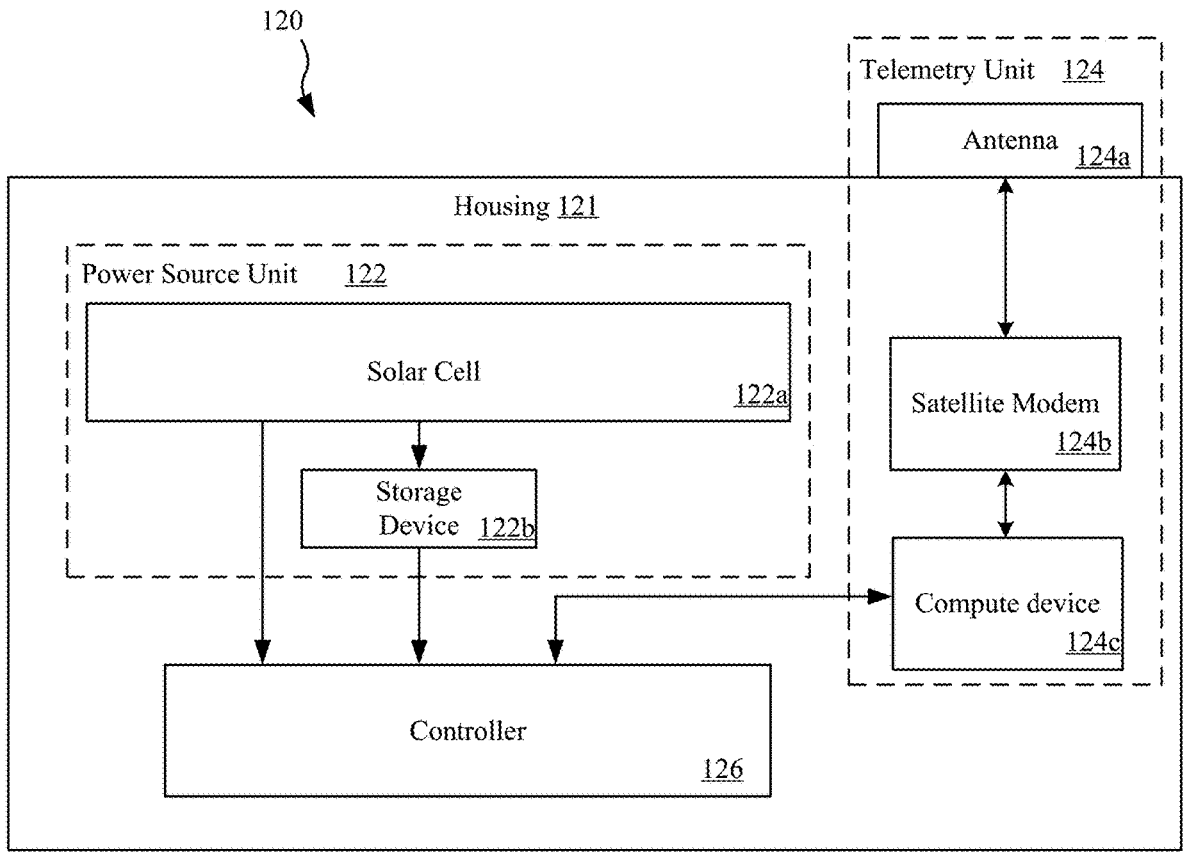
FIG. 1B is a schematic illustration of at least some electronic components included in a first member of the cultivation apparatus shown in FIG. 1A.

As described above, the first member 120 can include any device or combination of devices configured to receive, analyze, process, aggregate, and/or otherwise use data (e.g., collected by the sensing module 180 and/or received from remote or external sources) to allow and/or enable monitoring of the accumulation of the target product as it matures. For example, FIG. 1B is a schematic illustration of the first member 120 and at least some electronic components that can be included and/or housed therein. For example, the first member 120 can include a housing 121 that encloses a power source 122 to provide power to the sensing module 180 (and any of electrical or electronic components), a telemetry unit 124 to collect and/or transmit data with one or more remote sensing sources (telemetry data), and a controller 126 to analyze the telemetry data and/or sensor data obtained from the sensing module 180 and/or to otherwise control one or more portions of the cultivation apparatus 102. The housing 121 can be a waterproof housing to protect the power source 122, the telemetry unit 124, and the controller 126 (e.g., protect from damage due to water). The housing 121 can include an enclosure comprising plastic, metal (e.g., aluminum, steel, etc.), or a combination thereof.

In some embodiments, the power source 122 can include an energy storage device 122b (e.g., battery) and/or solar cells 122a (e.g., solar panel). The solar cells 122a can produce direct current (DC) energy. In some embodiments, the power source 122 can include a collection of solar cells 122a forming a solar panel. In some embodiments, the solar panel can be disposed above a top surface of the housing 121. Alternatively, at least a portion of a top surface of the housing 121 can be transparent. For example, at least a portion of or all of the top surface of the housing 121 can include polycarbonate sheets such as Lexan and/or other transparent plastic sheets. The solar panel can be disposed within the housing 121 itself such that it is positioned adjacent to the top surface (e.g., the transparent portion) of the housing 121. For example, the solar panel can be disposed below the top surface of the housing 121 such that it is positioned adjacent to the top surface. In some embodiments, one or more solar cells 122a can be attached to the inner portion of the top surface of the housing 121 such that the solar cells 122a are positioned within the housing 121. For example, one or more solar cells 122a can be attached to the top surface inside the housing 121 using a suitable adhesive (e.g., adhesive patch, glue, paste, etc.) such that the solar cells 122a are positioned adjacent to the top surface of the housing. The solar cells 122a can produce or output any suitable range of power. For example, in some embodiments, a solar panel included in the first member 120 can generate 17 Watts (W) of power. In some embodiments, six solar cells 122a can be attached to the inner portion of the top surface of the housing 121 with each solar cell producing 5 W of power (a combined 30 W of power).

The DC energy produced by the solar cells 122a can be used to power one or more components of the sensing module 180. In some embodiments, the solar cells 122a can directly provide power to the sensing module. In such embodiments, if the solar cells 122a stop producing energy (e.g., due to lack of sunlight or damage), the energy storage device 122b can act as a backup power source. Alternatively, the energy storage device 122b can store at least some or all of the DC energy produced by the solar cells 122a and, in turn, can provide power to the sensing module. For example, the solar cells 122a can charge the energy storage device 122b which in turn provides power to the sensing module. Alternatively, the energy storage device 122b can store some energy produced by the solar cells 122a and can act as a backup (e.g., during peak operation, or during the absence of sunlight) to power the sensing module 180.

The energy storage device 122b can be any suitable energy storage device, accumulator, and/or the like. In some embodiments, the energy storage device 122b can be a mechanical energy storage device such as flywheel configured to store kinetic energy (e.g., rotational energy) that can be discharged as electric energy. In some embodiments, the energy storage device 122b can be a battery (e.g., a lithium battery). In some embodiments, the energy storage device 122b can store, produce, and/or output any suitable range of power.

The power source 122 can also power the controller 126, the telemetry unit 124, and/or any other suitable component. In some embodiments, the telemetry unit 124 can provide information and/or data associated with the body of water (e.g., ocean), the local and/or forecasted weather, the cultivation apparatus 102, a deployment 101 of any number of cultivation apparatus 102 (FIG. 1D), etc. In some embodiments, the telemetry unit 124 can include one or more sensors and/or devices (e.g., modems, antennas, etc.) that receive data and/or sense and collect data relating to the ocean. Additionally or alternatively, telemetry unit 124 can receive satellite data from one or more satellites (e.g., communication satellites, global navigation satellite system (GNSS) satellites, etc.). In some embodiments, the ocean data and/or the satellite data can include measurements such as ocean surface temperatures, atmospheric temperature and humidity, salinity of the water, color of the water, spectral reflection of the water, nutrient content, alkalinity, nitrogen content, water depth, wave sizes, wave periods, tide information, current direction, current speed, windage, relative position of the cultivation apparatus 102, dispersion (e.g., trajectory) of the cultivation apparatus 102, and/or the like.

In some embodiments, ocean data and/or satellite data can include data obtained from geostationary and/or polar-orbiting meteorological spacecraft. Geostationary and polar-orbiting satellites can provide data that are collected by ground stations. In some embodiments, software onboard the telemetry unit 114 may employ strategies to minimize the usage of costly and power consuming satellite telemetry. These strategies may involve data compression. They may involve data subset selection. They may involve the use of machine learning models to subsample or summarize the data to be transmitted as further described below. As such, it may be desirable to verify the data from the telemetry unit 114 (e.g., by comparing the data to corresponding sensor data from the sensing module 180). In some embodiments, ocean data and/or satellite data from the telemetry unit 114 can be calibrated with ground truthing and used to quantify biomass production, biomass yield, and/or capacity for carbon capture. For example, surface or subsurface conditions (e.g., ocean surface temperature) can be calibrated with temperature measurements from temperature sensors (e.g., temperature sensor included in the sensing module 180) on a cultivation apparatus 102 to determine variances therebetween. In some instances, the data from the telemetry unit 114 (e.g., temperature data) can be smoothed and/or otherwise fit using corresponding data from the sensing module 180. Knowing a variance between the data collected by the telemetry unit 114 and the data collected by the sensing module 180, for example, can increase an accuracy associated with calculations and/or predictions that are made based on that data. In some instances, calibrating and/or verifying the data can allow inferences to be made associated with the trajectory and/or dispersion of the cultivation apparatus 102, as described, for example, in the '681 application.

In some implementations, the telemetry unit 124 (or other component such as the controller 126) can execute one or more software tools, programs, routines, etc. for integrating geographical survey data (e.g., the ocean data and/or satellite data representing temperature, salinity, chemical composition of seawater, chemical composition of atmosphere, ocean currents, etc.) from a variety of inputs such as, for example, satellite(s), in situ measurements (e.g., from the sensing module 180), machine learning or other model-based estimates, and/or the like. In some implementations, such data can be overlayed and/or otherwise aggregated into layers. In some instances, the layers could be representations of primary and/or direct data (e.g., measurements, raw data output from a sensor, etc.). In some instances, the layers could be summarizations of other layers (e.g., temporal averages, spatial averages, etc.). In some instances, the layers could be binary filters on or of one or more other layers (e.g., a criterion is True or satisfied if temperature>a threshold temperature. In some instances, the binary filters can filter based on any number of variables (e.g., a criterion is True if temperature>a threshold temperature AND salinity within a defined range).

In some embodiments, the telemetry unit 124 can include, but is not limited to, a global positioning system (GPS) device (not shown in FIG. 1B), an antenna 124a, a satellite modem 124b, and a compute device 124c. The telemetry unit 124 can obtain satellite data from one or more communication satellites and the geographic location of the cultivation apparatus 102 from global navigation satellite system (GNSS) satellites. For example, the antenna 124a can receive satellite signals transmitted from the one or more communication satellites and GPS radio signals transmitted by the GNSS satellites. Similarly stated, the antenna 124a can be a dual band antenna configured to receive both satellite signals and GPS radio signals. In some embodiments, the antenna 124a can be disposed on an external surface (e.g., outside) of the housing 121. Alternatively, the antenna 124a can be integrated with the housing 121 such that only a portion of the antenna 124a (e.g., the head of the antenna) is on the external surface of the housing 121. More specifically, the antenna 124a can be integrated with the housing 121 such that one end of the antenna 124a is positioned within (e.g., internal to) the housing 121. The antenna 124a can run from inside the housing 121 through the top surface of the housing 121 such that the opposite end of the antenna 124a (e.g., head of the antenna) is disposed on the external surface of the housing 121.

The satellite modem 124b can transform the satellite signals received from the communication satellite(s) into a bitstream. In some embodiments, the satellite modem 124b can implement Server Message Block (SMB) protocol to access satellite data from the communication satellites. The satellite modem 124b can be configured to receive short bursts of the satellite data. This can limit the telemetry unit's usage of power to short intervals (e.g., during the short bursts of satellite data). The GPS can track the geographic location of the cultivation apparatus 102 based on the GPS radio signals.

The compute device 124c can process the bitstream from the satellite modem 124b into satellite data and the GPS radio signals into the geographic location of the cultivation apparatus 102. In some known systems, a telemetry unit (e.g., corresponding to the telemetry unit 124) can be a power sink owing to the size of the data packets (e.g., satellite data and GPS data) transferred to the telemetry unit. Similarly stated, in some known uses, a telemetry unit (e.g., functionally similar to the telemetry unit 124) can draw too much power from the power source during data transfers, thereby placing a strain on the power source. To combat this situation, the compute device 124c can restrict the amount of data being transferred by implementing data subset selection. For example, the compute device 124c can implement a stochastic model for sub selecting the satellite data. In some embodiments, the stochastic model can be generated remotely (e.g., at the one or more external device(s), external processor(s), server(s) such as the server 110 shown in FIG. 1D) and can be transmitted to the compute device 124c via one or more networks (e.g., the network 108 shown in FIG. 1D). In some embodiments, the stochastic model can be generated at the controller 126 of the first member 120 and can be transmitted to the compute device 124c. In yet other embodiments, the stochastic model can be generated at the compute device 124c itself.

The stochastic model can be implemented and/or updated at the compute device 124c and can be local to the cultivation apparatus 102. That is, if multiple cultivation apparatuses 102 are deployed in the water body, it may be possible that different compute devices 124c corresponding to different cultivation apparatuses 102 implement and/or update a slightly different stochastic model that is local to that specific cultivation apparatus 102. The compute device 124c can be configured to receive one or more inputs from a remote user (e.g., human operator) and/or any telemetry data from any suitable source. For example, the compute device 124c can be configured to receive inputs from the one or more external device(s), external processor(s), server(s) (e.g., server 110 in FIG. 1D) via one or more networks (e.g., the network 108 in FIG. 1D). These inputs from the remote or external source, device, and/or user can be used to generate the stochastic model and/or update the stochastic model. For example, the inputs can be feedback from the remote or external source, device, and/or user to iteratively improve the stochastic model. In some embodiments, the one or more external device(s), external processor(s), server (s) (e.g., server 110 in FIG. 1D) can push updates to the model (e.g., by updating one or more parameters of the model) remotely via the one or more networks. Implementing the stochastic model can allow and/or enable the telemetry unit 124 to receive a subset of the satellite data and/or the GPS data. For example, the stochastic model can cause the telemetry unit 124 to receive the subset of satellite data and/or GPS data with highest value, that is the most accurate, and/or that is most useful. In this manner, instead of receiving a large data packet(s), the telemetry unit 124 receives and processes a subset of the data. This can help conserve power, thereby increasing longevity of the power source 122. The compute device 124c can be any suitable compute device 124c including at least one processor. For example, the compute device 124c can be a single-board computer (e.g., Raspberry Pi™) built on a single board circuit including microprocessor(s), memory, and input/output (I/O) interfaces.

Figure 1C:
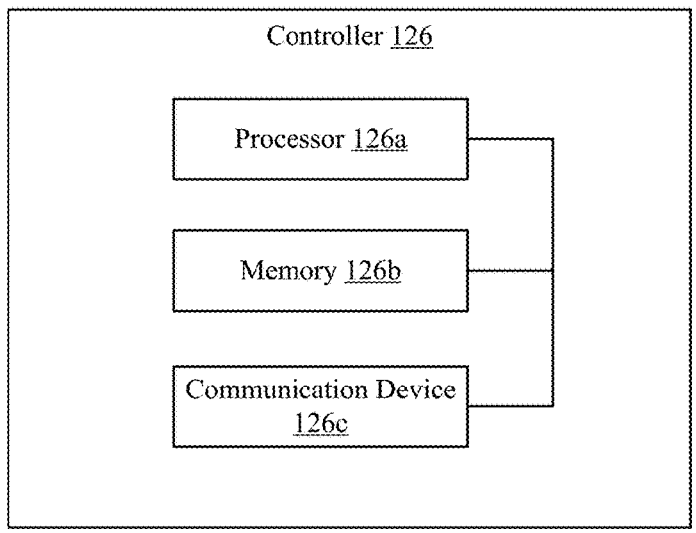
FIG. 1C is a schematic illustration of a controller included in the first member of FIG. 1B.

The controller 126 can be configured to send, receive, and/or process data associated with controlling at least a portion of the cultivation apparatus 102. In some embodiments, the controller 126 can be a single-board computer (e.g., Raspberry Pi™) built on a single board circuit including microprocessor(s), memory, and input/output (I/O) interfaces. In some embodiments, the controller 126 can include at least one or more processors 126a, one or more memory 126b, and a communication interface 126c, as shown in FIG. 1C. The processor(s) 126a can be configured to perform various tasks such as data management, data analysis (e.g., sensor data and/or satellite data), signal and image processing, sensor interfacing, controlling solar cells (e.g., solar cells 122a), controlling power source (e.g., power source 122), and/or the like. The processor(s) 126a may be any suitable processing device configured to run and/or execute a set of instructions or code, and may include one or more data processors, image processors, graphics processing units, digital signal processors, and/or central processing units. The processor(s) 126a may be, for example, a general purpose processor, microprocessor, microcontroller, a Field Programmable Gate Array (FPGA), an Application Specific Integrated Circuit (ASIC), processor board, and/or the like. The underlying device technologies may be provided in a variety of component types (e.g., metal-oxide semiconductor field-effect transistor (MOSFET) technologies like complementary metal-oxide semiconductor (CMOS), bipolar technologies like generative adversarial network (GAN), polymer technologies (e.g., silicon-conjugated polymer and metal-conjugated polymer-metal structures), mixed analog and digital, and/or the like.

The processor(s) 126a may be configured to run and/or execute application processes and/or other modules, processes and/or functions associated with the system 100 shown in FIGS. 1A-1D. In some embodiments, the processor(s) 126a can run and/or execute application processes and/or other modules. In some variations, the application processes and/or other modules may be software modules, hardware modules, and/or a combination of a hardware and software modules. These processes and/or modules when executed by the processor(s) 126a may be configured to perform a specific task. These specific tasks may collectively enable the controller 126 to control one or more portions of the cultivation apparatus 102. For example, the tasks can include and/or can enable interfacing with the sensing module 180, analyzing sensor data obtained from the sensing module 180 and/or data received from external or remote data sources (e.g., the satellite data and GPS data obtained from the telemetry unit 124) to determine accumulation of target product, control the power source 122 to conserve power, etc. In some implementations, the specific task(s) can be interfacing with an intermediate member, release member, coupling member, etc. to decouple the first member 120 from the second member 140 and/or to otherwise allow the second member 140 to sink. In some instances, a remote device or user can send signal(s) via one or more networks (e.g., the network 108 shown in FIG. 1D) indicative of or representing instructions to cause the second member 140 to sink. That is to say, the processor 126a of the controller can perform one or more processes to actively sink the second member 140 in response to an instruction or input from a remote user and/or device. In some instances, such a signal can be received, for example, by the telemetry unit 124 and/or directly by the controller 126 (e.g., via the communication interface 126c).

In some embodiments, the memory 126b is configured to store data and/or information associated with the system 100, the cultivation apparatus 102, and/or components thereof. The memory 126b can be any suitable memory device(s) configured to store data, information, computer code or instructions (such as those described above), and/or the like. In some embodiments, the memory 126b can be and/or can include one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some embodiments, the memory 126b can store instructions to cause the processor 126a to execute modules, processes, and/or functions associated with operating and/or controlling the system 100, the cultivation apparatus 102, and/or components thereof.

Figure 1D:
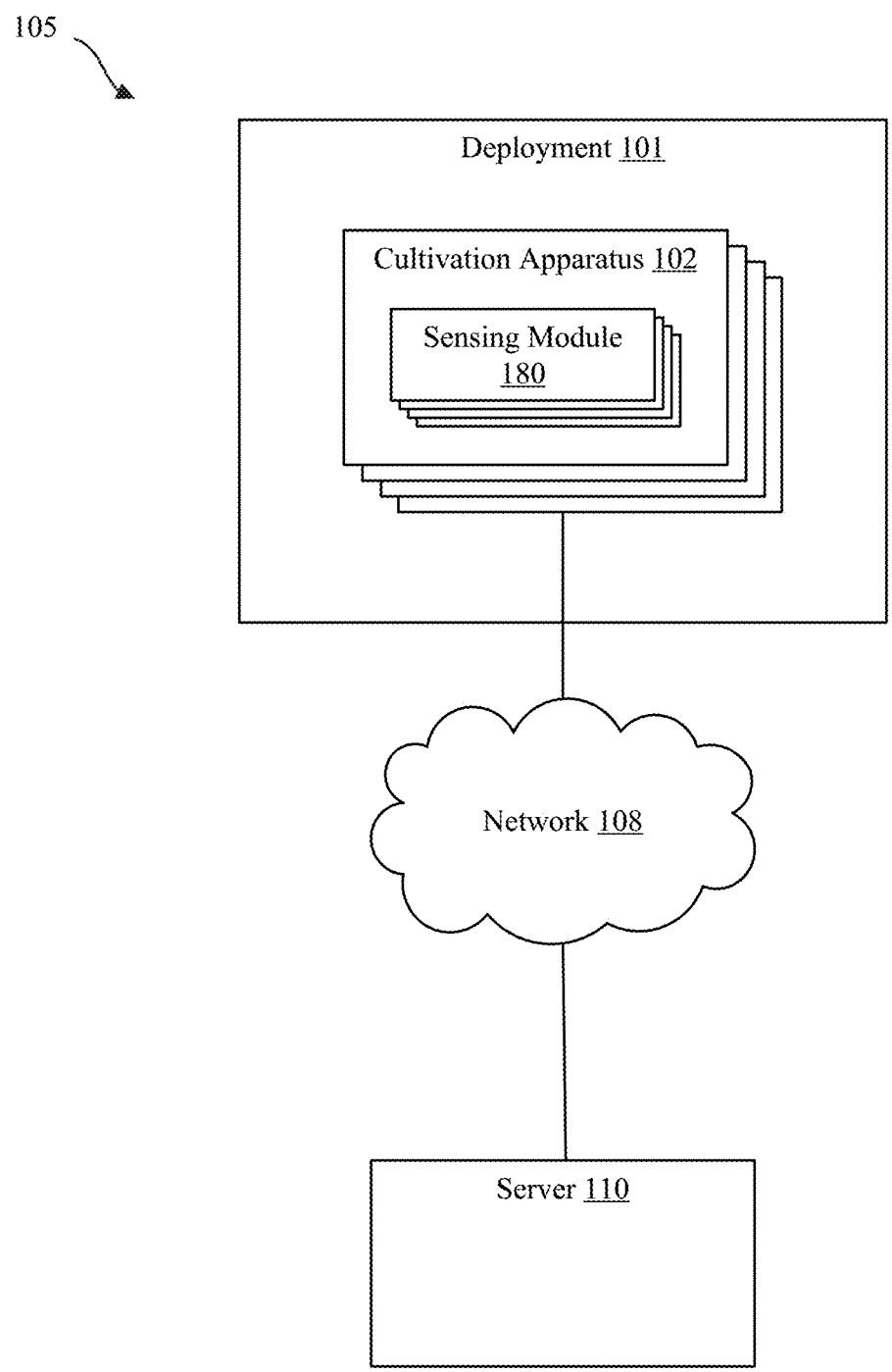
FIG. 1D is a schematic illustration of at least a portion of the system of FIGS. 1A-1C and shown including a deployment of one or more cultivation apparatuses (FIG. 1A) in communication with a server and/or other cultivation apparatuses.

The communication device 126c can be any suitable device(s) and/or interface(s) that can communicate with one or more networks such as the network 108 shown in FIG. 1D (e.g., any of the devices, sensors, and/or data sources described above, and/or any combination or part thereof). Moreover, the communication device 126c can include one or more wired and/or wireless interfaces, such as, for example, Ethernet interfaces, optical carrier (OC) interfaces, and/or asynchronous transfer mode (ATM) interfaces. In some embodiments, the communication device 126c can be, for example, a network interface card and/or the like that can include at least an Ethernet port and/or a wireless radio configured to wirelessly communicate via any suitable communication protocol or combination of protocols (e.g., a WiFi®, a Bluetooth Zigbee, Z-Wave, Matter, Thread, etc.). In some embodiments, the communications device 126c can include one or more satellite antenna (e.g., the antenna 124a). In some embodiments, the communications device 126c can be configured to read one or more characteristics relevant to the target product, transmit signals representative of the cultivation apparatus, and/or the target product characteristics to one or more external devices (e.g., sensing module 180, server 110 in FIG. 1D, etc.), receive from one or more external devices (e.g., sensing module 180, server 110 in FIG. 1D, etc.) signals operable to control the sensing module 180, and/or the like.

In some embodiments, the controller 126 can be configured to read, store, and broadcast sensor data (e.g., sensor data obtained from sensing module 180). The controller 126 can use the sensor data to monitor and/or determine at least one characteristic (e.g., target product growth, quantified mass production, mass yield, carbon capture and/or sequestration rates, quantities, or capacities) representative of target product accumulation. In some embodiments, controller 126 can be configured to control the power source 122. For example, controller 126 can be configured to sequence power between the telemetry unit 124, sensing module 180, and the controller 126 itself. Similarly stated, the controller 126 can be configured to control the power source 122 such that the power source 122 provides power to the telemetry unit 124, sensing module 180, and the controller 126 one at a time and/or in a predetermined sequence having little to no parallelization. This can prevent multiple components from drawing power from the power source 122 at the same time, thereby eliminating and/or reducing power outages. In some embodiments, when the power is scarce (e.g., power source 122 is running low), the controller 126 can be configured to control the power source 122 so as to prioritize operation of various components. For example, if the controller has already obtained sensor data from the sensing module 180, in the event of power scarcity, the controller 126 can prioritize its own operation so that the sensor data is analyzed before additional sensor data is obtained from the sensing module 180.

In some implementations, the electronics (e.g., power source 122, telemetry unit 124, and controller 126) in the first member 120 can be turned on using an external magnet. For instance, a magnetic dongle can be used to turn on an electrical switch such as a reed switch. When magnetic field is applied to the reed switch (e.g., using the external magnet), the reed switch can transition from a closed configuration to an open configuration. This in turn can turn on the electronics included in the first member 120. The controller 126 can be configured to monitor the reed switch and detect changes to the configuration based on the presence of the external magnet.

As described above, the first member 120 of a cultivation apparatus 102 can receive, transmit, and analyze data from one or more of other cultivation apparatuses and/or from one or more external device(s), external processor(s), server(s) via a network. FIG. 1D, for example, is a schematic illustration of at least a portion of the system 100 including a deployment 101 of multiple cultivation apparatuses 102 in communication with the one or more external device(s), external processor(s), server(s), etc. (e.g., server 110) and/or other cultivation apparatuses 102 via the network 108. In some embodiments, the deployment 101 can be substantially similar to the deployment described in the '315 patent and/or the '681 application (incorporated by reference above).

The deployment 101 can be made up of any number cultivation apparatus 102. For instance, deployment 101 can include and/or can be an assembly of several cultivation apparatus 102. In some embodiments, a deployment 101 can include and/or can be an assembly of ten(s) of cultivation apparatus 102. In some embodiments, a deployment 101 can include and/or can be an assembly of hundred(s) of cultivation apparatus 102. In some embodiments, a deployment 101 can include and/or can be an assembly of thousand(s) of cultivation apparatus 102. In some embodiments, a deployment 101 can include and/or can be an assembly of ten(s) of thousands of cultivation apparatus 102. In some embodiments, a deployment 101 can include and/or can be an assembly of hundred(s) of thousands of cultivation apparatus 102. In some embodiments, a deployment 101 can include and/or can be an assembly of million(s) of cultivation apparatus 102. In some embodiments, a deployment 101 can include and/or can be an assembly of more than a billion cultivation apparatus 102.

Any of the cultivation apparatus 102 in the deployment 101 can transmit data and/or receive data from the server 110 and/or other remote or external devices via the network 108. In addition, any of the cultivation apparatuses 102 of the deployment 101 can transmit data and/or receive data from at least another cultivation apparatus 102 of the deployment 101 via the network 108. The network 108 can be, for example, a digital telecommunication network including any number of servers (e.g., server 110) and/or other devices. The network 108 can be implemented as one or more wired and/or wireless communication networks that can allow the server 110, the cultivation apparatuses 102, the sensing modules 180, and/or any other devices to send and/or receive data and to share resources such as, for example, data storage and/or computing power. The wired or wireless communication networks between server 110 and/or the cultivation apparatuses 102 and/or the sensing modules 180 can include one or more communication channels, for example, a radio frequency (RF) communication channel(s), a fiber optic communication channel(s), an electronic communication channel(s), and/or the like. The network 108 can be and/or include, for example, the Internet, an intranet, a local area network (LAN), virtual local area network (VLAN), and/or the like or combinations thereof.

In some embodiments, any of the components housed in the first member 120 can be equipped to communicate with the components housed in other first members via the network 108 using wireless network technologies such as low-power wide-area network modulation technique (LoRa), Zigbee, Z-Wave, Matter, Thread, etc. In some embodiments, any of the components of the cultivation apparatuses 102 included in the deployment 101 can communicate via the network 108, which can be configured using any suitable network topologies such as, for example, a bus topology, a star topology, a tree topology, a linear topology, a ring topology, a mesh topology, a hyper topology, and/or any other types of network topologies or combinations thereof. For example, in some embodiments, any of the components housed in the first members 120 of any number of cultivation apparatuses 102 included in the deployment 101 can form a mesh network topology (e.g., a portion of the network 108 can be and/or can be implemented as a mesh network). For example, a first member 120 in the mesh network topology can be configured to broadcast sensor data, satellite data, GPS data, and/or any suitable output generated by the controller 126, telemetry unit 124, and/or any other component housed in the first member 120 of the cultivation apparatus 102 to any suitable component housed in a first member of another cultivation apparatus in the mesh network topology. Similarly, any of the components housed in the first member 120 can be configured to receive and/or read sensor data, satellite data, GPS data, and/or other output transmitted by components of one or more other cultivation apparatus in the mesh network topology. Sharing data between components housed in the first members of different cultivation apparatuses in the deployment 101 can add to the reliability of the mesh network. In some embodiments, the first member (or any of the components therein) of at least one cultivation apparatus in the deployment 101 can act as a network hub for any suitable network topology. The hub can receive, directly or indirectly, data from all other first members in the network topology and can transmit this data to any suitable remote or external device (e.g., the server 110) and/or can perform any suitable function or process on the data locally.

In some embodiments, the server 110 and/or any other remote or external devices can be substantially similar to the server and/or external devices described in the '681 application (incorporated by reference above). In some embodiments, data from any of the cultivation apparatuses 102 can be transmitted to the server 110, directly or indirectly, via the network 108 (e.g., at least a portion of which can be implemented as a mesh network or the like). The server 110 can analyze the received data to determine, calculate, model, predict, estimate, evaluate, etc. target product growth, quantify mass production, and/or mass yield. In some embodiments, the server 110 can include one or more servers and/or one or more processors running on a cloud platform (e.g., Microsoft Azure®, Amazon® web services, IBM® cloud computing, etc.). Generally, the server 110 (e.g., including a CPU) described herein may process data and/or other signals to quantify, verify, predict, and/or infer characteristics relating to the target product, cultivation apparatus, water body, deployment and/or the like for the purposes of carbon sequestration. The server 110 may be configured to receive, process, compile, compute, store, access, read, write, and/or transmit data and/or other signals. In some embodiments, the server 110 can be configured to access or receive data and/or other signals from one or more of a sensor(s) and a storage medium(s) (e.g., memory, flash drive, memory card). In some embodiments, the server 110 can include at least a processor, a memory, and a communications device. In some embodiments, the server 110 can be configured to perform processes and/or execute programs, algorithms, models, and/or the like associated with determining target product accumulation (and/or erosion) and, for example, a corresponding capacity for capturing and sequestering carbon dioxide.

Accordingly, as described above, the arrangement of the cultivation apparatus 102 and/or the components thereof can allow for the collection and/or analysis of data associated with the growth of any number of target products included in the deployment 101. For example, in some instances, the power source 122 (FIG. 1B) included in the first member 120 can include and/or can receive power from the one or more solar cells 122a (FIG. 1B) and can transmit and/or provide at least a portion of the power to other electronic components of the first member 120 and/or to the sensing module 180. The sensing module 180 can sense and detect characteristics relating to the target product seeded at least on the second member 140 and optionally on the first member 120 of the cultivation apparatus 102. The sensing module 180 can transmit the sensor data to the first member 120 via a network (e.g., network 108 in FIG. 1D) and/or via one or more cables or other interfaces included in the support structure (as further described below). The controller 126 (FIG. 1B) included in the first member 120 can analyze the sensor data. Additionally or alternatively, the controller 126 can analyze satellite data and/or ocean data and/or any other remote data received via the telemetry unit 124. The controller 126 can monitor the accumulation of the target product based on the sensor data, ocean data, satellite data, etc. The controller 126 can also receive data from any number of other cultivation apparatus included in the deployment 101 (e.g., via a mesh network or other suitable network topology). The controller 126 and/or any other components of the first member 120 can also transmit data via the network 108 to the server 110 and/or any other remote or external device for additional analysis, processing, etc. The controller 126 can also be remotely operated and/or controlled from one or more external device(s), external processor(s), server(s) (e.g., the server 110 in FIG. 1D) via the network 108. As such, the data associated with the cultivation apparatuses 102 included in the deployment 101, environmental data, and/or any other data can be collected, aggregated, and/or processed, which in turn, can be used to determine, estimate, model, and/or predict an amount of carbon that is or that can be sequestered when the target product (e.g., macroalgae) attached to the cultivation apparatuses 102 of the deployment 101 is allowed to sink to the bottom or floor of the body of water (e.g., the ocean floor).

Figure 2A:
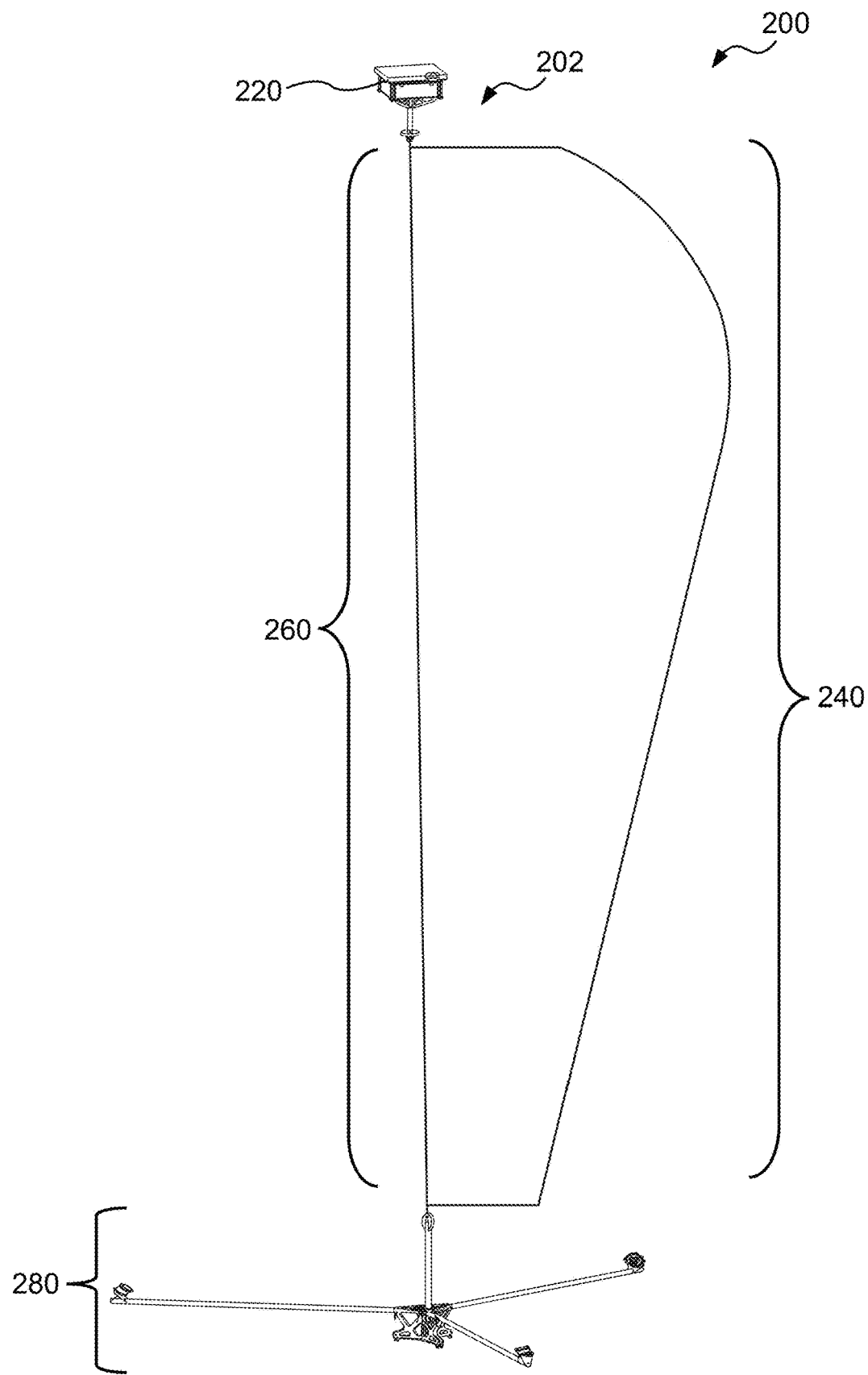
FIGS. 2A-2G are various views of at least a portion of a system for monitoring target product accumulation, according to an embodiment.

FIGS. 2A-2G illustrate at least a portion of a system 200 (e.g., structurally and/or functionally similar to system 100 in FIG. 1A) for monitoring target product accumulation, according to an embodiment. As shown in FIG. 2A, the system 200 can include a cultivation apparatus 202 having a first member 220 (e.g., structurally and/or functionally similar to first member 120 in FIG. 1A), a second member 240 (e.g., structurally and/or functionally similar to second member 240 in FIG. 1A), a support structure 260, and a sensing module 280 (e.g., structurally and/or functionally similar to sensing module 180 in FIG. 1A).

The first member 220 can be configured to monitor the accumulation of the target product and provide buoyancy to various components of the system 200. The first member 220 can include a housing (e.g., similar to the housing 121 in FIG. 1B) enclosing a power source, a telemetry unit, and a controller (e.g., similar to the power source 122, the telemetry unit 124, and the controller 126, respectively, described with reference to FIG. 1B). The power source can be configured to provide power to the sensing module 280 configured to obtain sensor data that can be representative of one or more characteristics associated with accumulation of target product. The telemetry unit can be configured to collect and transmit satellite data. The controller can be configured to analyze the satellite data and/or the sensor data obtained from the sensing module and quantify the characteristics and/or the accumulation of the target product. The housing can be a sealed waterproof enclosure protecting the components in the first member 220. The controller can also be configured to control the power source to prioritize providing power based on the operations of the system 200. In some embodiments, the controller and/or the telemetry unit can be configured to implement a stochastic model to select a subset of data for transfer and analysis so as to limit the utilization of power.

In some embodiments, the first member 220 can include an attachment mechanism that can at least temporarily mechanically couple the first member 220 to the support structure 260 and/or the second member 240. For example, a distal end portion of the first member 220 can include loops, rings, hooks, etc. The support structure 260 can be disposed directly below and/or can extend from the first member 220 such that the attachment mechanism couples the support structure to the first member 220. For example, the support structure 260 can be coupled to, integrated with, or otherwise attached to the first member 240 vertically below (e.g., at the distal end) the first member 240. In some embodiments, the support structure 260 can be of any suitable shape (e.g., tubular shaped). In some embodiments, the support structure 260 can be a cable that is designed to maintain flexibility in harsh environment. For example, the support structure 260 can include a high-grade polyurethane cable that is designed for underwater use. In some embodiments, the support structure 260 can be compact and can have tighter bends such that the support structure is flexible yet can withstand ocean currents without or substantially without distorting. In some embodiments, at least a portion of the support structure 260 can be surrounded by materials that facilitate target product growth. In particular, the support structure 260 can be at least temporarily coupled to the second member 240 via a release member, link (e.g., chain, etc.), and/or the like. The portion of the support structure 260 adjacent to, overlapping with, and/or closer to the second member 240 can be surrounded by materials that facilitate target product growth such as any suitable material used with respect to the second member 240.

The support structure 260 can include one or more wires/cords to transmit power from the first member 220 to the sensing module 280 and/or to communicate data between the first member 220 and the sensing module 280. For example, the support structure 260 can include a first wire/cord to transmit power from the first member 220 to the sensing module 280 and a second wire/cord to communicate data between the first member 220 and the sensing module 280. In other embodiments, the support structure 260 can include a single wire/cord that provides both power and data transmission such as, for example, Power over Ethernet or the like. The wires/cords can be connected to the first member 220 and/or the sensing module 280 via connectors. For example, a first connector included at a proximal section of the support structure 260 can connect one or more wire/cords to the first member 220. A second connector included at a distal section of the support structure 260 can connect one or more wires/cords to the sensing module 280. These connectors can be configured to withstand harsh ocean conditions.

In some embodiments, one or more wires/cords included in the support structure 260 can include a sensor detection signal line. For example, the first wire/cord to transmit power and/or the second wire/cord to communicate data can additionally function as a sensor detection signal line. Alternatively, the support structure 260 can include a separate wire/cord (e.g., a third wire/cord) to function as the sensor detection signal line. The sensor detection signal line can enable the first member 260 (e.g., a controller such as controller 126 in FIG. 1A included in the first member) to determine whether the sensing module 280 is coupled to the support structure 260. Additionally or alternatively, the sensor detection signal line can enable the first member 220 to determine whether there is an issue with the connection between the first member 220 and the sensing module 280.

The second member 240 configured to cultivate or accumulate the target product can be coupled (at least temporarily) to the first member 220 and/or the support structure 260 via a release member, link (e.g., chain, etc.), and/or the like. The second member 240 can be positioned such that the second member 240 is parallel to and/or adjacent to the support structure 260. A proximal end of the second member 240 can be coupled to the first member 220 via the attachment mechanism included on the first member 220 (e.g., a chain and/or a link). The sensing module 280 can be positioned at and/or near the distal end of the second member 240.

The sensing module 280 includes and/or is mounted to a frame 282 that is disposed at an end of the support structure 260 such that the sensing module 280 is positioned at or near the distal end of the second member 240. The sensing module 280 and/or frame 282 thereof can be coupled to, attached to, or otherwise integrated with the support structure 260. For example, the frame 282 can be coupled to attached to, or otherwise integrated with the distal end of the support structure 260. Accordingly, the sensing module 280 can be coupled to the first member 220 via the support structure 260. The sensing module 280 can include one or more sensors configured to obtain sensor data relating to the target product. The sensors can be coupled to, attached to, or otherwise integrated with the frame 282 of the sensing module 280. The frame 282 can orient the sensors to the target product such that the sensor can capture data from at least a section of the target product and/or the second member 240.

Figure 2B:
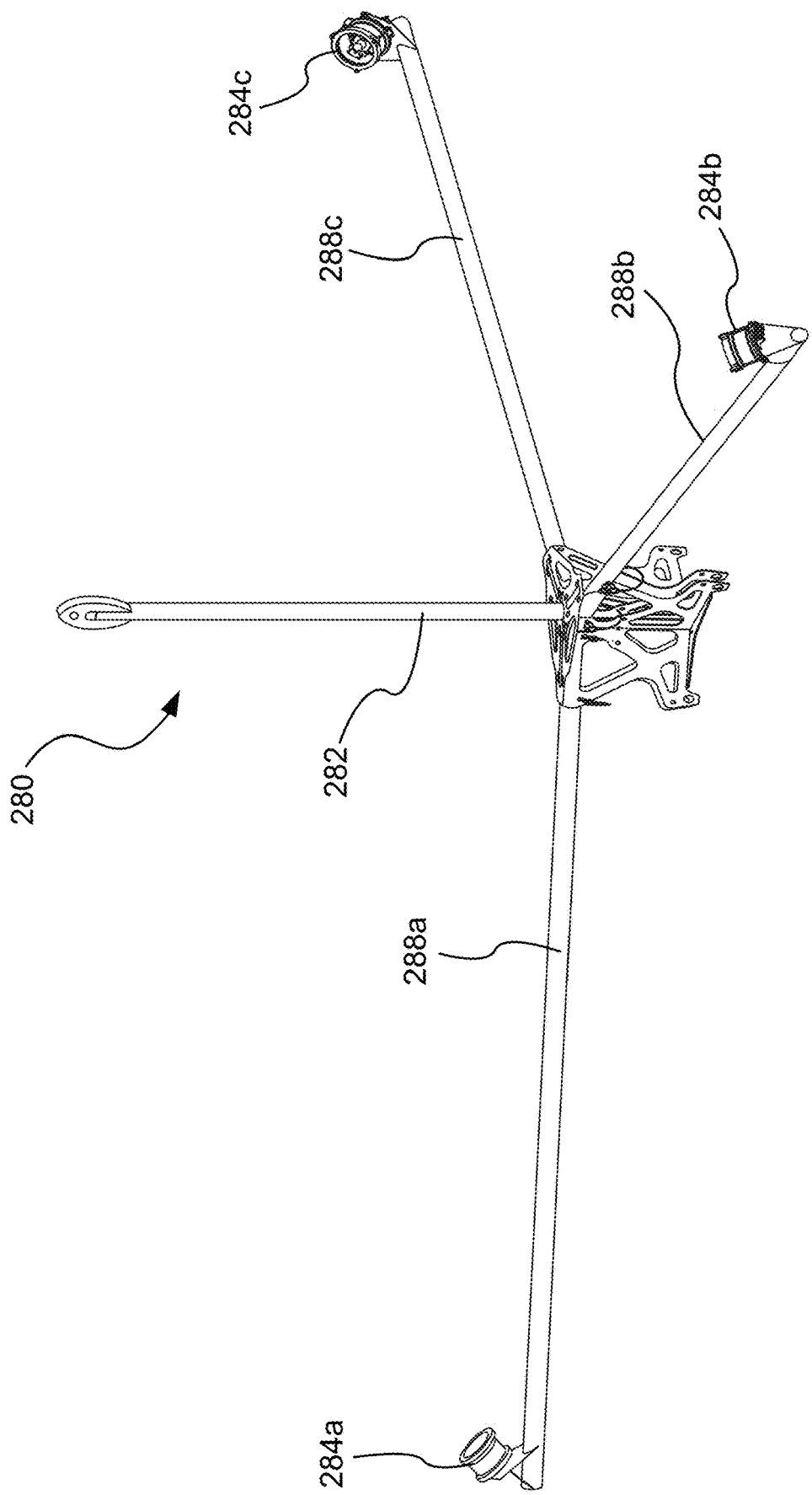

For example, the frame 282 can include one or more arms, each of which is configured to support and/or to be coupled to a sensor. More particularly, as shown in FIG. 2B, the frame 282 can include three arms 288a, 288b, and 288c, each of which is configured to support and/or to be coupled to the sensors 284a, 284b, and 284c, respectively. Although FIG. 2B illustrates three arms 288 and three sensors 284, it should be readily understood that the frame 282 can include any suitable number of arms. Additionally, although FIG. 2B illustrates each arm 288 supporting a single sensor 284, it should be readily understood that each arm 288 of the frame can support more than one sensor 284. For example, it can be possible for arm 288a to support another sensor (not shown in FIGS. 2A-2G) in addition to supporting sensor 284a.

Figure 2C:
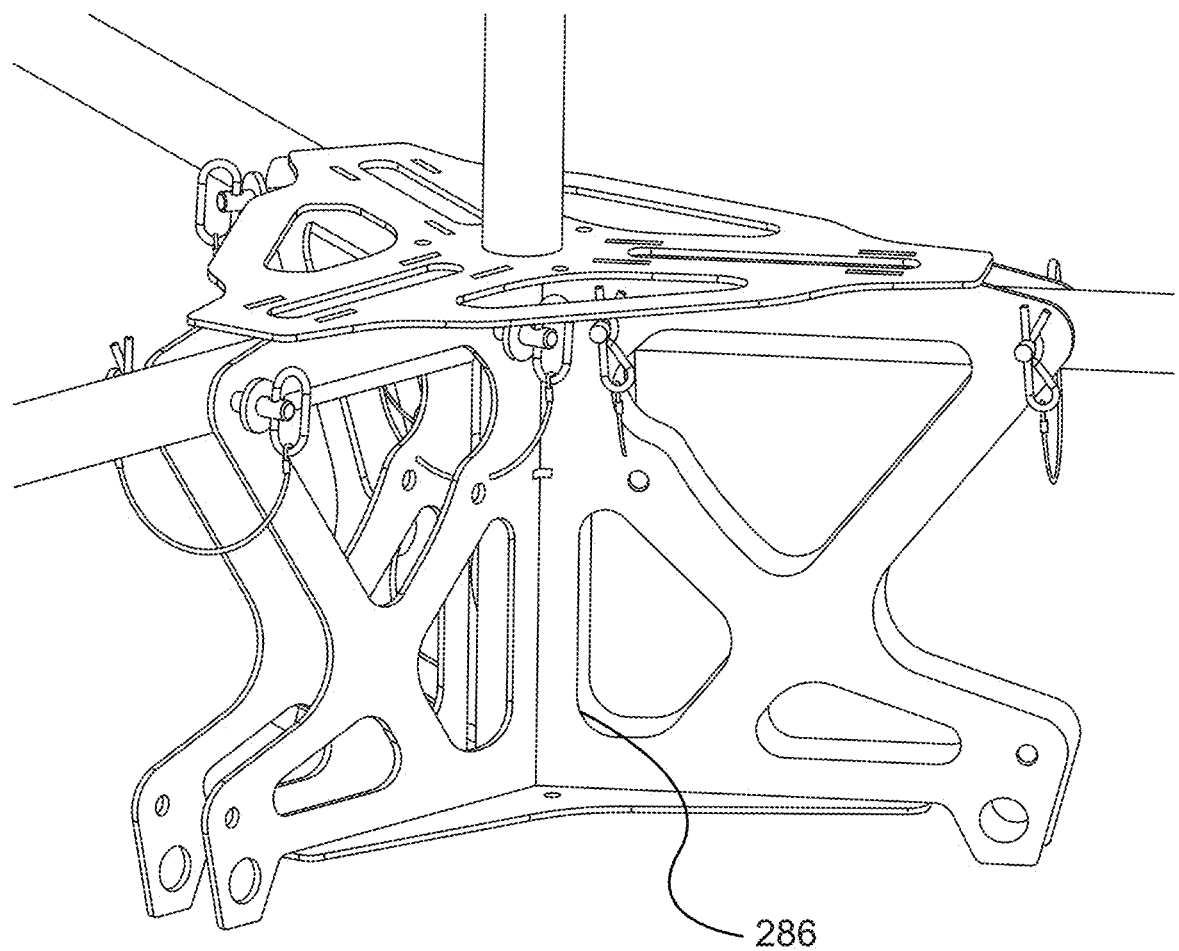

In some embodiments, the frame 282 can be reconfigurable between a collapsed configuration and an extended configuration in which the arms 288a, 288b, and 288c extend in a radial direction outward from the support structure 260. In some implementations, the frame 282 is configured to be in the collapsed and/or folded configuration prior to deployment into the water. For example, as shown in FIG. 2C, the frame 282 can include a central mount 286 to which each arm 288a, 288b, and 288c is coupled. In some embodiments, the central mount 286 can have a first configuration in which the arms 288a, 288b, and 288c are folded (not shown), and a second configuration in which the arms 288a, 288b, and 288c are extended (see e.g., FIGS. 2A-2D). Placing the central mount 286 in the first configuration in which the arms 288a, 288b, and 288c are folded can minimize the storage area for the sensing module 280 before being deployed into the water body. In some implementations, the central mount 286 can be transitioned to the second configuration in which the arms 288a, 288b, and 288c are extended just before and/or upon deployment of the frame into the water body. For example, a remote device such as the server 110 shown in FIG. 1D can remotely control the central mount 286 to extend the arms 288a, 288b, and 288c just before and/or upon deployment of the frame into the water body. Alternatively, the central mount 286 can be transitioned by a human operator to extend the arms 288a, 288b, and 288c, as desired.

Figure 2D:
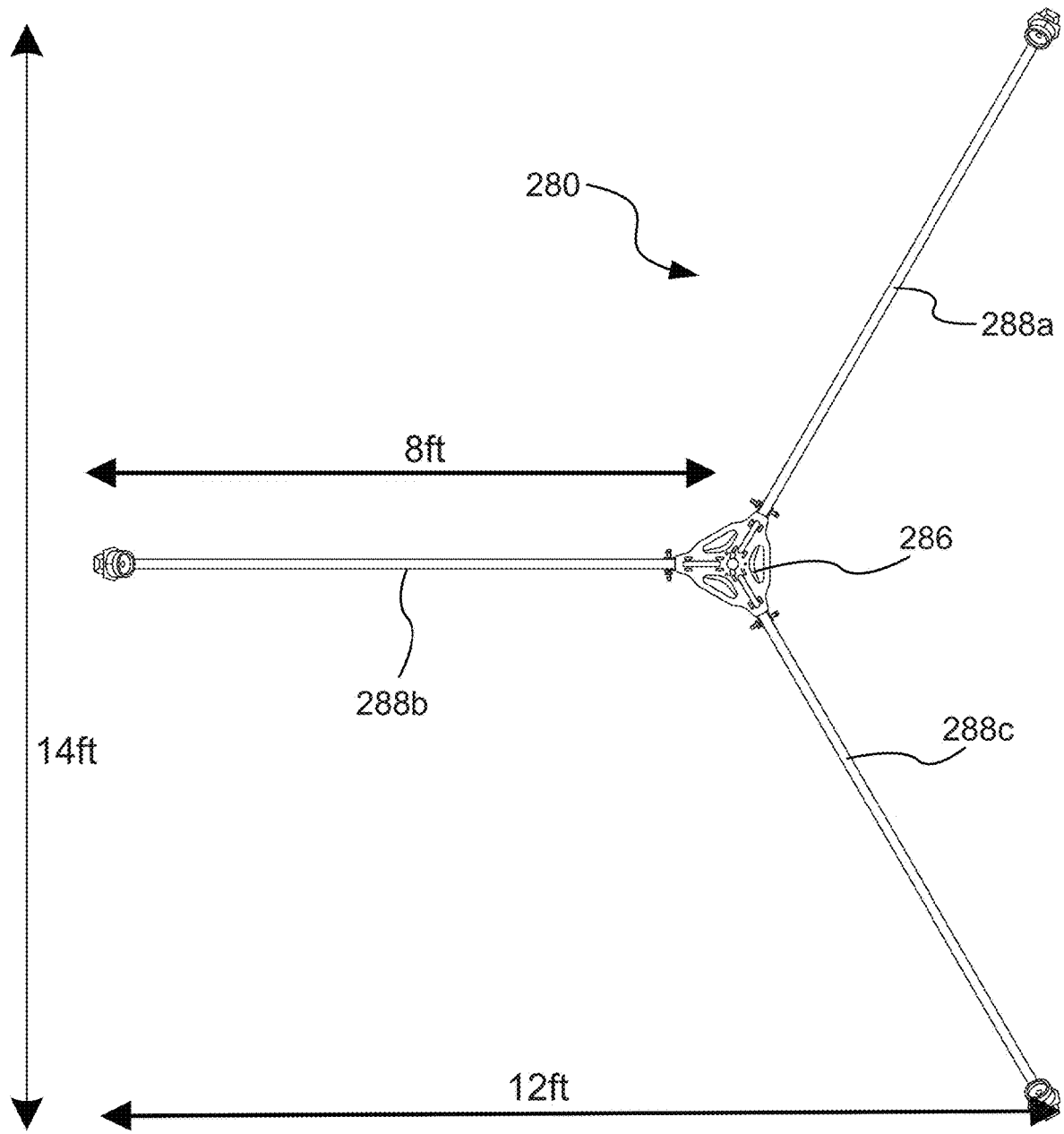

The frame 282 in the extended configuration can be such that the arms 288a, 288b, and 288c position the sensors 284a, 284b, and 284c, respectively, at a desired depth and/or location in the water. For example, the arms 288a, 288b, and 288c be configured to extend in a radial direction from the second member 240 and/or support structure 260 such that the sensors 284a, 284b, and 284c are at a desired depth, desired location, and/or desired orientation relative to the target product to all the sensors 284a, 284b, and 284c to capture sensor data from various sections of the second member 240 and/or the target product. In some embodiments, the length of each extended arm 288a, 288b, and 288c can be about 8 feet (ft), the width of the frame 282 with each arm 288a, 288b, and 288c extended can be about 14 ft, and the length of the frame 282 with each arm 288a, 288b, and 288c extended can be about 12 ft, as shown in FIG. 2D.

In some embodiments, the arms 288a, 288b, and 288c can be pivoted or at least partially collapsed to orient the sensors 284a, 284b, and/or 284c toward a desired portion or section of the second member 240 and/or the target product. For example, the central mount 286 (FIGS. 2C and 2D) can be configured to allow the arms 288a, 288b, and 288c to be pivoted to a desired position. In some implementations, the arms 288a, 288b, and 288c can be pivoted automatically and/or remotely or can be manually pivoted via user intervention.

Figure 2E:
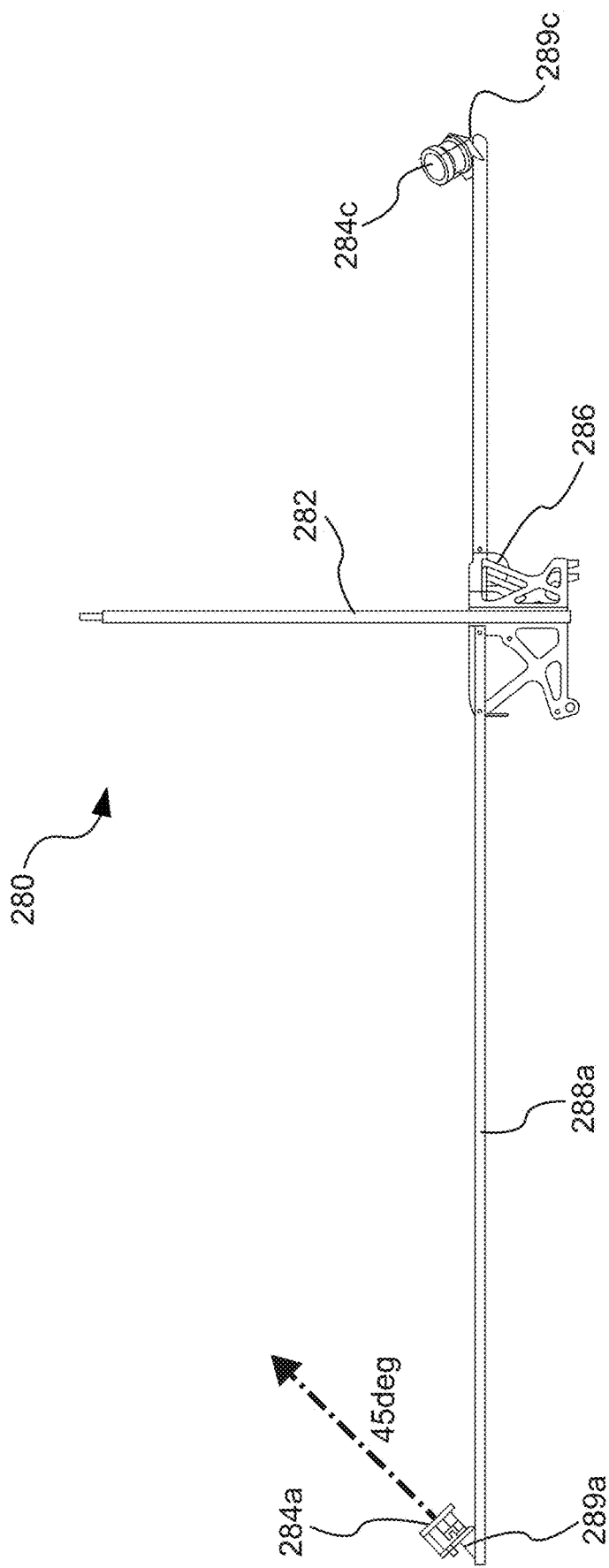
Figure 2F:
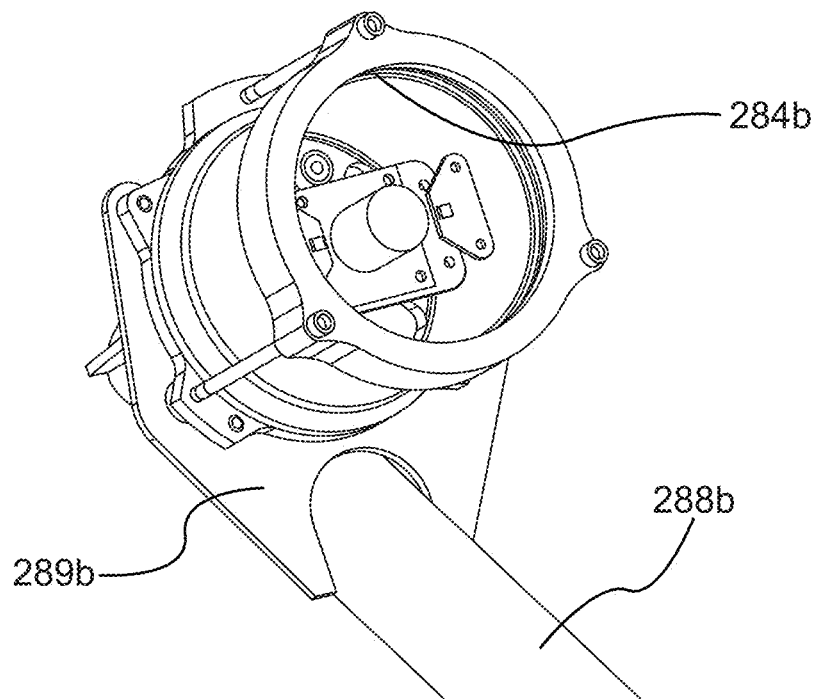
Figure 2G:
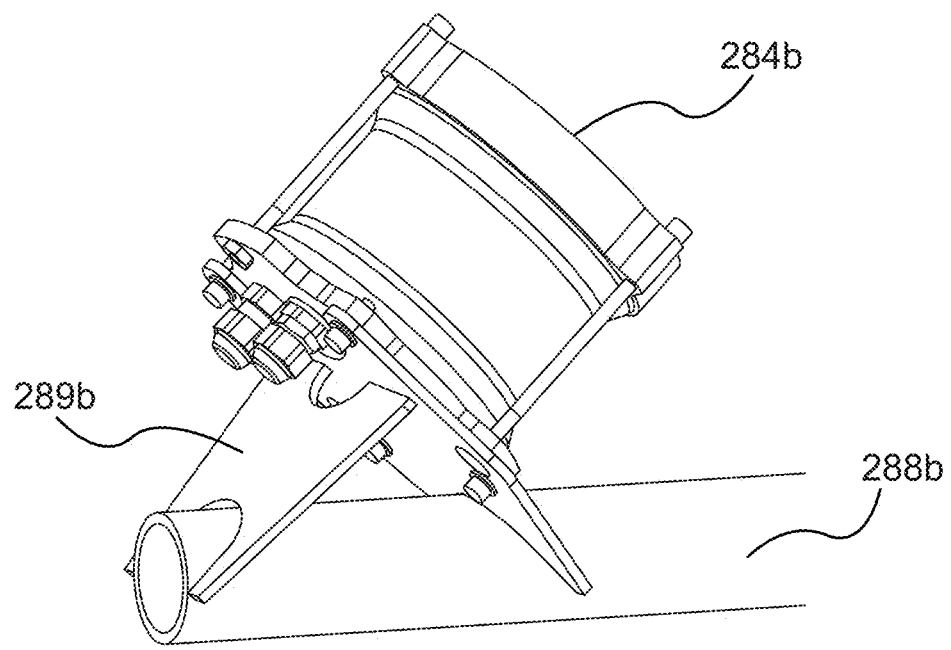

In some embodiments, the mounting of the sensors 284a, 284b, and 284c to the arms 288a, 288b, and 288c can allow for a pivoting, rotating, translating, and/or reorienting of the sensors 284a, 284b, and 284c in addition to the pivoting of the arms 288a, 288b, and 288c as just described. As shown in FIGS. 2E-2G, in some implementations, the sensors 284a, 284b, and 284c can be oriented at 45 degrees with respect to the arms 288a, 288b, and 288c of the frame 282. The sensors 284a, 284b, and 284c, in turn, can then have an angle of orientation (e.g., camera pitch angle if the sensor is a camera) of 45 degrees. Similarly stated, the sensors 284a, 284b, and 284c may be oriented at 45 degrees with respect to the arms 288a, 288b, and 288c, respectively, so that the sensor is oriented at the 45-degree angle towards the second member 240. In this manner, the frame 282 can place and/or can support the sensors 284a, 284b, 284c in the appropriate angle to capture sensor data from various sections of the second member 240.

As shown in FIGS. 2E-2G, the sensors 284a, 284b, and 284c can be coupled to the arms 288a, 288b, and 288c via a coupler 289a, 289b, and 289c, respectively. One end of the couplers 289a, 289b, and 289c can be attached to, coupled to, or otherwise integrated with the corresponding arm 288a, 288b, and 288c and the opposite end of the coupler 289a, 289b, and 289c can be attached to, coupled to, or otherwise integrated with the corresponding sensors 284a, 284b, and 284c. In some embodiments, the couplers 289a, 289b, and 289c can be adjustable, pivotable, rotatable, moveable, and/or otherwise reconfigurable either automatically and/or remotely, or manually via user intervention. For example, the sensors 284a, 284b, and 284c can be configured to be positioned at various angles to capture sensor data from different sections of the second member and/or the target product. For example, in FIG. 2E, the couplers 289a, 289b, and 289c can be positioned at/pivoted to 45 degrees with respect to the arms 288a, 288b, and 288c, respectively, so that the angle of orientation of the sensor 284a, 288b, and 284c, respectively, is 45 degrees with respect to the corresponding arms 288a, 288b, and 288c. The sensors 284a, 284b, and 284c can be configured to capture sensor data from a section of the second member 240 and/or target product that is in the field of view of the sensor 284a, 284b, and 284c (e.g., when the sensors are cameras or image capture devices). In some embodiments, each coupler 289a, 289b, and 289c can be positioned at different angles to orient each sensor 284a, 284b, and 284c of the sensing module 280 at different angles. Alternatively, all couplers 289a, 289b, and 289c can be positioned at the same angle so that the angle of orientation of all the sensors 284a, 284b, and 284c is the same. In yet another alternative embodiment, some couplers 289a, 289b, and 289c can be positioned at a different angle from some other couplers 289a, 289b, and 289c.

Although not shown in FIGS. 2A-2G, in some implementations, the arms 288a, 288b, and 288c can be adjusted, moved, and/or pivoted collectively or independently. Independent control of the arms 288a, 288b, and 288c and/or the sensors 284a, 284b, and 284c can allow sensor data to be collected for different sections of the second member 240 and/or target product. Similarly, while the sensors 284a, 284b, and 284c are shown as being substantially the same, in some embodiments, one or more of the sensors 284a, 284b, and 284c can be different from the others, allowing the collection of data representing different characteristics of the target product and/or environmental conditions. While the sensing module 280 is shown as being coupled at an end of the support structure 260, in other implementations, the sensing module 280 can be coupled to the support structure 260 at any point along its length. Moreover, the system 200 can include multiple sensing modules 280 coupled at various positions along a length of the support structure 260. In some implementations, the sensing module(s) 280 can be movable along the support structure 260.

As such, the arrangement of the system 200 and/or cultivation apparatus 202 can allow the sensing module to collect data at any desired section along the second member 240 and/or target product. Moreover, with the sensing module 280 being electrically and/or electronically connected to the first member 220, the sensor data collected can received, aggregated, processed, analyzed, transmitted, and/or otherwise used by one or more electronic components (e.g., the controller, the telemetry unit, and/or the like), as described in detail above with reference to the first member 120 shown in FIGS. 1A-1C. In some embodiments, the sensing module 280 can include a processor and/or a memory to allow the sensing module 280 to interface with the first member 220. For example, the processor of the sensing module 280 can be configured to receive the sensor data, pre-process the sensor data, and/or analyze the sensor data. In some instances, the processor of the sensing module 280 can extract and/or determine trends and/or measurements relating to growth or accumulation of the target product. The processor can transmit the sensor data to the first member 220 (e.g., via the support structure 260 and/or a network such as the network 108 in FIG. 1D).

Figure 3:
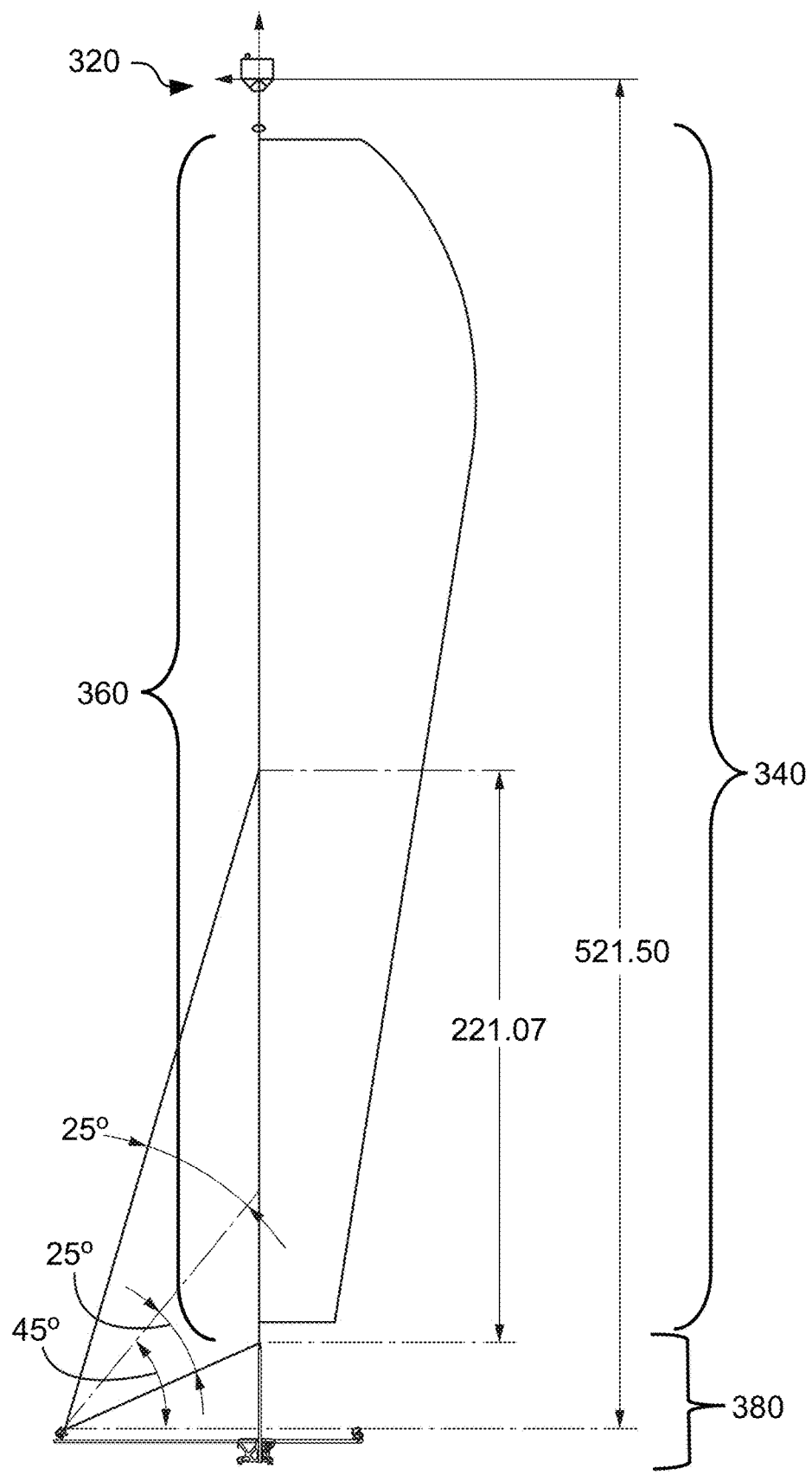
FIG. 3 is an illustration of one or more sensors capturing sensor data from different sections of a second member of a cultivation apparatus, according to an embodiment.

FIG. 3 is an illustration of sensors capturing sensor data from different sections of the second member 340 (e.g., structurally and/or functionally similar to second member 140 in FIG. 1A and/or second member 240 in FIG. 2A), according to an embodiment. As discussed above, the sensing module 380 (e.g., structurally and/or functionally similar to sensing module 180 in FIG. 1A and/or sensing module 280 in FIGS. 2A-2G) can include a frame and one or more sensors. The frame can include arms that extend in a radial direction from the second member 240. The arms can be extended out such that the sensors can capture sensor data from various sections of the second member 340. In particular, the arms can be extended out such that the length of the extended portion of the arms position the sensors at desired locations/depth to capture sensor data from various sections of the second member 340. Additionally or alternatively, the arms can be extended out such that the angle of orientation of the arms with respect to a horizontal axis of a support structure 360 (e.g., structurally and/or functionally similar to support structure 260 in FIG. 2A) position the sensors at desired locations/depth to capture sensor data from various sections of the second member. Each arm can include one or more pivotable supports that can pivot around the arms. The sensors can be coupled to, attached to, or otherwise integrated with the pivotable supports. The pivotable support can position the sensors at a desired angle such that the sensors can capture sensor data from various sections of the second member 240.

In FIG. 3, as a non-limiting example, the length of the support structure 360 and/or the second member 340 is 45 ft. The portion of the second member 340 covered by the sensors to capture the sensor data can depend on the field of view of the sensors, the length of the arm, and the angle of orientation (e.g., camera pitch angle) of the sensors. For example, when a sensor is placed at a 90-degree pitch angle on an extended portion of the arm with a length of zero (e.g., placed directly/vertically below the second member 340), the sensor can get coverage of the section of the second member 340 that is vertically above the sensor. Put differently, when the sensor is placed directly below the second member and oriented vertically upwards towards the second member, the sensor can get coverage of the section of the second member 340 that is vertically above the sensors. However, the section that is further away from the sensor can be blocked by the section that is directly above. More specifically, the section that is not directly above (e.g., towards a side edge of the second member 340, etc.) may be blocked from the field of view of the sensor. Therefore, the length of the extended portion of the arm may have to be greater than zero. In general, a shorter length of the extended portion of the arm can require steeper pitch angles to cover the entire second member 340. In FIG. 3, the sensors have a pitch angle of 45 degrees. These sensors can cover, for example, 18 ft of the second member 340 from the bottom of the second member 340. Similarly stated, these sensors can cover, for example, a height of 18 ft starting from the bottom of the second member.

Figure 4A:
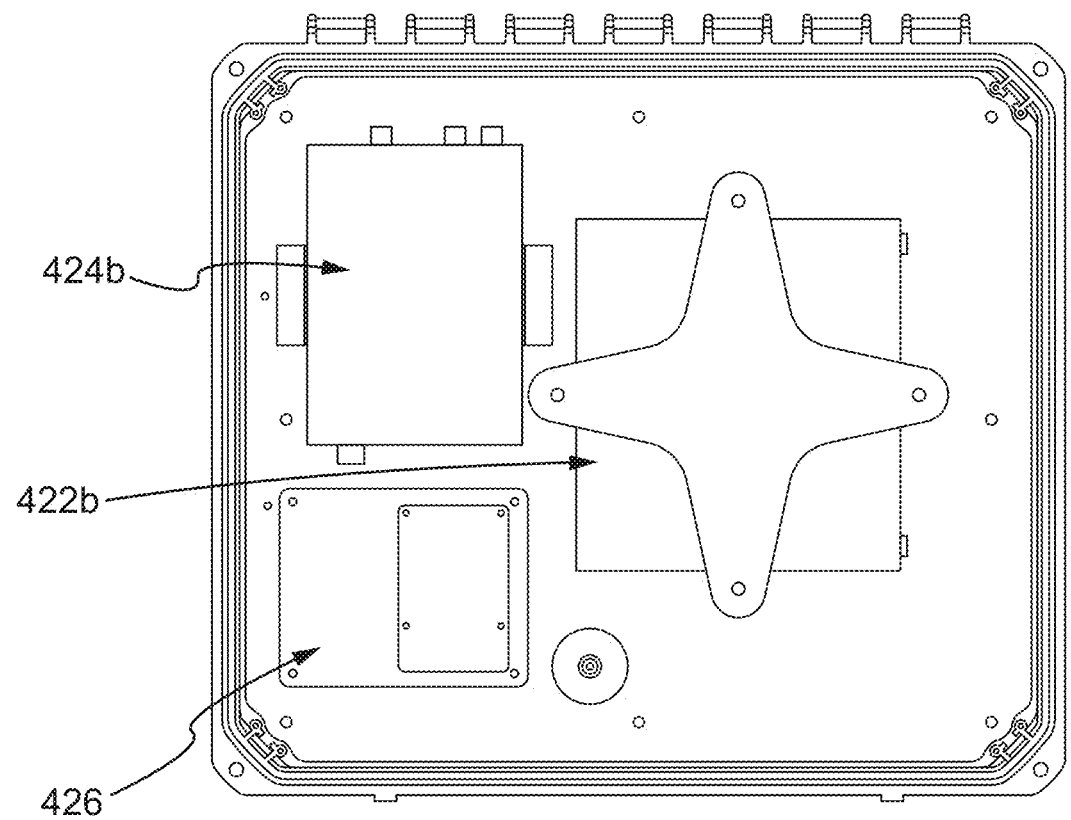
FIGS. 4A and 4B are a top view and a side view, respectively, each illustrating a portion of a first member of a cultivation apparatus and electronic components housed therein, according to an embodiment.

FIG. 4A is a top view of a portion of a first member 420 (e.g., structurally and/or functionally similar to first member 120, 220, and/or 320 described above) that illustrates electronic components housed in the housing of the first member 420, according to an embodiment. As discussed above, the first member 420 can house a power source including an energy storage device 422b (e.g., structurally and/or functionally similar to energy storage device 122b in FIG. 1B), a telemetry unit including a satellite modem 424b (e.g., structurally and/or functionally similar to satellite modem 124b in FIG. 1B), and a controller 426 (e.g., structurally and/or functionally similar to controller 126 in FIG. 1B). In some embodiments, the energy storage device 422b can be a battery. In some embodiments, the energy storage device 422b can be configured to weigh less but store more power. For example, the energy storage device can be a lithium iron phosphate battery such as RELiON RB20. In some embodiments, the RELiON RB20 can generate 256 W of power. The satellite modem 424b can include a mounted satellite terminal that supports iridium communications. For example, the satellite modem 424b can be MCG-10. As discussed above, the satellite modem 424b can support short bursts of data packets. In some embodiments, the satellite modem 424b can receive data packets between about 300 bytes and about 1800 bytes, between about 500 bytes and about 1600 bytes, between about 800 bytes and about 1300 bytes (including all values and subranges therein). In some embodiments, the satellite modem 424b can implement Server Message Block (SMB) protocol to access satellite data from the communication satellites. For example, the SMB protocol can allow the satellite modem to stream about 1 Megabyte of satellite data per hour. The controller 426 can be a single-board computer such as Raspberry Pi™. In some embodiments, the controller 426 may be configured to draw low power in order to operate.

Figure 4B:
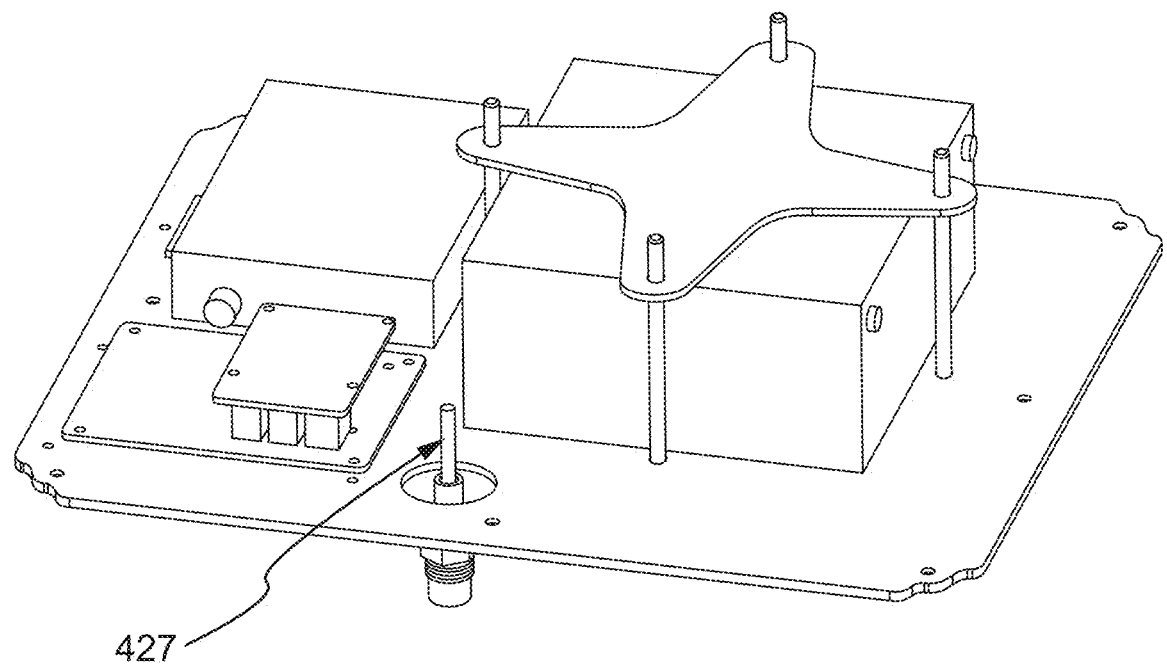

FIG. 4B is a side view of a portion of the first member 420 that illustrates at least some of the electronic components housed in the housing. In addition to the components described in FIG. 4A, the housing may include a connector 427 as seen in FIG. 4B. The connector can connect the antenna 424a through the housing. For example, the connector 427 can mount the antenna 424a through the bottom of the housing such that the head of the antenna is disposed on the top of the housing (e.g., lid of the enclosure).

Figure 5B:
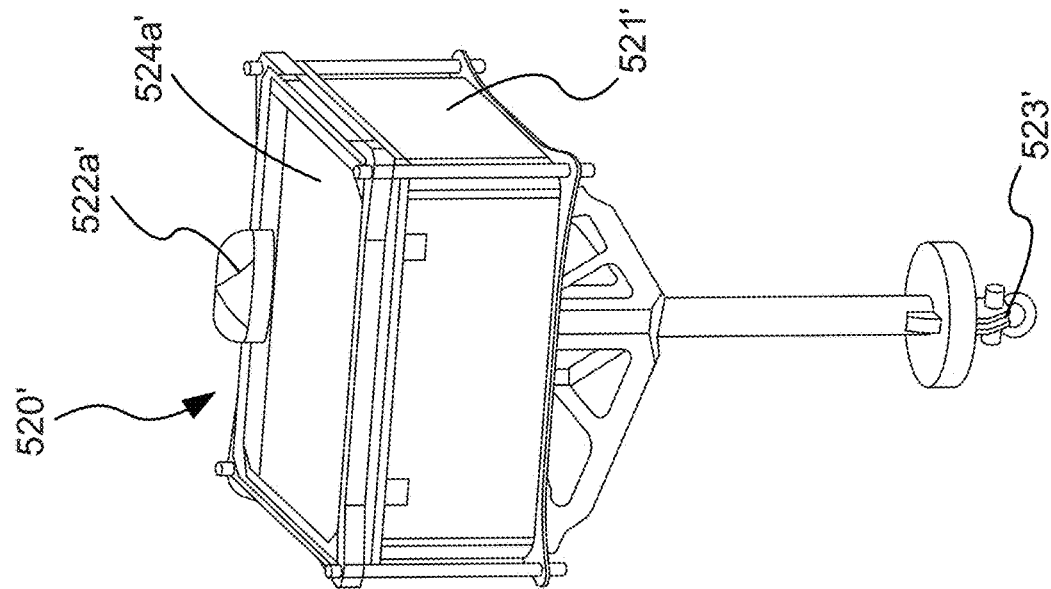
FIGS. 5A and 5B are side perspective views of a first member of a cultivation apparatus, according to a different embodiment.
Figure 5A:
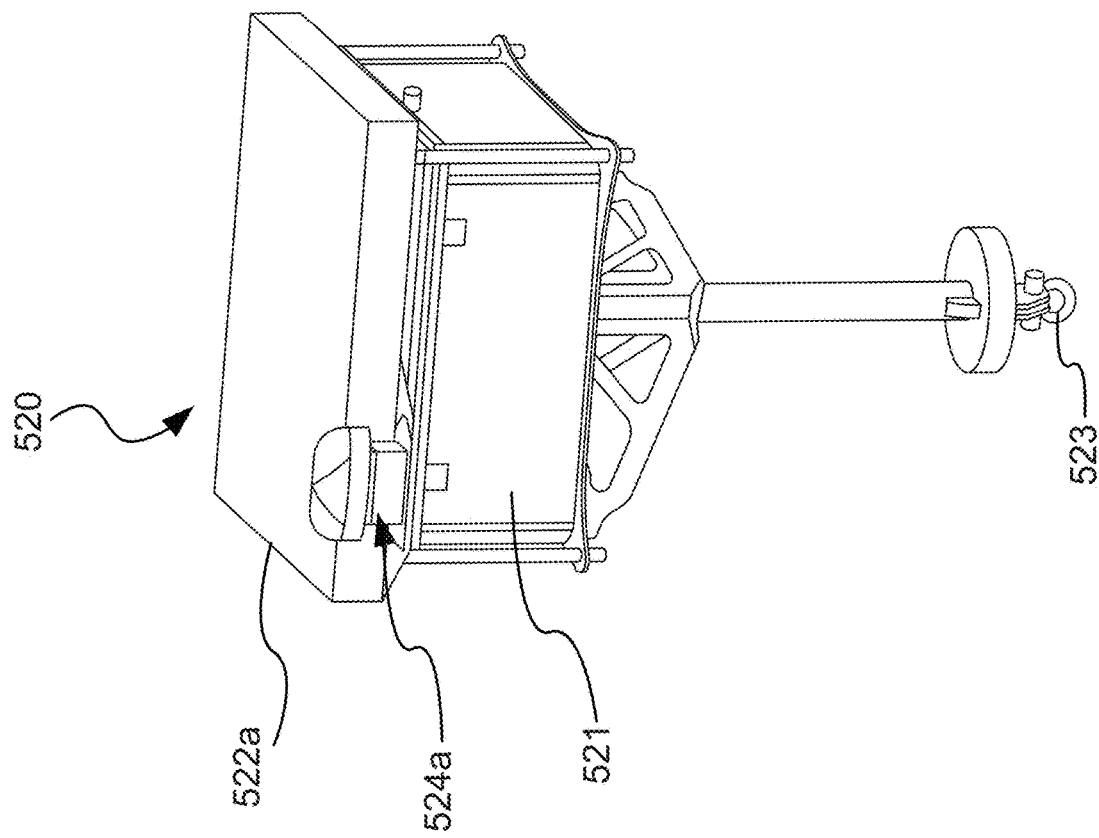

FIGS. 5A and 5B illustrate a first member 520 and 520', each according to a different embodiment. The first members 520 and 520' can be structurally and/or functionally similar to first member 120 in FIG. 1A and/or first member 220 in FIG. 2A. In FIG. 5A, a housing 521 (e.g., structurally and/or functionally similar to housing 121 in FIG. 1B) encloses one or more electronic components of the first member 520. As discussed above, the first member 520 can include power source such as solar cells (e.g., structurally and/or functionally similar to solar cells 122a in FIG. 1B). In some embodiments, the solar cells can form a solar panel. In FIG. 5A, the solar panel 522a is disposed on the top surface of the housing 520. More specifically, in FIG. 5A, the solar panel 522a is disposed above a top surface (e.g., lid) of the housing 521. The antenna 524a (e.g., structurally and/or functionally similar to antenna 124a in FIG. 1B) in FIG. 5A, is entirely disposed on an external surface (e.g., outside) of the housing 521.

In contrast, as seen in FIG. 5B, the solar panel 522a' (e.g., formed from solar cells that are structurally and/or functionally similar to solar cells 122a in FIG. 1B) included in the first member 520' is positioned inside the housing 521'. For instance, the top surface of the housing 521' can be transparent (e.g., can comprise transparent sheets). The solar panel 522a' can be disposed below the top surface (e.g., transparent portion of the housing 520'). In some embodiments, the solar panel 522a' can be disposed below the top surface and adjacent to the housing 521' (e.g., below the transparent portion of the housing 521' and adjacent to the transparent portion of the housing 521'). The antenna 524a' in FIG. 5B is integrated with the housing 521'. For example, the antenna 520a' can be mounted on a connector (e.g., connector 427 in FIG. 4B) within the housing 521'. The connector can be configured to run through the bottom of the housing 521'. The antenna 520a' can be mounted such that the bottom portion of the antenna 524a' is disposed within the housing (e.g., is internal to the housing). However, the head of the antenna 524a' may be positioned above the top surface (e.g., on the external surface) of the housing 521'. In some embodiments, the first member 520 and 520' can comprise low ballast to provide stability to the cultivation apparatus (e.g., cultivation apparatus 102 in FIG. 1). As seen in FIGS. 5A and 5B, the configuration of the first member 520' in FIG. 5B can be more compact than the configuration of the first member 520 in FIG. 5A. More specifically, since the solar panel 522a' is disposed within the housing 521' in FIG. 5B unlike in FIG. 5A), the first member 520' can be more compact than first member 520. Additionally, having the antenna 524a' run through the housing 521' in FIG. 5A can optimize space making the first member 520' more compact.

As discussed above, the first member (e.g., first member 520 in FIG. 5A and first member 520' in FIG. 5B) can include an attachment mechanism (e.g., attachment mechanism 523 in FIG. and attachment mechanism 523' in FIG. 5B) to couple the first member to a support structure (e.g., support structure 260 in FIG. 2) and/or a second member (e.g., second member 140 in FIG. 1A and second member 240 in FIG. 2). The attachment mechanism can be any suitable attachment mechanism such as one or more loops, rings, hooks, etc. In some embodiments, the support structure can be coupled directly to the attachment mechanism. Alternatively, the support structure can be configured to extend from the attachment mechanism. In yet another alternative embodiment, the support structure can be welded to the first member (e.g., near or at the location of the attachment mechanism). The second member can be at least temporarily coupled to the attachment mechanism via a chain and/or a link. In some embodiments, the second member can be welded to the first member near or at the location of the attachment mechanism.

Figure 6B:
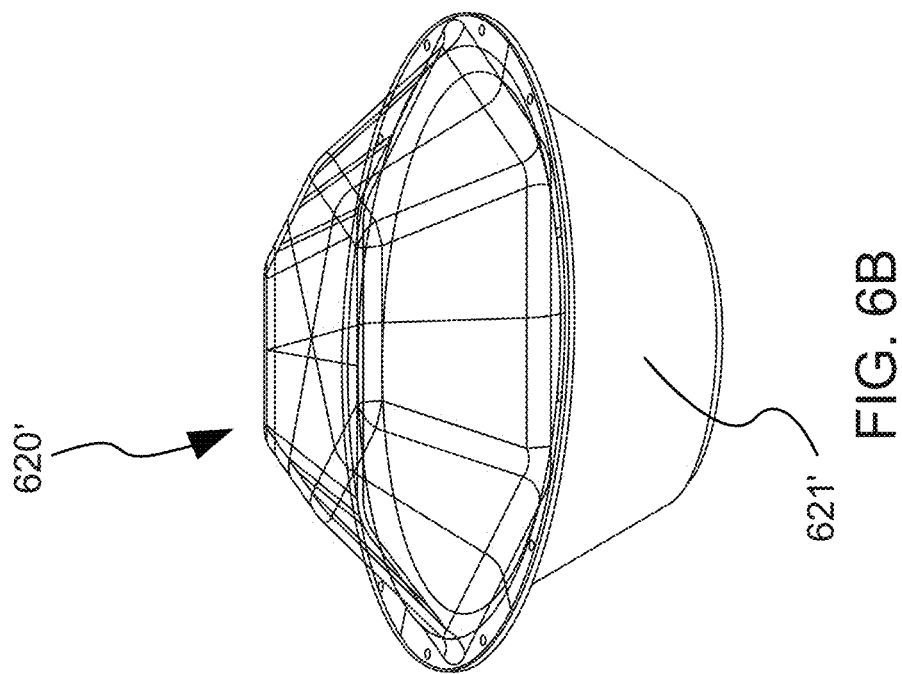
FIGS. 6A and 6B are side perspective views of a first member of a cultivation apparatus, according to a different embodiment.
Figure 6A:
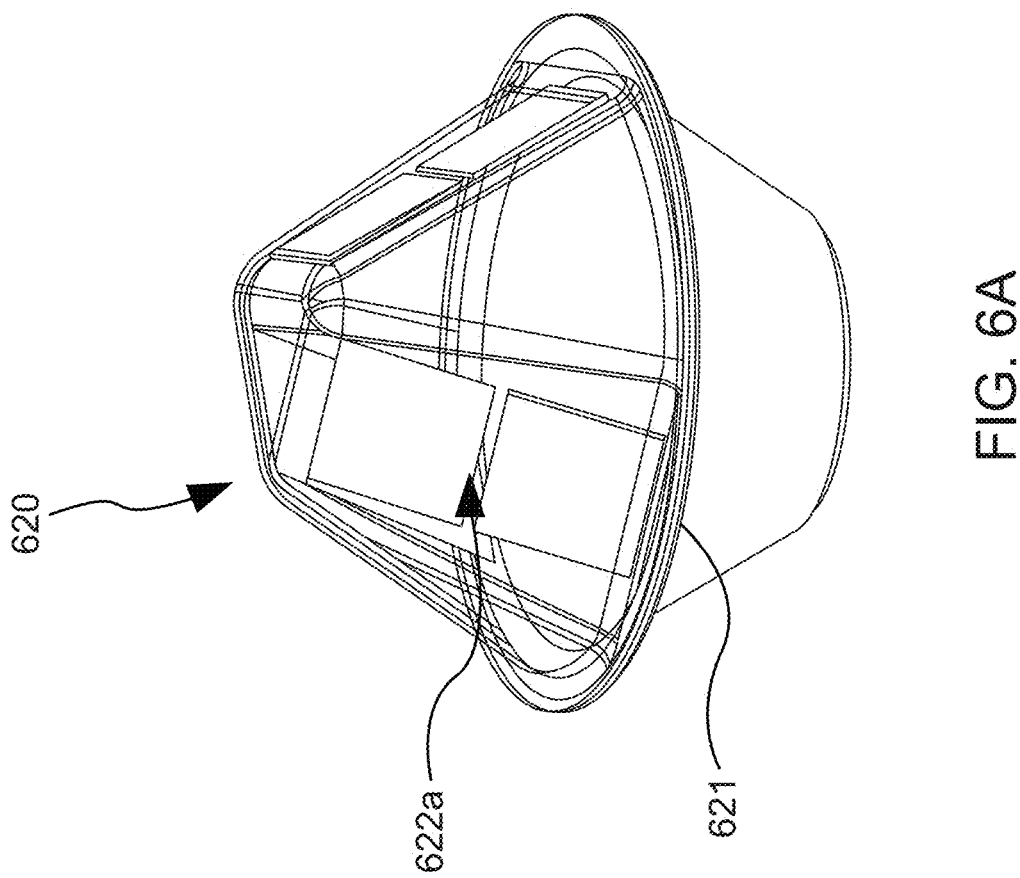

FIGS. 6A and 6B illustrate first members 620 and 620', each according to a different embodiment. The first member 620 and 620' can be structurally and/or functionally similar to first members 120, 220, 320, 420, 520, and/or 520' described above. The first member 620 and 620' can be any suitable shape such as a polyhedral shape seen in FIGS. 6A and 6B. The top surface (e.g., lid) of the first member 620 and 620' can comprise a transparent material. Solar cells 622a and 622a' (e.g., structurally and/or functionally similar to solar cells 122a in FIG. 1B) can be attached to the inner portion of the top surface of the housing 621 and 621' such that they are adjacent to the top surface of the housing 621 and 621'. In some embodiments, similar to FIGS. and 5B, the first member 620 and 620' can comprise low ballast to provide stability to the cultivation apparatus (e.g., cultivation apparatus 102 in FIG. 1A). Although not shown, an antenna (e.g., structurally and/or functionally similar to antenna 124a described above) can be mounted on a connector at the top surface of the housing 621 and 621' similar to FIG. 6B. The housing 621 and 621' can include a gasket (e.g., an elastomer) to seal interfaces (e.g., to seal the lid of the housing to the base of the housing). In contrast to FIG. 6B, the first member 620 in FIG. 6A can be taller than the first member 620' in FIG. 6B. Therefore, the first member 620 can be deployed in areas with high and/or heavy wind currents. Since the first member 620 is taller than the first member 620', the first member 620 can accommodate more solar cells 622a in comparison to the first member 620'. For example, the first member 620 in FIG. 6A can accommodate about 9 solar cells 622a. In contrast, the first member 620' in FIG. 6B can accommodate about 6 solar cells 622a'.

As discussed above with reference to the first members 520 and 520', the first members 620 and 620' can include an attachment mechanism to mechanically couple the support structure and/or the second member. The first members 620 and 620' can couple to the support structure and/or the second member via the attachment mechanism.

Figure 7:
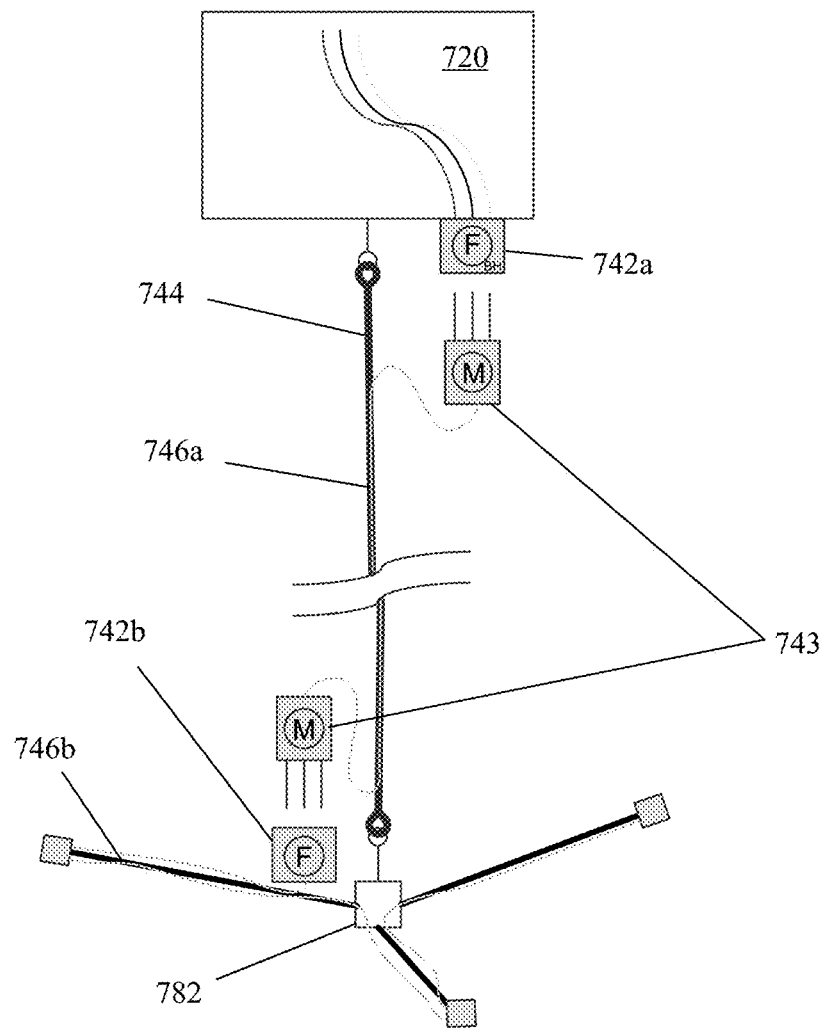
FIG. 7 is a schematic illustration of a support structure of a cultivation apparatus, according to an embodiment.

FIG. 7 is an illustration of the components of a support structure 744 (e.g., structurally and/or functionally similar to support structure 260 in FIG. 2), according to an embodiment. The top end and/or the proximal end of the support structure 744 can be attached to, coupled to, or otherwise integrated with the first member 720. The bottom end and/or the distal end of the support structure 744 can be attached to, coupled to, or otherwise integrated with the sensing module 780 (e.g., structurally and/or functionally similar to sensing module 180 in FIG. 1A and sensing module 280 in FIG. 2). For example, the bottom end and/or the distal end of the support structure 744 can be attached to, coupled to, or otherwise integrated with a frame 782 included in the sensing module 780. The support structure 744 can include a cable (e.g., 746a and 746b collectively referred to herein as cable 746). More specifically, the support structure 744 can itself be a cable 746 that is designed to maintain flexibility in harsh environments. For example, the support structure 744 can comprise a high-grade polyurethane cable 746 that is designed for underwater use. The support structure 744 can be compact, have tighter bends, and can be easily controlled. In some embodiments, the length of the support structure 744 can be any suitable length. In some embodiments, for example, the support structure 744 can have a length allowing it to be positioned at a maximum depth of 200 meters (m) underwater. At least a portion of the support structure 744 (e.g., cable segment 746a) can be surrounded by materials that facilitate target product growth (e.g., such as any of the materials described above with reference to a second member of a cultivation apparatus). For example, cable segment 746a can be surrounded by and/or can be wrapped with cotton that facilitates target product growth.

The support structure 744 can house at least two wires/cords. One wire can transmit power from the first member 720 to the sensing module. Another wire can transmit data (e.g., sensor data, satellite data, and/or GPS data) between the first member 720 and the sensing module 780. The support structure 744 can include two connectors 743 (e.g., male connectors) at the top end and the bottom end to connect with the first member 720 and the sensing module 780. For example, the male connector 743 at the top end of the support structure 744 can connect with the female connector 742a on the first member 720. The female connector 742a can be structurally and/or functionally similar to connector 427 in FIG. 4B. In some embodiments, the antenna included in the first member 720 can be mounted on the female connector 742a. The male connector 743 at the bottom end of the support structure 744 can connect with female connector 742b on the sensing module 780. The male connectors 743 can be configured to withstand harsh ocean conditions.

In some embodiments, the support structure 744 can further include a third wire/cord going from the first member 720 to the sensing module 780. This third wire/cord can include a sensor detection signal line. The sensor detection signal line can enable the first member 720 (e.g., controller such as controller 126 in FIG. 1B included in the first member) to determine whether the sensing module 780 is coupled to support structure 744 and/or whether there is an issue with the connection between the sensing module and the first member 720. For example, the sensing module 780 can include a parallel combination of one or more resistors in the frame 782. The sensor detection signal line can enable the controller in the first member 720 to calculate voltage changes at these resistors. The voltage can be indicative of whether the sensors in the sensing module 780 are plugged in, how many sensors are connected to the first member 720, whether there is an issue with the connection, and/or the like.

Figure 8:
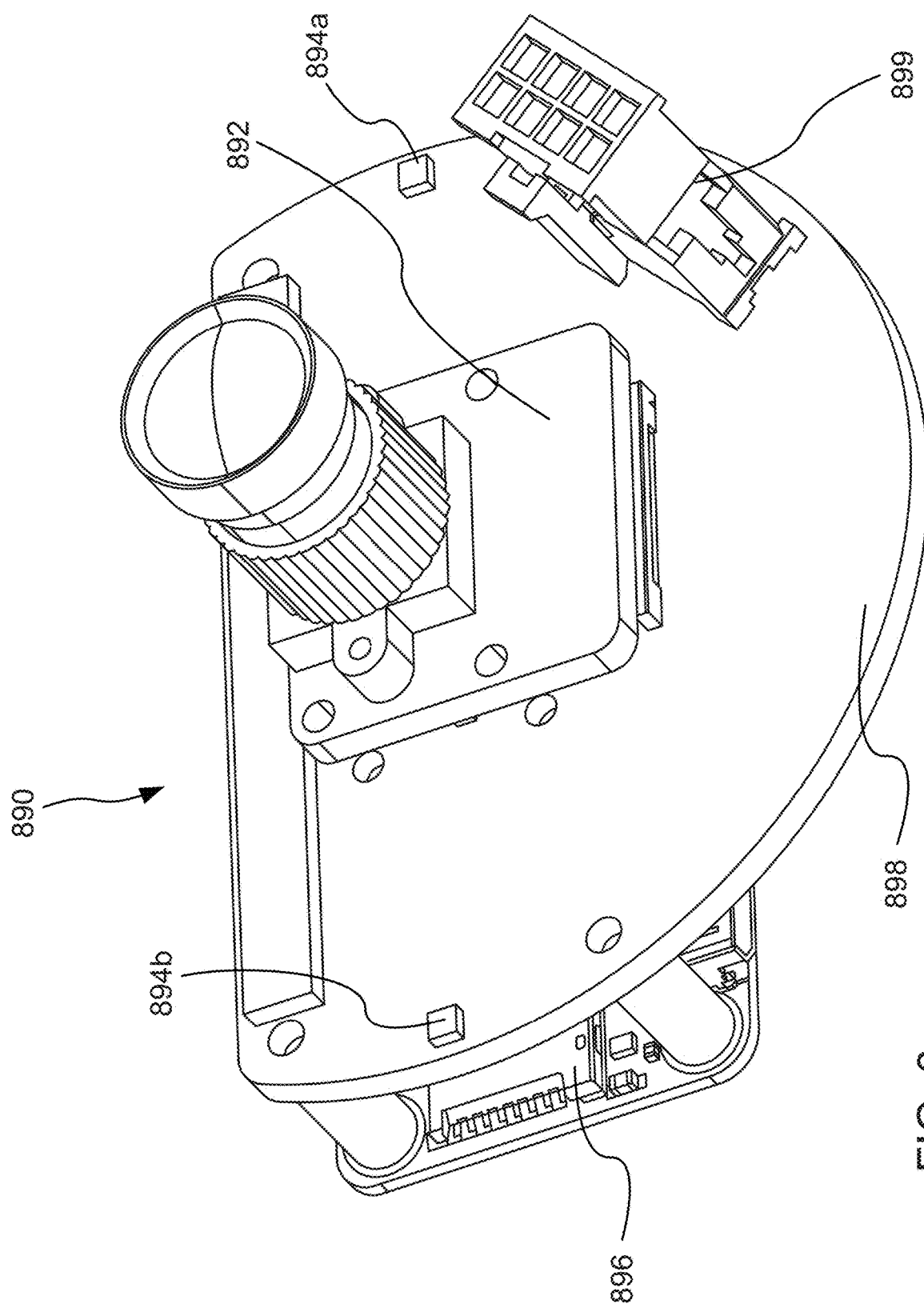
FIG. 8 is an illustration of a sensor included in a sensing module and configured to detect accumulation and/or growth of target products, according to an embodiment.

FIG. 8 is an illustration of a camera 890 included in a sensing module (e.g., a sensor included in any of the sensing modules described above) that can be used to detect accumulation and/or growth of target products, according to some embodiments. In some embodiments, the camera 890 can include one or more light sources 894a and 894b. The light sources 894a and 894b can be a Light-Emitting-Diode (LED) lamp configured to protect the enclosure window from biofouling. In some embodiments, the light sources 894a and 894b emit ultraviolet-C light (e.g., wavelengths between 200 and 300 nanometers). The camera 890 can also include a single-board computer 896 (e.g., Raspberry Pi™) built on a single board circuit including microprocessor(s), memory, and input/output (I/O) interfaces to quantify the intensity of fluorescence signals so as to evaluate the accumulation of target products. The single-board computer 896 can be supported by an extension board 898 (e.g., Pi Hat) that can support the functionality of light sources 894a and 894b. In some embodiments, connector 899 can secure the extension board 898 on the single-board computer 896. While the camera 890 is particularly shown in FIG. 8, it should be understood that it is presented by way of example only and not limitation. Embodiments are possible include additional or fewer components than those identified in FIG. 8. The size, shape, and/or configuration of certain components may also be varied.

For example, in addition to the camera 890, a sensing module can include and/or can be one or more tracking devices configured to produce, and/or transmit signals associated with a relative position of the cultivation apparatus upon (or after) being seeded with target product and deployed on oceans, estuaries, lakes, rivers, and/or any other suitable body of water. The position and/or trajectory of the cultivation apparatus can be transmitted, recorded and/or stored (e.g., by a controller included in the first member) and can be further employed by remote sensing devices to determine and/or quantify (directly or indirectly) target product growth, mass production, and/or carbon capture. For example, in some instances, the cultivation apparatus can include a Global Positioning System (GPS) tracking device configured to determine, record, and/or transmit the cultivation apparatus geographic location. In other instances, the cultivation apparatus can include Radio-Frequency Identification (RFID) devices configured to determine, record, and/or transmit the cultivation apparatus geographic and/or trajectory location. In some instances, trajectory data can be used to determine, calculate, and/or infer mass growth by comparing surface or subsurface conditions (e.g., wind, current, etc.) with subsurface mass motion and/or the like.

FIGS. 9-13 illustrate a sensor 980 included in sensor module that can be used to detect accumulation and/or growth of target products, according to an embodiment. In this embodiment, the sensor 980 is a chlorophyll fluorometer or similar device configured to detect fluorescence emitted as a result of photosynthesis. Moreover, in this embodiment, the sensor 980 includes and/or is integrated with one or more anti-fouling devices, components, features, etc. As described above with reference to the anti-fouling device 170, the anti-fouling device(s), component(s), feature(s), etc. included in the sensor 980 are static devices (e.g., a device with no moving parts), making it/them suitable for deployment (e.g., long-term deployment) in oceanic environments and/or the like.

Figure 9:
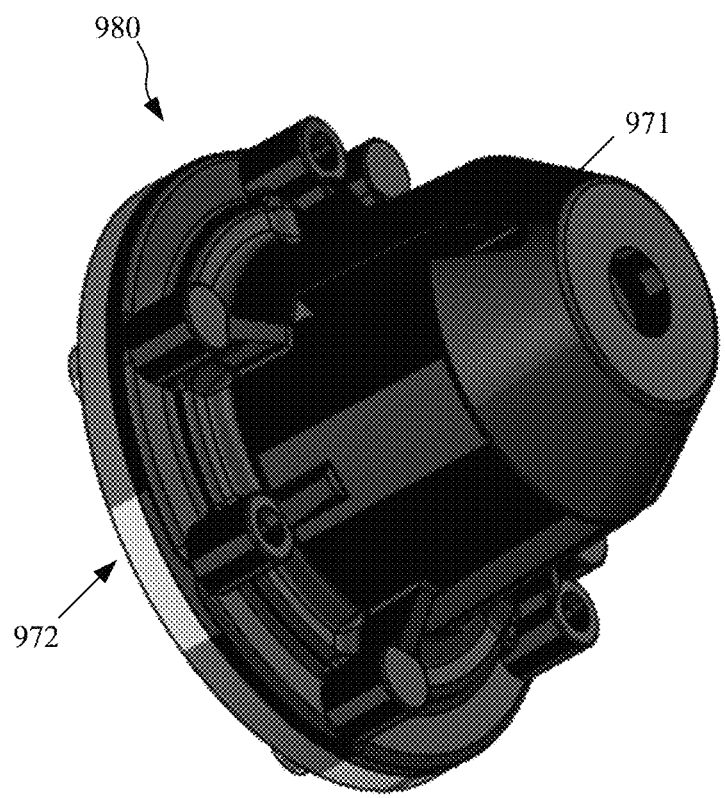
FIGS. 9 and 10 are side perspective views of a sensor included in a sensing module that has an integrated antifouling device, according to an embodiment.
Figure 10:
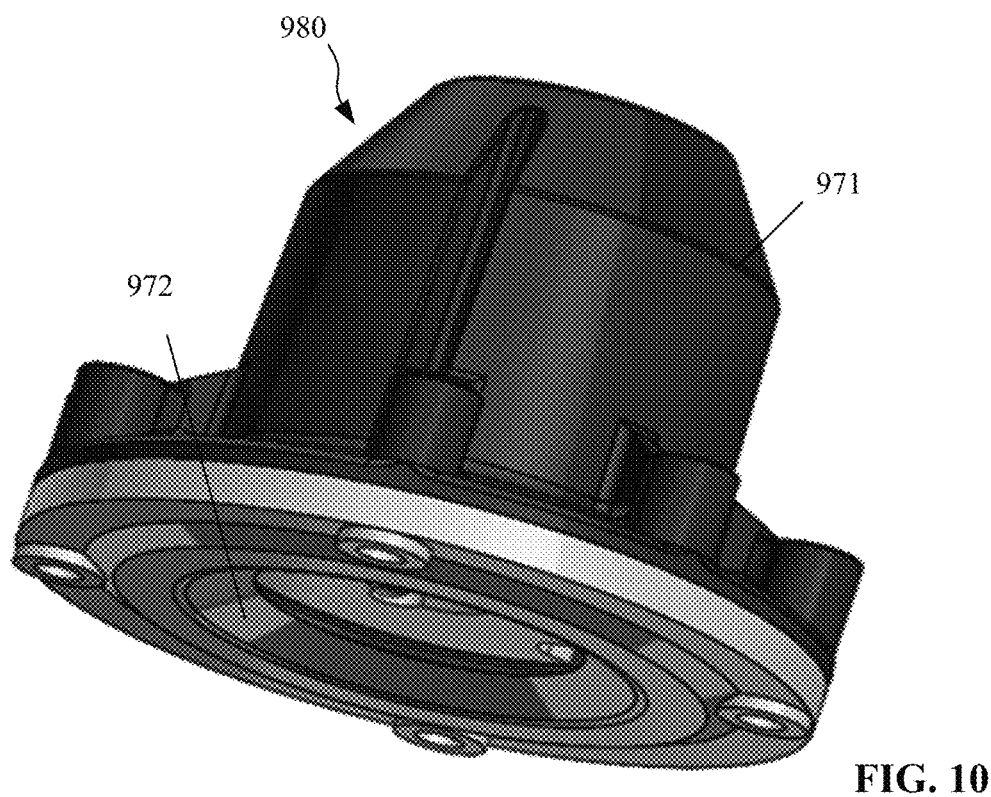

As shown in FIGS. 9 and 10, the sensor 980 includes an optical housing 971 and an optical window 972. The optical housing 971 sits behind and is coupled to the optical window 972 to form a sealed waterproof enclosure of the sensor 980. The sealed waterproof enclosure of the sensor 980 can include, for example, a sealed waterproof electrical connector (not shown) which is configured to allow electrical power and/or data to be transmitted between the sensor 980 and the first member 920 (e.g., via a support structure or the like, as described in detail above). In some implementations, the optical window 972 or at least a portion thereof is made out of a transparent material configured to allow light from one or more light or fluorescence sources to pass therethrough. In contrast, the optical housing 971 can be made out of an opaque or otherwise non-transparent material that is configured to block light transmission through the optical housing 971. In some embodiments, the optical housing 971 and/or the optical window 972 can be an ocean-compatible polymer or plastic that is formed via any suitable process such as, for example, 3D printing, injection molding, and/or the like. In some embodiments, such an arrangement can allow the sensor 980 to be made using known and relatively inexpensive processes.

Figure 11:
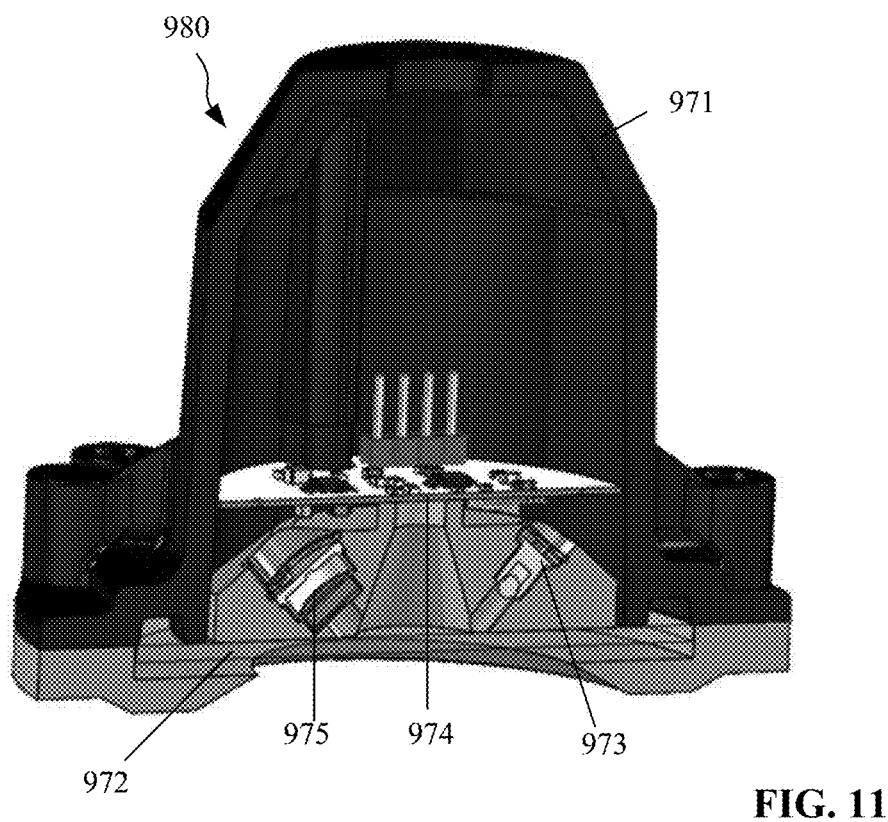
FIG. 11 is cross-sectional view of the sensor of FIGS. 9 and 10.
Figure 12:
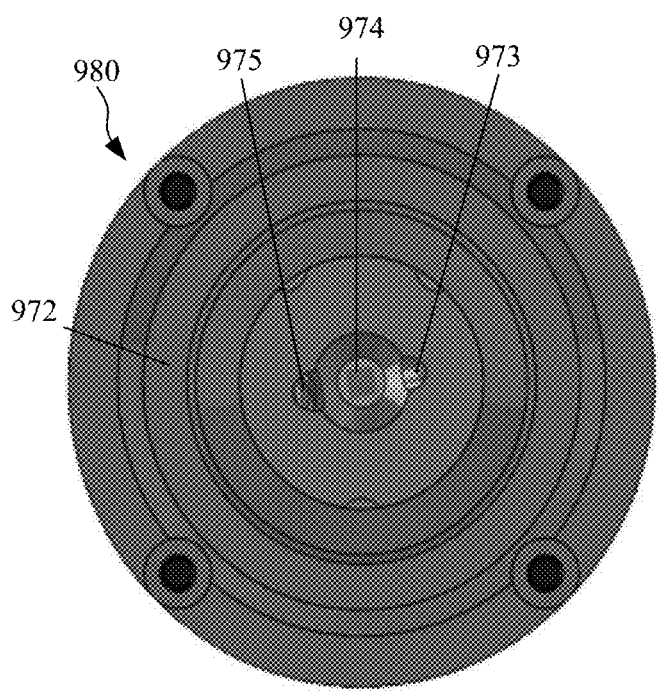
FIG. 12 is a front view of the sensor of FIGS. 9-11.

As shown in FIG. 11, the sensor 980 includes at least a blue Light-Emitting-Diode (LED) 973, an ultraviolet (UV) LED 974, and a photodiode 975, each of which is disposed within the sealed waterproof enclosure collectively formed by the optical housing 971 and optical window 972. The blue LED 973 can be a single LED or an array of blue LEDs. In some implementations, the light generated and/or emitted from the blue LED 973 is in the visible spectrum between about 400 nm and 525 nm. The UV LED 974 can be a single UV LED or an array of UV LEDs. In some implementations, the light generated and/or emitted from the UV LED 974 is in the ultraviolet spectrum between about 250 nm and 280 nm. The photodiode 975 can be a single photodiode or an array of photodiodes. In some implementations, the photodiode 975 can be a charge-coupled device (CCD), an electron-multiplying charge coupled device (EM-CCD), and/or a complementary metal oxide semiconductor (CMOS) detector, and/or any other suitable device. In some embodiments, the photodiode 975 and/or a portion of the optical window 972 can include an optical filter or the like configured to permit light having a predetermined and/or desired frequency to pass through the optical filter while blocking light having other frequencies. For example, the optical filter can be selected to allow the light re-emitted by the fluorophores of the target product in response to the light from the blue LED 973.

In some implementations, the blue LED 973 can be, for example, a detection light source configured to emit a beam of light to and/or through the optical window 972 and/or other components or surfaces of the sensor 980 and toward the target product. In response, fluorophores of the target product can emit fluorescence as a part of the photosynthetic energy conversion process, which in turn, can be detected by the photodiode 975. In some implementations, a controller circuitry (not shown) or the like is connected to the photodiode 975 and used to quantify the intensity of a fluorescence signal that can be used to evaluate the accumulation of marine microorganisms on the sensors. In other embodiments, the photodiode 975 can be configured to output a signal associated with the intensity of the fluorescence signal, which can be transmitted to a controller, processor, and/or the like included in a first member of a cultivation apparatus, as described in detail above.

The data output by the photodiode 975 can be used to quantify and/or estimate, at least in part, the accumulated mass of the target product coupled to a cultivation apparatus, an amount of mass eroded from the cultivation apparatus (e.g., allowed to naturally break off and sink), and/or changes in the mass (e.g., rate of mass accumulation). The data output by the photodiode 975 can, for example, provide insights that facilitate evaluating the relative health of the target product. In some embodiments, the data output by the photodiode 975 can be transmitted to a first member of a cultivation apparatus via a support structure, as described in detail above. In some instances, the data output by the photodiode 975 can be analyzed manually (e.g., manual annotation by a user) or analyzed via one or more automated processes, algorithms, computer vision processes, machine learning models, etc. to determine the mass of the target product, the rate of growth of target product, and/or the amount of $CO_2$ effectively captured by the target product mass accumulated on or by the cultivation apparatus.

Figure 13:
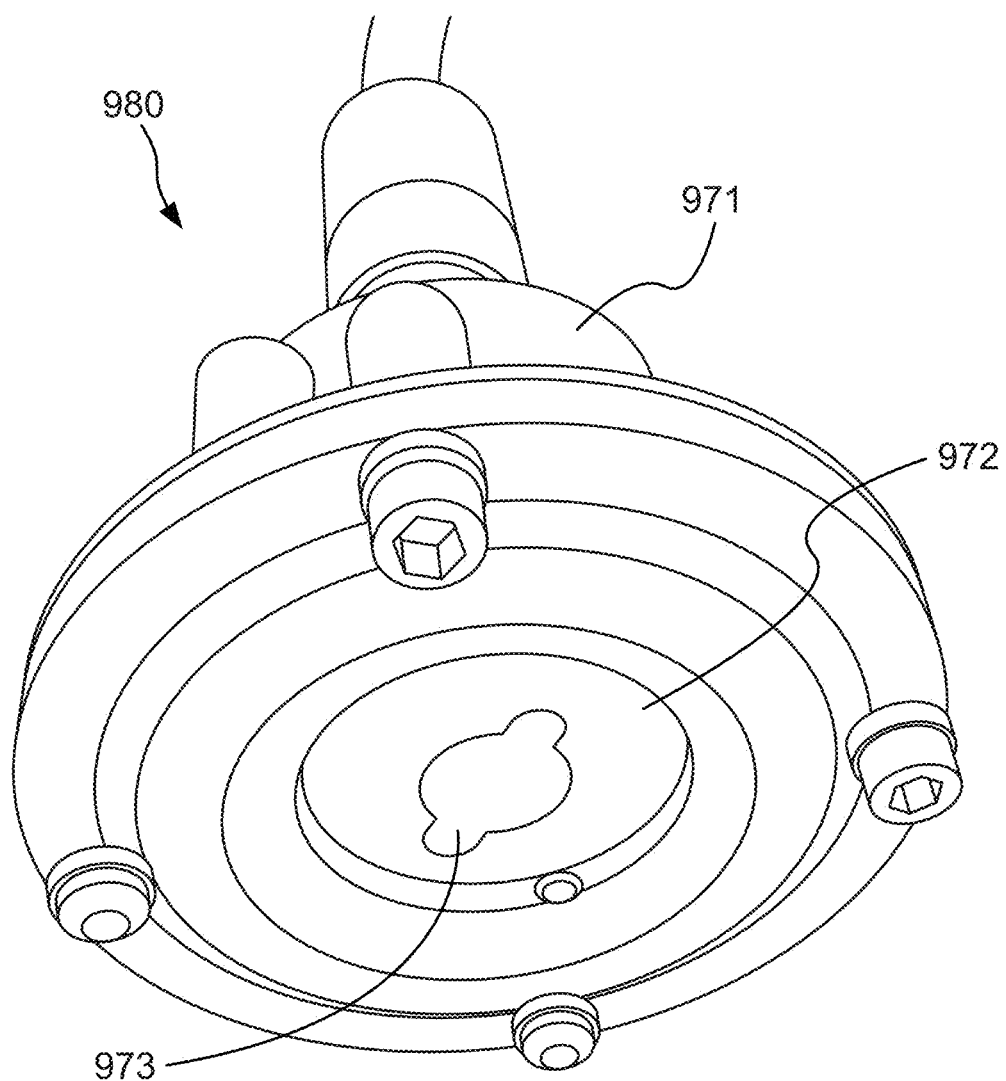
FIG. 13 is front perspective view the sensor of FIGS. 9-12.

In some implementations, the UV LED 974 can be, for example, a UV light source configured to emit a beam of ultraviolet light to and/or through the optical window 972 and/or other components or surfaces of the sensor 980. In some instances, the UV light can be used to remove at least a fraction of the marine microorganisms accumulated on the optical window 972 due to the microorganism's low tolerance to the frequency and/or wavelengths of radiation generated by the UV LED 974 (e.g., UV light having a frequency between 250 nm and 280 nm. For example, the UV LED 974 can emit UV light that irradiates at least a portion of the optical window 972, which in turn, can remove biomaterials, biofilms, slime, and/or other undesirable contaminants from an external surface of the optical window 172. Moreover, the UV light can be filtered or blocked by the optical filter such that the UV light does not interfere with the detection of the fluorescence by the photodiode 975 (described above). For example, FIG. 13 is a front perspective view of the sensor 980 showing the blue light being allowed to pass through the optical window 972. The UV LED 974 is also emitting light but the UV light that is emitted is outside of the visible spectrum and thus, not shown in FIG. 13. In this manner, the sensor 980 can be used to detect one or more characteristics associated with the growth and/or accumulation of the target product, while limiting and/or substantially preventing fouling and/or contamination of the optical window 972 of the sensor 980 (e.g., without the use of moving parts or other cleaning modalities).

Figure 14:
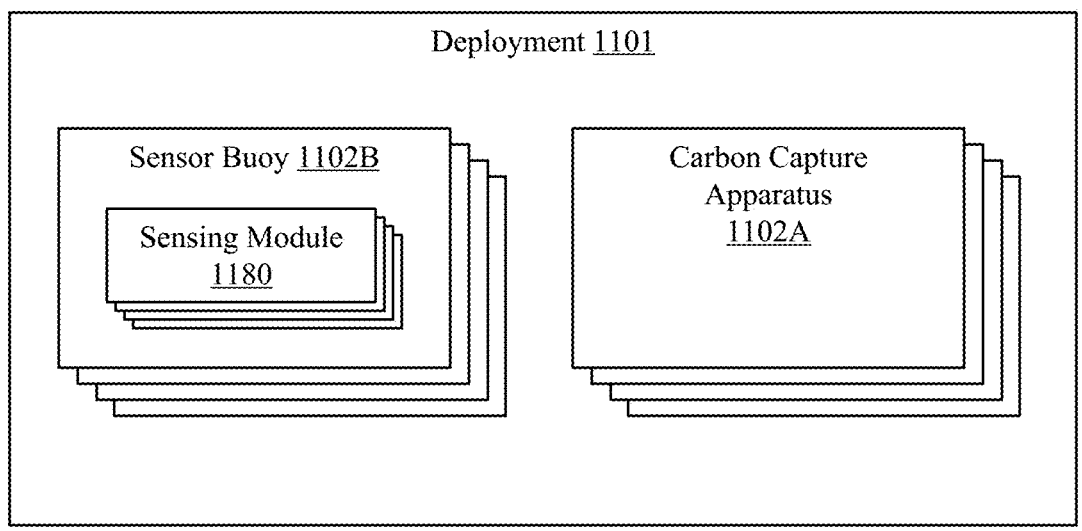
FIG. 14 is a schematic illustration of an ocean-based carbon dioxide removal deployment, according to an embodiment.

FIG. 14 is a schematic illustration of an ocean-based carbon dioxide removal deployment 1101, according to an embodiment. The deployment 1101 (e.g., similar in at least function to the deployment 101 of FIG. 1D) can be made up of any number of carbon capture apparatus 1102A (e.g., functionally and/or structurally similar to the carbon capture apparatus 102 of FIG. 1A) and any number of sensor buoy 1102B. In some implementations, the ocean-based carbon dioxide removal deployment 1101 can be similar to and/or substantially the same as any of those described in the '959 provisional.

In some embodiments, the number of sensor buoys 1102B in the deployment 1101 may be proportional to the number of carbon capture apparatuses 1102A. For example, one sensor buoy 1102B can be present for a larger number of carbon capture apparatuses 1102A. In some embodiments, the deployment 1101 can include a single sensor buoy 1102B for a given subset of carbon capture apparatuses 1102A. In some embodiments, the deployment 1101 can include a single sensor buoy 1102B for ten(s) of carbon capture apparatus 1102A. In some embodiments, the deployment 1101 can include a single sensor buoy 1102B for hundreds(s) of carbon capture apparatus 1102A. In some embodiments, the deployment 1101 can include a single sensor buoy 1102B for thousand(s) of carbon capture apparatus 1102A. In some embodiments, the deployment 1101 can include a single sensor buoy 1102B for ten(s) of thousands of carbon capture apparatus 1102A. In some embodiments, the deployment 1101 can include a single sensor buoy 1102B for hundred(s) of thousands of carbon capture apparatus 1102A. In some embodiments, the deployment 1101 can include a single sensor buoy 1102B for million(s) of carbon capture apparatus 1102A. In some embodiments, the number of sensor buoys 1102B included in a deployment 1101 can be based on other factors such as predicted geographic dispersion of the deployment 1101, predicted density of the deployment 1101, predicted weather conditions, predicted currents or other water (e.g., ocean) conditions, etc.

The carbon capture apparatuses 1102A may be passive buoys that utilize low-energy, low-cost configurations to sequester carbon and transfer carbon from the fast to the slow carbon cycle. For example, the carbon capture apparatuses 1102A may be substrates or structures that are directly seeded or indirectly seeded with a target product. The carbon capture apparatuses 1102A are configured to support the target product as it accumulates biomass until the individual carbon capture apparatus 1102A is no longer buoyant and then sinks, thus transferring carbon from fast carbon cycles to slow carbon cycles (e.g., through photosynthesis of the target product). The carbon capture apparatuses 1102A are configured to be easy and inexpensive to manufacture, due to the scale of the deployment 1101. In some embodiments, the carbon capture apparatuses 1102A do not include any communication device and/or sensors configured to determine the status (e.g., location, speed, target product size, etc.) of the carbon capture apparatuses 1102A. In some embodiments, the carbon sequestration of the carbon capture apparatuses 1102A may be quantified.

In addition to sequestering carbon captured by the target products, it may be desirable to source, form, and/or produce the substrate on which the target product is seeded or otherwise coupled from naturally occurring materials (or from byproducts resulting from other processes) to limit carbon emissions associated with production. In addition or as an alternative, in some implementations, the naturally occurring material can sequester $CO_2$ directly in the production of the substrate, the transformation and/or transitioning of the substrate, the dissolution of the substrate (for example, via ocean alkalinization), and/or in the transport, deposition, and/or burial of the substrate if/when the substrate is removed from the surface of the body of water, the atmosphere, and/or a portion of the fast carbon cycle in the coupled surface water-atmosphere system. In some implementations, it may be desirable to allow such natural substrates to sink along with the target product, thereby reducing carbon emissions otherwise associated with the process of recovering used substrates. In some instances, floatation characteristics and/or the like of the natural substrates used for cultivation of marine target products can be controlled, thereby allowing the substrates to be deployed in a first location and, for example, passively transported to a second location, as described in further detail herein. Various embodiments and/or methods associated with using such substrates formed from naturally occurring materials can include, for example, any of those described in the '285 provisional.

In some implementations, carbonaceous or alkaline minerals can be used to facilitate and/or enhance carbon sequestration. For example, some embodiments and/or methods described herein can include forming and/or coating at least a portion of a substrate from and/or with a carbonaceous and/or alkaline material, and/or that include a naturally occurring material such as an alkaline mineral and/or liquid for sequestering carbon in the deep ocean and/or enhancing ocean alkalinity, thereby improving its ability to sequester carbon. In some implementations, the substrates and/or coatings around at least a portion of the substrate can be configured to degrade and/or dissolve when the substrate is deployed in a body of water, which in turn can independently capture and/or sequester carbon, enhance ocean alkalinity improving its ability to sequester carbon, and/or transition the substrate from first configuration having a positive buoyancy to a second configuration having a negative buoyancy. The transitioning of the substrate to the second configuration causes the substrate to sink as an independent mode of carbon sequestration or in addition to an amount of target product that accumulated while the substrate was in the first configuration. Various embodiments and/or methods associated with using substrates coated in a carbonaceous or alkaline mineral or material can include, for example, any of those described in the '286 provisional.

In some implementations, the substrates described herein may include or may be formed from and/or using alkaline liquids. For example, low-energy methods may be employed for using globally abundant naturally occurring alkaline fluids, such as those found as surface and subterranean fluids, hydrothermal brines, basinal brines, oil-field brines, sub-seafloor fluids, evaporite brines, among other alkaline fluids, that occur within alkaline mineral deposits, such as metal silicates (e.g., mafic/ultramafic igneous rocks), limestones, dolostones, and evaporite deposits, to sequester $CO_2$ from the Earth's fast carbon cycle (the upper ocean and atmosphere) to its slow carbon cycle (deep ocean, marine sediments, rocks and other upper subterranean reservoirs). Such alkaline fluids may be naturally high in pH, alkalinity, and divalent cation concentration, and therefore ideally suited for large scale $CO_2$ sequestration via ocean alkalinity enhancement and/or mineralization. Such natural alkaline fluids can also have high temperatures at the point of extraction, which can be advantageous if used in the production of substrates that are aggregated, for example, with cementitious and/or polysaccharide hydrogels by reducing the heat input required to activate and cure these binders. The characteristically high concentration of divalent cations and alkalinity of such alkaline fluids can also speed the activation and curing process of cementitious and/or hydrogel binders used in the production of substrates engineered for $CO_2$ sequestration. Various embodiments and/or methods associated with using alkaline fluids independently and/or in one or more processes for forming substrates can include, for example, any of those described in the '381 provisional.

Moreover, any of the carbon capture apparatuses 1102A (or payloads thereof) included in the deployment 1101 (e.g., substrates formed using naturally occurring cellulosic materials carbonaceous materials, and/or alkaline fluids, with or without target product seeded thereto or otherwise supported thereby) may be deployed at strategic locations in a body of water such that they sequester atmospheric carbon and/or increase alkalinity of the body of water while being transported passively to the deep ocean. The carbon capture apparatuses 1102A may continue to sequester carbon in the deep ocean and/or reduce acidity of the ocean, and may eventually sink to the ocean floor to transfer the sequestered carbon to the slow carbon cycle. The entire lifecycle of any of the carbon capture apparatuses 1102A described from extraction (e.g., from natural mineral sources or any other source(s)), manufacturing, assembly, transportation, and/or deployment in the body of water, to the sequestering of carbon and transfer of carbon to the slow cycle occurs in a net negative carbon footprint, thus resulting in a decrease in the global carbon footprint.

In the embodiment shown in FIG. 14, the sensor buoys 1102B are configured to monitor the status of the carbon capture apparatuses 1102A in the deployment 1101 and/or are otherwise configured to collect data associated with the carbon capture apparatuses 1102A, the deployment 1101, and/or the environment where the deployment 110 is deployed.

In some embodiments, the sensor buoy 1102B can include a first member and a second member, as described above with reference to the cultivation apparatus 102 and/or 202 described above. For example, the first member may be configured to facilitate floatation and/or to house electronics. The first member can provide buoyancy, at least temporarily, to various components of the system and to at least partially house various components such as a power source, a controller (and/or other electronics), and/or the like. The power source can be configured to provide power to the controller (and/or other electronics) and at least one sensing module (e.g., a sensing module 1180) configured to obtain sensor data that can be representative of one or more characteristics associated with biomass accumulation of the target product seeded on or in the second member. The controller and/or other electronics can receive the sensor data and/or any other suitable data associated with the system and/or the deployment environment and, in turn, can use the data to determine and/or predict an amount of accumulation of the target product seeded on or in the second member. In some implementations, the determination and/or prediction of the accumulation can be used to determine, infer, and/or predict an amount of biomass accumulation for all the target product cultivated by the system (e.g., all the target product seeded on the individual passive carbon capture apparatus in a deployment). In some embodiments, the first member can be similar in at least form and/or function to the first member 120 of the cultivation apparatus 102.

The second member may be configured to contain the target product. In some embodiments, the second member is seeded (directly or indirectly) with the target product. The second member is configured to be seeded with one or more species of the target product and can provide a structure that allows the cultivation and/or accumulation of the target product as the target product matures. The second member can be any suitable shape, size, and/or configuration. For example, in some embodiments, the shape, size, and/or configuration of the second member can be similar to or substantially the same as the shape, size, and/or configuration of the first member or buoy. In other embodiments, the shape, size, and/or configuration of the second member can be different than the shape, size, and/or configuration of the first member or buoy. In some embodiments, the second member can be and/or can include one or more seeding lines and/or the like. In some embodiments, the second member can be similar to or substantially the same as any of the second members described in detail in the '315 patent and/or the '681 application. In some embodiments, the second member can be similar in at least form and/or function to the second member 140 of the cultivation apparatus 102.

Each sensor buoy 1102B in the deployment 1101 includes the sensing module 1180 (e.g., structurally and/or functionally similar to the sensing module 180 of FIG. 1A). In some embodiments, the sensing module 1180 is coupled to the first member. The sensing module 1180 is configured to send/receive data to/from the first member and collect the data on the target product or the deployment 1101. In some embodiments, the sensor buoy 1102B includes an imaging device configured to monitor and/or collect data associated with the target product growth within the second member. In some embodiments, data collected by the sensing module 1180 may be used to quantify the growth of the target product (e.g., contained or seeded on the second member), in a manner similar to the any of the quantification methods described in the '681 application. In some embodiments, the sensing module 1180 also may be configured to measure and/or determine the location, speed, movement characteristics, water details (e.g., temperature, mineral content, etc.), air temperature, wind speed, and/or the like.

In some embodiments, the sensor buoy 1102B includes an antifouling device (e.g., functionally and/or structurally similar to the anti-fouling device 170 of FIG. 1A and/or the anti-fouling devices included in the sensing module 980 of FIGS. 9-13). In such embodiments, the antifouling device can be configured to limit and/or substantially prevent fouling of one or more sensors, imaging devices, and/or other equipment included in the sensing module 1180.

In addition or alternatively, in some embodiments, the sensor buoy 1102B includes a scuttling device. The scuttling device is configured to, upon receiving a signal indicating scuttling is desired, sink the sensor buoy 1102B. For example, the scuttling device may be remotely actuated to allow water to infiltrate at least a portion of the sensor buoy 1102B to decrease the buoyance of the sensor buoy 1102B until the sensor buoy 1102B is no longer buoyant and sinks. The scuttling device may be integrally formed in the sensor buoy 1102B or may be coupled to at least a portion of the sensor buoy 1102B. An embodiment of a scuttling device is described in further detail with reference to FIGS. 20-22C.

Figure 15:
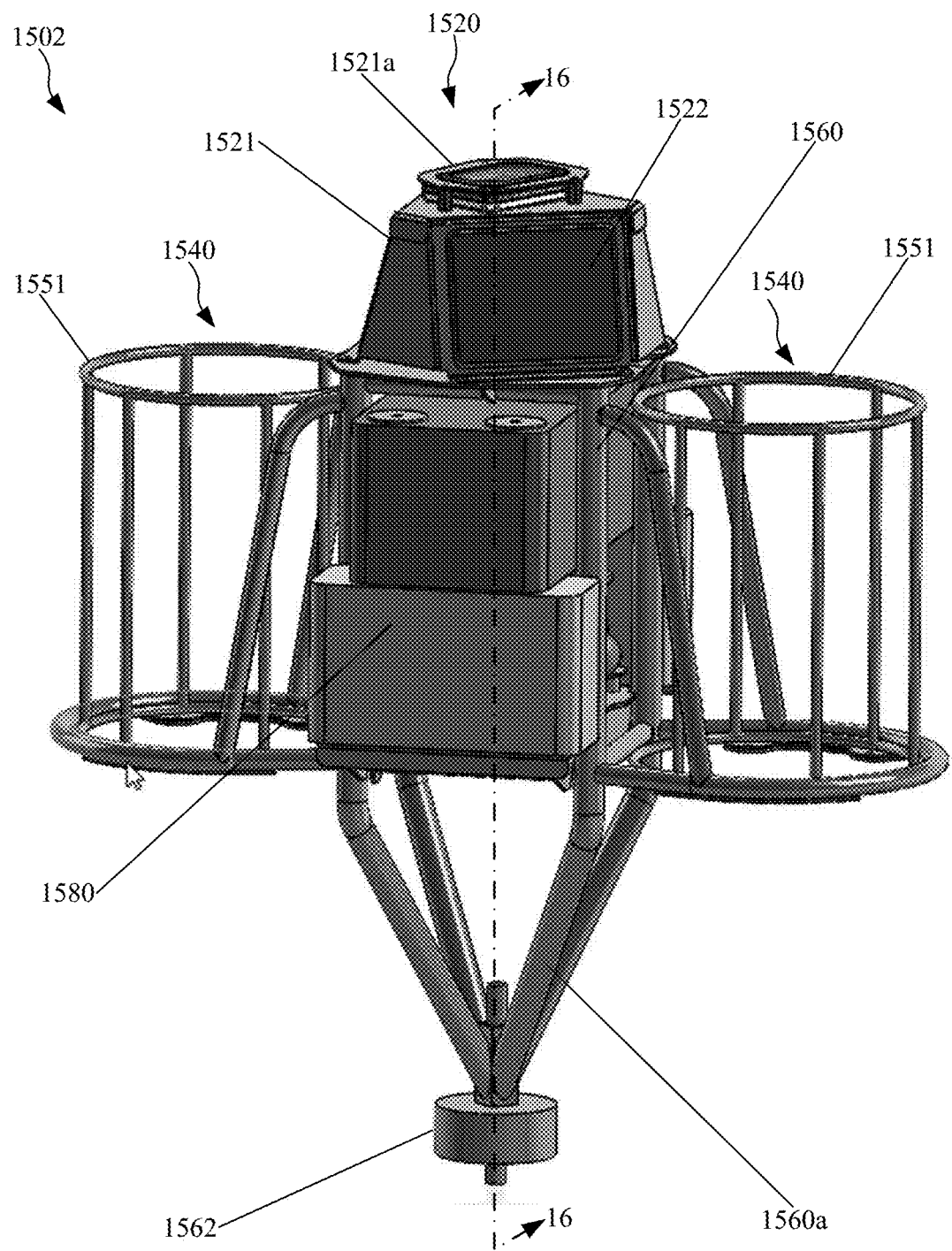
FIG. 15 is an illustration of a sensor buoy included in an ocean-based carbon dioxide removal deployment, according to an embodiment.

FIG. 15 is an illustration of a sensor buoy 1502, according to an embodiment. The sensor buoy 1502 is configured to monitor growth of target product within the sensor buoy 1502 and/or is configured to monitor and/or collect data associated with the sensor buoy 1502, a deployment, and/or an environment where the deployment is deployed. As discussed above, target product(s) can include and/or encompass a wide variety of species including but not limited to microalgae, macroalgae, plankton, marine bacteria, archaea filter feeders (such as oysters or clams), and/or crustaceans. The target product can be grown on the sensor buoy 1502 deployed in a suitable water body. The sensor buoy 1502 can be any suitable shape, size, and/or configuration.

The sensor buoy includes a first member 1520 and a second member 1540. The first member 1520 can be structurally and/or functionally similar to the first member 220 of FIG. 2A. As shown, the first member 1520 includes a top enclosure 1521, a controller housing 1521a, a frame 1560, and a sensing module 1580.

The controller housing 1521a is a housing configured to store a controller (e.g., discussed further in reference to FIG. 17) that controls certain operations of the sensor buoy 1502. The controller housing 1521a is located on the top of the sensor buoy 1502 and above the water line (e.g., a height water reaches on the sensor buoy 1502 when floating on the surface of the water) so that communication components (e.g., GPS, GPS antenna, satellite modem, etc.) can operate and so that sensors (e.g., inertial measurement unit, humidity sensor, etc.) can determine operating conditions of and/or associated with the sensor buoy 1502 as well as ambient atmospheric conditions (e.g., precipitation, temperature, humidity, etc.) above the water. In some embodiments, the data determined by the controller may include ocean data and/or the satellite data. The ocean and/or satellite data can include measurements such as ocean surface temperatures, atmospheric temperature and humidity, salinity of the water, color of the water, spectral reflection of the water, nutrient content, alkalinity, nitrogen content, water depth, wave sizes, wave periods, tide information, current direction, current speed, windage, relative position of the sensor buoy 1502, dispersion (e.g., trajectory) of the sensor buoy 1502, and/or any other suitable data (e.g., as described in the '681 application and/or the like). In some embodiments, the controller housing 1521a is water-tight to prevent the controller and other devices within the controller housing 1521a from coming into contact with water. In some embodiments, at least a portion of the controller housing 1521a allows water to pass through (e.g., permeable, semipermeable, open, etc.) to allow for at least some components of the controller to contact water.

The controller housing 1521a is fixedly coupled (e.g., via a fastener, weld, adhesive, etc.) to and extends into the top enclosure 1521. The top enclosure 1521 is configured to house components of the of the sensor buoy 1502. For example, the top enclosure 1521 may house controller components and a wiring harness. In some embodiments, the top enclosure 1521 may define and/or form an inner volume or an empty space that provides buoyancy for the sensor buoy 1502. The top enclosure 1521 may also serve as a mounting point for a power source (e.g., structurally and/or functionally similar to the power source 122 of FIG. 1B) which may include at least one solar cell 1522 (e.g., solar panel) (e.g., functionally and/or structurally similar to the solar cell 122*a* of FIG. 1B).

The solar cells 1522 can produce direct current (DC) energy. In some embodiments, the power source can include a collection of solar cells 1522 forming a solar panel. In some embodiments, the solar panel can be disposed above a top surface of the top enclosure 1521. Alternatively, at least a portion of a surface of the top enclosure 1521 can be transparent. For example, at least a portion of a side surface of the top enclosure 1521 can include polycarbonate sheets such as Lexan and/or other transparent plastic sheets. The solar panel can be disposed within the top enclosure 1521 itself. In some embodiments, one or more solar cells 1522 can be attached to the inner portion of the surface of the top enclosure 1521 such that the solar cells 1522 are positioned within the top enclosure 1521. For example, one or more solar cells 1522 can be attached to the surface inside the top enclosure 1521 using a suitable adhesive (e.g., adhesive patch, glue, paste, etc.) such that the solar cells 1522 are positioned adjacent to the top surface of the housing. The solar cells 1522 can produce or output any suitable range of power. The power source may store energy in an energy storage device (e.g., battery, accumulator, etc.). In some embodiments, the energy storage device can be a mechanical energy storage device such as flywheel configured to store kinetic energy (e.g., rotational energy) that can be discharged as electric energy. In some embodiments, the energy storage device can be a battery (e.g., a lithium battery). In some embodiments, the energy storage device can store, produce, and/or output any suitable range of power. In some embodiments, the energy storage device may be located in the top enclosure 1521 or in another location on the sensor buoy 1502.

The DC energy produced by the solar cells 1522 can be used to power one or more components of the sensor buoy 1502. In such embodiments, if the solar cells 1522 stop producing energy (e.g., due to lack of sunlight or damage), the energy storage device can act as a backup power source. Alternatively, the energy storage device can store at least some or all of the DC energy produced by the solar cells 1522 and, in turn, can provide power to the components of the sensor buoy 1502.

The top enclosure 1521 is fixedly coupled to the frame 1560. In some embodiments, the top enclosure 1521 is integrally formed with the frame 1560. The frame 1560 is a structural frame for the sensor buoy 1502 and provides a space for the sensing module 1580 to be stored. In some embodiments, the frame 1560 may be formed of a metal (e.g., steel, aluminum, etc.), a composite (e.g., fiberglass, carbon fiber, etc.), or another material (e.g., vinyl, plastic, etc.) suitable to be used in an ocean environment. The frame 1560 may be formed of tubes, rods, plates, and/or any other structure(s) to provide sufficient stiffness to the sensor buoy 1502. The frame 1560 may additionally include and/or may be coupled to a ballast, sensors, cameras, batteries, and/or any other suitable components of the sensor buoy 1502.

Figure 16:
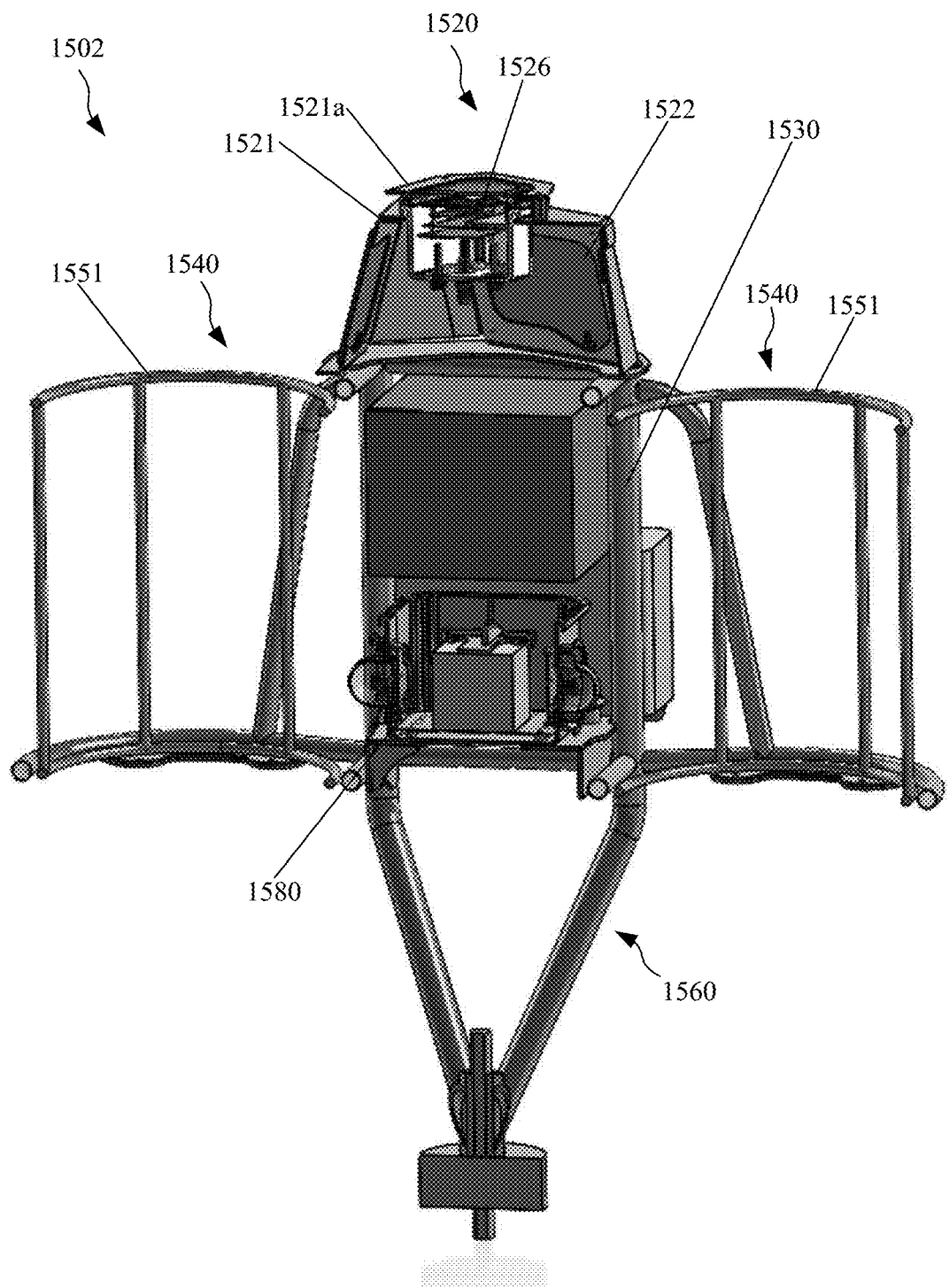
FIG. 16 is a cross-sectional view of the sensor buoy of FIG. 15 taken along the line 16-16.

As shown in FIGS. 15 and 16, a bottom portion 1560*a* of the frame 1560 extends opposite the top enclosure 1521. The bottom portion 1560*a* can include a ballast 1562 configured to keep the sensor buoy 1502 partially submerged in water. In some embodiments, the ballast 1562 is heavy enough to keep the target product partially submerged. That is to say, the ballast 1562 can reduce or limit a buoyancy of the sensor buoy 1502 such that while the sensor buoy 1502 floats on the water, a desired portion of the sensor buoy 1502 is below the surface of the water. In some embodiments, the bottom portion 1560*a* may include additional components configured to affect the motion of the sensor buoy 1502. For example, although not shown, the bottom portion 1560*a* of the frame 1560 may include motors, gyroscopes, positioning fins, and the like.

The second member 1540 can be structurally and/or functionally similar to the second member 240 of FIG. 2A. For example, the second member 1540 includes and/or forms substrate containment structures 1551 (e.g., cages, pens, enclosures, etc.). The substrate containment structures 1551, and thus the second member 1540 generally, is coupled to the frame 1560 such that the sensing module 1580 can monitor growth of the target product within the substrate containment structures 1551.

In some embodiments, the substrate containment structures 1551 are fixedly coupled to the frame 1560. In some embodiments, the substrate containment structures 1551 are integrally formed with the frame 1560. The substrate containment structures 1551 can be seeded with and/or configured to receive a species of target product (e.g., macroalgae gametophytes and/or sporophytes). The substrate containment structures 1551 protect the target product so that the growth of the target product may be monitored. In some embodiments, the substrate containment structures 1551 can be lined with a mesh, net, or the like, to further protect the target product. The substrate containment structures 1551 may include vertical bars, horizontal bar, diagonal bars, and the like to contain the target product. The substrate containment structures 1551 are positioned on the frame 1560 such sensors (e.g., cameras, humidity sensors, fluorometers, etc.) may monitor the target product within the substrate containment structures 1551. While the sensor buoy 1502 is shown as including two substrate containment structures 1551, in other embodiments, the sensor buoy 1502 can include fewer than two or more than two substrate containment structures 1551 (e.g., three, four, five, six, seven, eight, nine, ten, or more). The substrate containment structures 1551 may be arranged symmetrically or asymmetrically around the frame 1560.

FIG. 16 is a cross-sectional view of the sensor buoy 1502 of FIG. 15 taken along the plane 16. The cross-sectional view shows the first member 1520 including a controller 1526 and a telemetry unit 1524 disposed within the top enclosure 1521 and the sensing module 1580 located within the frame 1560. The controller 1526 extends past the controller housing 1521*a* into the top enclosure 1521. The sensing module 1580 is located in the same horizontal plane as a portion of the substrate containment structures 1551. The sensing module 1580 (discussed further in reference to FIGS. 18-19B) includes imaging devices and/or other sensors that may monitor the contents of the substrate containment structures 1551. In some embodiments, the sensing module 1580 may have an imaging device corresponding to each substrate containment cage 1551 and configured to monitor the contents therein. In some embodiments, the sensing module 180 may include one or more cameras configured to observe the contents in multiple substrate containment structures 1551. The sensing module 1580 is oriented in the first member 1520 such that imaging devices and/or sensors in the sensing module 1580 are capable of monitoring the target product within the substrate containment cage 1551. In some embodiments, the substrate containment cage 1551 includes an opening to allow for the sensing module 1580 to monitor the target product. In some embodiments, the sensing module 1580 and the controller 1526 and/or the telemetry unit 1524 are interconnected via a wiring harness and/or the like within the first member 1520. In some embodiments, the sensing module 1580, the controller 1526, and/or the telemetry unit 1524 are connected via a wireless connection (e.g., Wi-Fi, Bluetooth, etc.).

Figure 17:
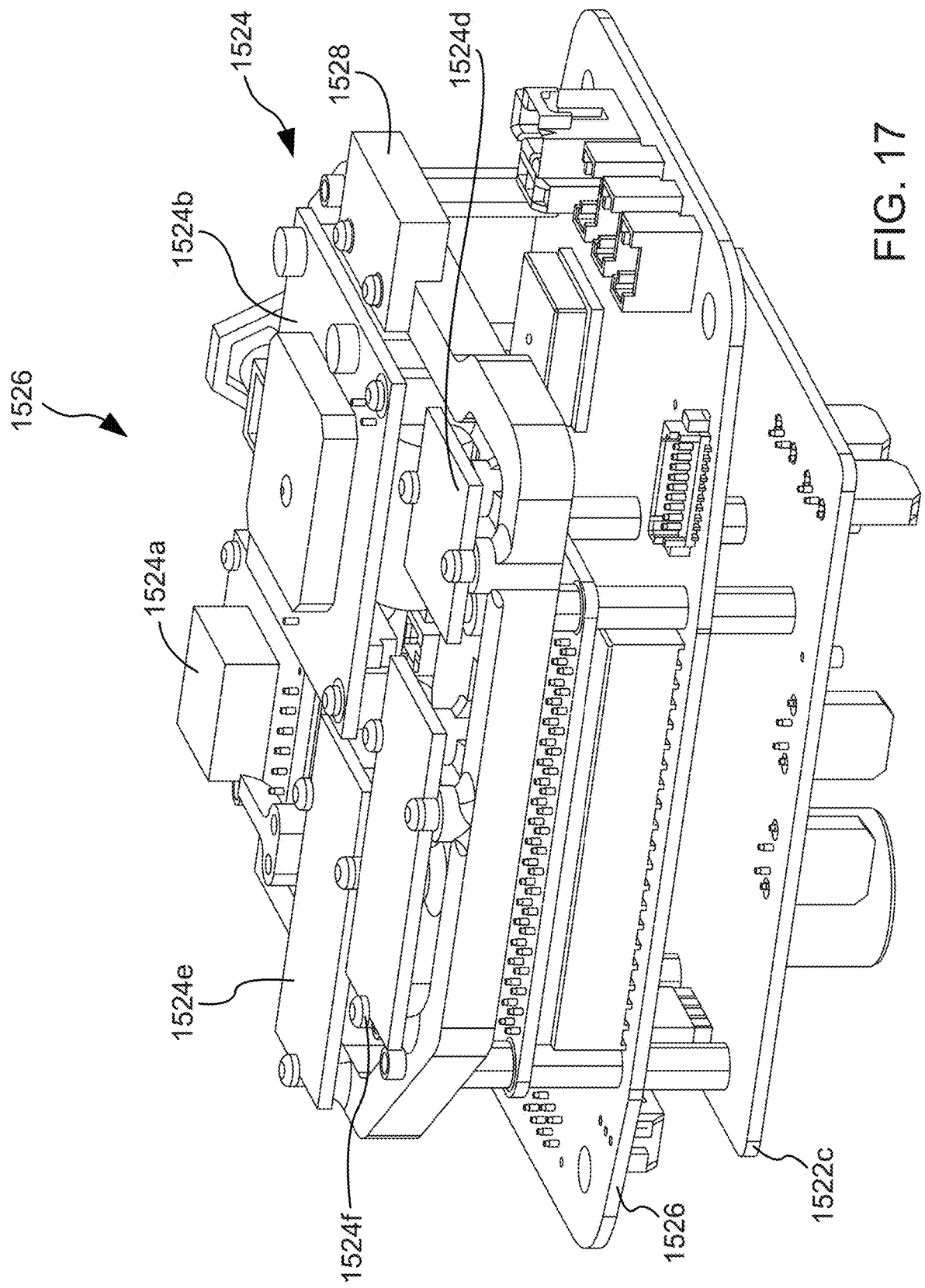
FIG. 17 is an illustration of a controller included in the sensor buoy of FIG. 15.

FIG. 17 is an illustration of the controller 1526 (e.g., structurally and/or functionally similar to the controller 126 of FIG. 1B). The controller 1526, shown in FIG. 17, has been removed from the sensor buoy 1502 for clarity. The controller 1526 is communicatively coupled to the telemetry unit 1524 (e.g., structurally and/or functionally similar to the telemetry unit 124 of FIG. 1B), a compute device 1524c, and a charging circuit 1522c. The controller 1526 may be communicatively coupled to the imaging device and/or other sensors of the sensing module 1580. The controller 1526 may be coupled to a power source of the sensor buoy 1502 or may include its own on-board power source and/or power generation source.

The telemetry unit 1524 (or the controller 1526) includes a component tray that includes a positioning antenna 1524a, a satellite modem 1524b, a magnet switch 1528, a humidity sensor 1524d, an inertial measurement unit 1524e and an additional sensor slot 1524f which allows for additional sensors to be mounted to the component tray to expand the functionally of the telemetry unit 1524 and/or the controller 1526. The telemetry unit 1524 is coupled to the compute device 1524c and may send data and/or information to the compute device 1524c for processing. In some embodiments, the telemetry unit 1524 can provide information and/or data associated with the body of water (e.g., ocean), the local and/or forecasted weather, and/or the sensor buoy 1502. In some embodiments, the telemetry unit 1524 can include one or more sensors and/or devices (e.g., modems, antennas, etc.) that receive data and/or sense and collect data relating to the ocean. Additionally or alternatively, telemetry unit 1524 can receive satellite data from one or more satellites (e.g., communication satellites, global navigation satellite system (GNSS) satellites, etc.). In some embodiments, the ocean data and/or the satellite data can include measurements such as ocean surface temperatures, atmospheric temperature and humidity, salinity of the water, color of the water, spectral reflection of the water, nutrient content, alkalinity, nitrogen content, water depth, wave sizes, wave periods, tide information, current direction, current speed, windage, relative position of the sensor buoy 1502, dispersion (e.g., trajectory) of the sensor buoy 1502, and/or the like. The telemetry unit 1524 can be structurally and/or functionally similar, at least in part to the telemetry unit 124 described above with reference to FIG. 1B. Thus, certain portions and/or functions of the telemetry unit 1524 are not described in further detail herein.

In some embodiments, the positioning antenna 1524a can receive satellite signals transmitted from the one or more communication satellites and GPS radio signals transmitted by the GNSS satellites. Similarly stated, the positioning antenna 1524a can be a dual band antenna configured to receive both satellite signals and GPS radio signals. In some embodiments, the positioning antenna 1524a can be disposed on an external surface (e.g., outside) of the controller housing 1521a. Alternatively, the positioning antenna 1524a can be integrated with the controller housing 1521a such that only a portion of the positioning antenna 152a (e.g., the head of the antenna) is on the external surface of the controller housing 1521a. More specifically, the positioning antenna 1524a can be integrated with the controller housing 1521a such that one end of the positioning antenna 1524a is positioned within (e.g., internal to) the controller housing 1521a. The positioning antenna 1524a can run from inside the controller housing 1521a through the top surface of the controller housing 1521a such that the opposite end of the positioning antenna 1524a (e.g., head of the antenna) is disposed on the external surface of the controller housing 1521a.

The satellite modem 1524b can transform the satellite signals received from the communication satellite(s) into a bitstream. In some embodiments, the satellite modem 1524b can implement Server Message Block (SMB) protocol to access satellite data from the communication satellites. The satellite modem 1524b can be configured to receive short bursts of the satellite data. This can limit the telemetry unit's usage of power to short intervals (e.g., during the short bursts of satellite data). The GPS can track the geographic location of the sensor buoy 1502 based on the GPS radio signals.

The compute device 1524c is disposed on a main board stacked below the component tray of the telemetry unit 1524. In some embodiments, the compute device 1524c and the telemetry unit 1524 are connected via a wired connection. In some embodiments, the compute device 1524c and the telemetry unit 1524 are connected via a wireless connection. The compute device 1524c may be functionally and/or structurally similar to the compute device 124 as described in reference to FIG. 1B and FIG. 1C and therefore is not described in further detail herein.

The humidity sensor 1524d may monitor the humidity within the controller housing 1521a to determine if a leak is present within the controller housing 1521a. In some embodiments, the humidity sensors 1524d may also be configured to detect humidity conditions outside of the controller housing 1521a.

The inertial measurement unit 1524e can include sensors that measure motion such as an accelerometer, gyroscope, magnetometer, and the like. While the positioning antenna 1524a aids in determining the global position of the sensor buoy 1502, the inertial measurement unit 1524e can provide information regarding the orientation and motion of the sensor buoy 1502. For example, the inertial measurement unit 1524e can provide information that may be used to determine a rotation rate, pitch angle, roll angle, yaw angle, buoyancy, and the like. In some embodiments, the measurements of the inertial measurement unit 1524e may be utilized to determine the water conditions (e.g., wave height, current speed, wave intensity, etc.). In some embodiments, the data collected by the inertial measurement unit 1524e may be used in combination with data from the positioning antenna 1524a to determine position and motion characteristics of the sensor buoy 1502.

The magnet switch 1528 is a switch (e.g., reed switch) that allows for the controller 1526 to be powered on without the need to open the controller housing 1521a. When the magnet switch 1528 detects a magnetic field, the magnet switch 1528 opens or closes a circuit that then indicates an action within the controller 1526. The action may include powering on and powering off the controller 1526 and/or may include affecting the operation of the controller 1526. For example, the action may include changing a setting within the controller 1526. The controller 1526 can be configured to monitor the magnet switch 1528 and detect changes to the configuration based on the presence of the external magnet.

Stacked below the compute device 1524c is a charging circuit 1522c. The charging circuit 1522c is configured to facilitate charging from the solar cells (e.g., solar cells 1522)

to either the components of the controller 1526 and/or the power supply. The charging circuit 1522*c* may throttle charging to prevent the power supply from being overloaded. In some embodiments, controller 1526 can be configured to control the power source. For example, controller 1526 can be configured to sequence power between the telemetry unit 1524, sensing module 1580, and the controller 1526 itself. Similarly stated, the controller 1526 can be configured to control the power source such that the power source provides power to the telemetry unit 1524, sensing module 1580, and the controller 1526 one at a time and/or in a predetermined sequence having little to no parallelization. This can prevent multiple components from drawing power from the power source at the same time, thereby eliminating and/or reducing power outages. In some embodiments, when the power is scarce (e.g., power source is running low, there is little to no sunlight, etc.), the controller 1526 can be configured to control the power source 1522*c* so as to prioritize operation of various components. For example, if the controller 1526 has already obtained sensor data, in the event of power scarcity, the controller 1526 can prioritize its own operation so that the sensor data is analyzed before additional sensor data is obtained.

Figure 18:
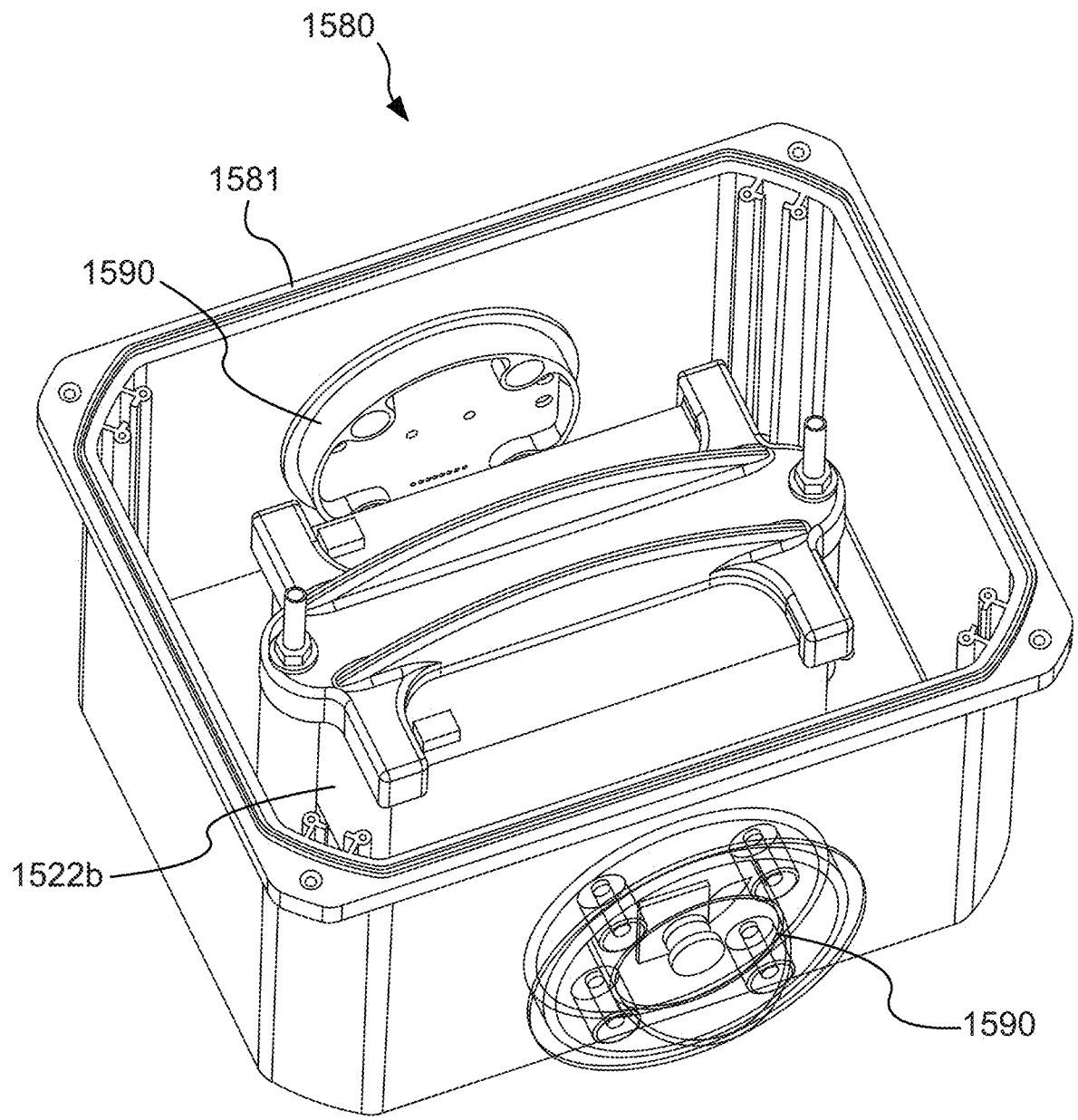
FIG. 18 is an illustration of a sensing module included in the sensor buoy of FIG. 15.

FIG. 18 is an illustration of the sensing module 1580 of the sensor buoy 1502. The components off the sensing module 1580 are configured to monitor the growth and development of the target product. The sensing module 1580 includes a waterproof enclosure 1581, a power source 1522*b*, and imaging systems 1590. In some embodiments, the sensing module 1580 may include additional components and/or sensors configured to monitor the growth and development of the target product and/or one or more environmental conditions, as described above. The waterproof enclosure 1581 is a container that prevents water from entering the sensing module 1580 and potentially damaging the components within. The waterproof enclosure 1581 may include a bottom portion and a top portion that may be selectively coupled to access the components within the sensing module 1580. The bottom portion and the top portion form a seal when they are coupled to prevent water from entering the sensing module 1580. In some embodiments, the waterproof enclosure 1581 may include apertures that allow for power and/or communication wiring to pass through. In some embodiments, the apertures may include features configured to water-tight wiring. In some embodiments, the shape of the waterproof enclosure 1581 corresponds to the number and desired location of the cameras.

The power source 1522*b* (e.g., structurally and/or functionally similar to the power source unit 122 of FIG. 1B) may be the main power source for the sensor buoy 1502 or may be a dedicated power source for the imaging systems 1590. The power source 1522*b* may be a battery, alternator, or any other device configured to store and distribute power. The power source 1522*b* may be electrically coupled to the imaging systems 1590 and/or other components of the sensor buoy 1502. For example, in some implementations, the power source 1522*b* can be one or more rechargeable batteries that can receive electric power from the power source (e.g., solar panels 1522) of the sensor buoy 1502.

The imaging systems 1590 are located opposite of one another on the waterproof enclosure 1581. In some embodiments, the sensing module 1580 may include additional or fewer imaging systems 1590. The imaging systems 1590 may include an optical sensor, a camera, a fluorometer, and/or any other device configured to monitor the target product.

Figure 19A:
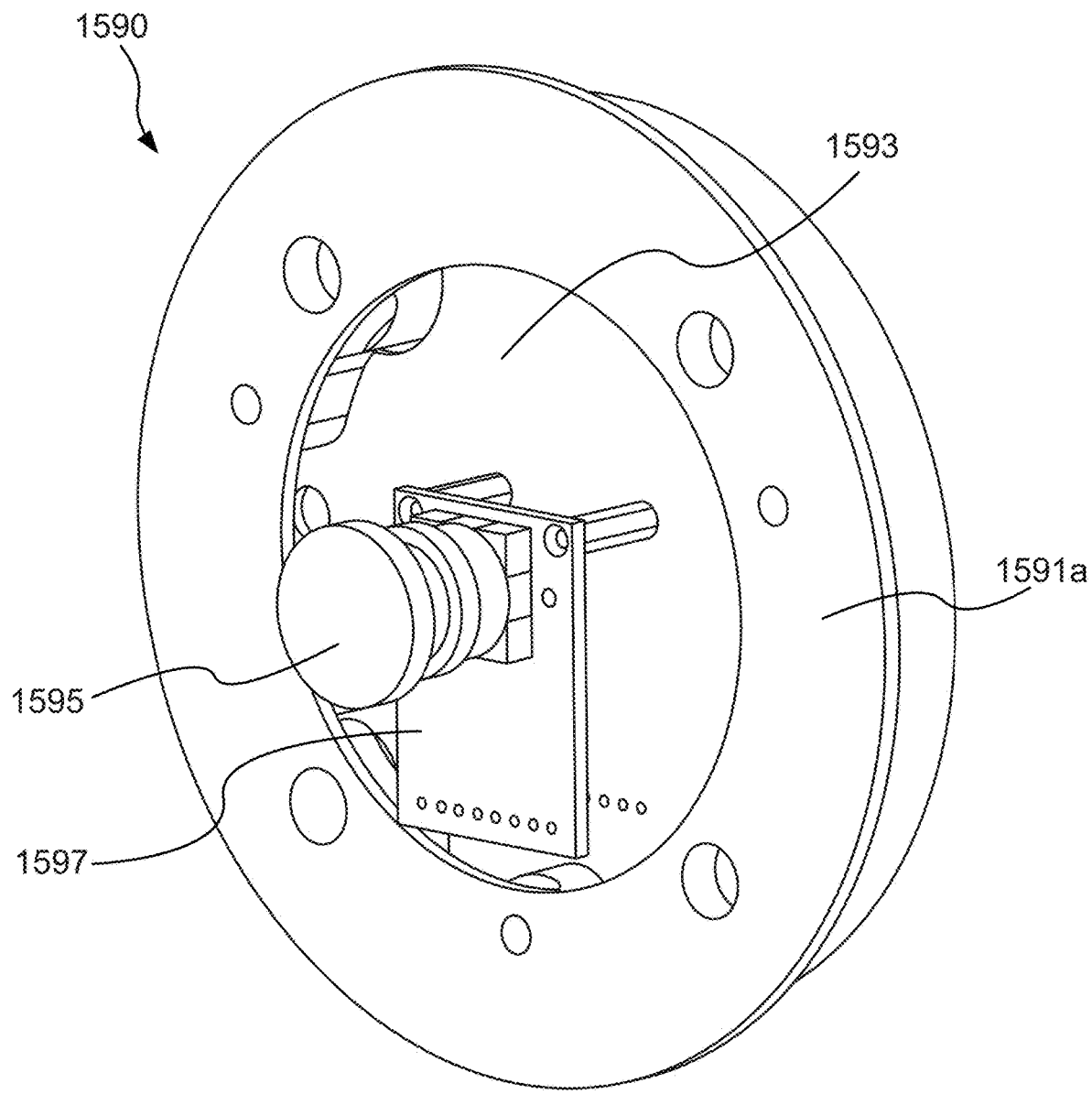
FIGS. 19A and 19B are a perspective view and a side view, respectively, of an imaging system included in the sensing module of FIG. 18, according to an embodiment.
Figure 19B:
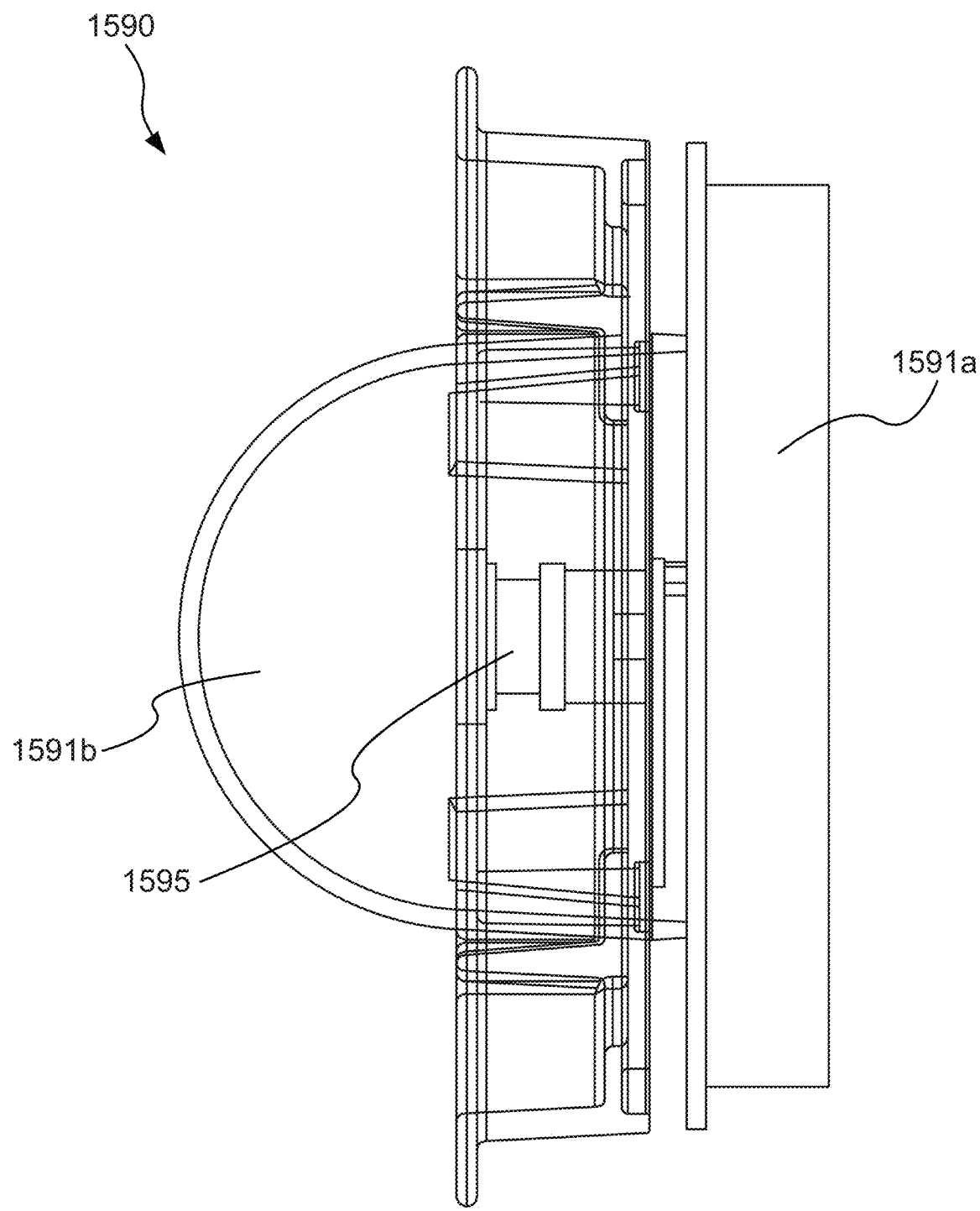

FIGS. 19A and 19B illustrate at least portions of the imaging system 1590 removed from the waterproof enclosure 1581 for clarity. The imaging system 1590 monitors the target product during deployment. The imaging system 1590 includes a housing interface 1591*a* coupled to an imaging board 1593. An imaging device 1595 is coupled to the imaging board 1593 via an interface 1597. A dome 1591*b* (not included in FIG. 19A) covers the imaging device 1595 and is coupled to the housing interface 1591*a*. In some embodiments, the imaging device 1595 is a camera, PAR sensor, fluorometer, and/or the like.

The housing interface 1591*a* serves as a frame for the imaging system 1590 and couples the imaging system 1590 to the waterproof enclosure 1581. The housing interface 1591*a* is configured to provide a waterproof seal between the imaging system 1590 and the waterproof enclosure 1581. In some embodiments, the housing interface 1591*a* may include additional features that aid in forming a seal with the waterproof enclosure 1581. For example, the housing interface 1591*a* may include a sealing ring, a rubber surface, or the like. In some embodiments, the housing interface 1591*a* may be sealed permanently (e.g., welded, adhered, etc.) to the waterproof enclosure 1581. The dome 1591*b* is as translucent dome that protects the imaging device 1595 without affecting the function of the imaging device 1595. The dome 1591*b* may be sealed (e.g., such that water may not enter) to the housing interface 1591*a* or may be integrally formed with the housing interface 1591*a*.

The imaging board 1593 is coupled to the housing interface 1519*a*. The imaging board 1593 provides circuitry for the function of the imaging device 1595. The imaging board 1593 may include at least one processor and at least one memory configured to at least operate the imaging device 1595. Additionally, the imaging board 1593 may include interface ports to communicatively couple the imaging device 1595, the interface 1597, and/or other components of the sensor buoy 1502. For example, the imaging board 1593 may communicatively couple to the controller 1526. The imaging board 1593 may be configured to receive (and/or process) the images captured by the imaging device 1595 or may send the captured images to another location (e.g., controller 1526) for processing. The imaging board 1593 is coupled to power source 1522*b* which provides electrical power for the operations of the imaging board 1593. In some embodiments, the imaging board 1593 distributes power to the imaging device 1595.

The imaging device 1595 is coupled to the imaging board 1593 via an interface 1597. In some embodiments, the interface 1597 may be a mechanical interface board (e.g., mounting plate, etc.) to provide the imaging device 1595 with a mounting point. In some embodiments, the interface 1597 may be an electronic interface. For example, the interface 1597 may be configured to directly control the functionality of the imaging device 1595. As another example, the interface 1597 may receive captured images from the imaging device 1595 and preprocess (e.g., format) the captured images such that they may be received by the camera board 1597.

The imaging device 1595 may be any type of image capturing device. In some embodiments, the imaging system 1590 1590 may include a light (e.g., LED) that may aid in the capturing images. The imaging device 1595 may capture images continuously (e.g., videos) or periodically (e.g., still images). In some embodiments, the imaging device 1595 may capture images in the visible light spectrum. In some embodiments, the imaging device 1595 may capture light outside of the visible light spectrum, such as ultraviolet light, infrared light, and the like. In some embodiments, the imaging system 1590 may include an antifouling device or mechanism such as the antifouling device 980 described above with reference to FIGS. 9-13. In such embodiments, the imaging system 1590 may include two LEDs—one for illumination that facilitates capturing images (e.g., for a camera, fluorometer, etc.) and one to limit and/or substantially prevent the buildup of biofilm or other material that may otherwise foul the dome 1591*b* or other surface of the imaging device 1595.

With the controller 1560 and sensing module 1580, as just described, the sensor buoy 1502 can be included in a deployment of carbon capture apparatuses and can be configured to monitor and/or collect data associated with the accumulation of target product biomass. In some implementations, data collected by the sensor buoy 1502 and associated with the status of the sensor buoy 1502 and/or the target product cultivated on or by the sensor buoy 1502 can be used, for example, as proxy data or the like to infer and/or predict an amount of target product accumulation on passive carbon capture apparatuses and/or substrates that do not include sensors and/or instrumentation. In addition, the sensor buoy 1502 can be used to collect environmental data that can be used to determine and/or predict characteristics associated with the deployment, as described, for example, in the '681 application. Accordingly, the data capture by the sensor buoy 1502 can be used to monitor the status of one or more portions of a deployment and/or can be used to determine, calculate, and/or predict an amount of biomass accumulated by the entire deployment and thus, an amount of carbon captured by the deployment.

Referring to FIGS. 20-22C, a sensor buoy 1602 including a first member 1620, a substrate containment area 1651, a sensing module 1680, and a scuttling device 1630 is shown, according to an embodiment. As described above with reference to the deployment 1401 shown in FIG. 14, the sensor buoy 1602 can be included in a deployment of a large number of passive carbon capture apparatuses (e.g., unpowered) that are configured to sink once a certain amount of target product is grown, while the sensor buoys 1602 (e.g., powered) are generally not configured to sink after target product is grown. For example, the sensor buoy 1602 may include instrumentation that monitors the target product growth. It may be desired to only sink the sensor buoy 1602 in specific situations when needed and not automatically as with the passive carbon capture apparatuses. For example, if the sensor buoy 1602 drifts off course (e.g., into a shipping lane or close to the shore), it may be favorable to sink the sensor buoy 1602 to limit and/or prevent damage and/or harm. As another example, the sensor buoy 1602 may accumulate algae and/or shellfish and may pose a risk to waters where the accumulated algae and/or shellfish are non-native. Including a scuttling device that may allow for remote sinking of the sensor buoy 1602 on demand may mitigate such risks.

The sensor buoy 1602 (e.g., structurally and/or functionally similar, at least in part, to the sensor buoy 1502 of FIG. 15) is configured to monitor growth of target product. The first member 1620 can be configured to at least temporarily provide the sensor buoy 1602 with positive buoyancy, allowing the sensor buoy 1602 to float on a surface of water. The substrate containment area 1651 may be configured to contain a substrate seeded with a target product. The sensing module(s) 1680 may be configured to monitor the growth of the target product within the substrate containment area 1651. In this manner, the first member 1620, the substrate containment area 1651, and the sensing module(s) 1680 can be structurally and/or functionally similar, at least in part, to the first member 1520, the substrate containment structures 1551, and/or the sensing module 1580 described above with reference to FIGS. 15-19. The sensor buoy 1602 also includes a power source unit (e.g., functionally and/or structurally similar to the power source unit 122 of FIG. 1B) which includes a solar cell 1622*a* and a storage device 122*b* (e.g., functionally and/or structurally similar to the solar cell 122*a* and the storage device 122*b*, respectively, of FIG. 1B). The power source unit may power the sensor buoy 1602 and/or the scuttling device 1630. In some embodiments, the scuttling device 1630 may include its own on-board power to provide redundancy.

The scuttling device 1630 is configured to selectively allow the sensor buoy 1602 to be scuttled (e.g., sunk). The scuttling device 1630 may communicate with a shore-based operator through existing satellite communications protocols. In some embodiments, the scuttling device 1630 may include its own on-board communication system. In some embodiments, the scuttling device 1630 may be communicably coupled to another communication system of the sensor buoy 1602 (e.g., included in a controller of the sensor buoy 1602 and/or the like). The scuttling device 1630 may activate (e.g., initiate sinking the sensor buoy 1602) when a command is received indicating that sinking is desired.

Figure 20:
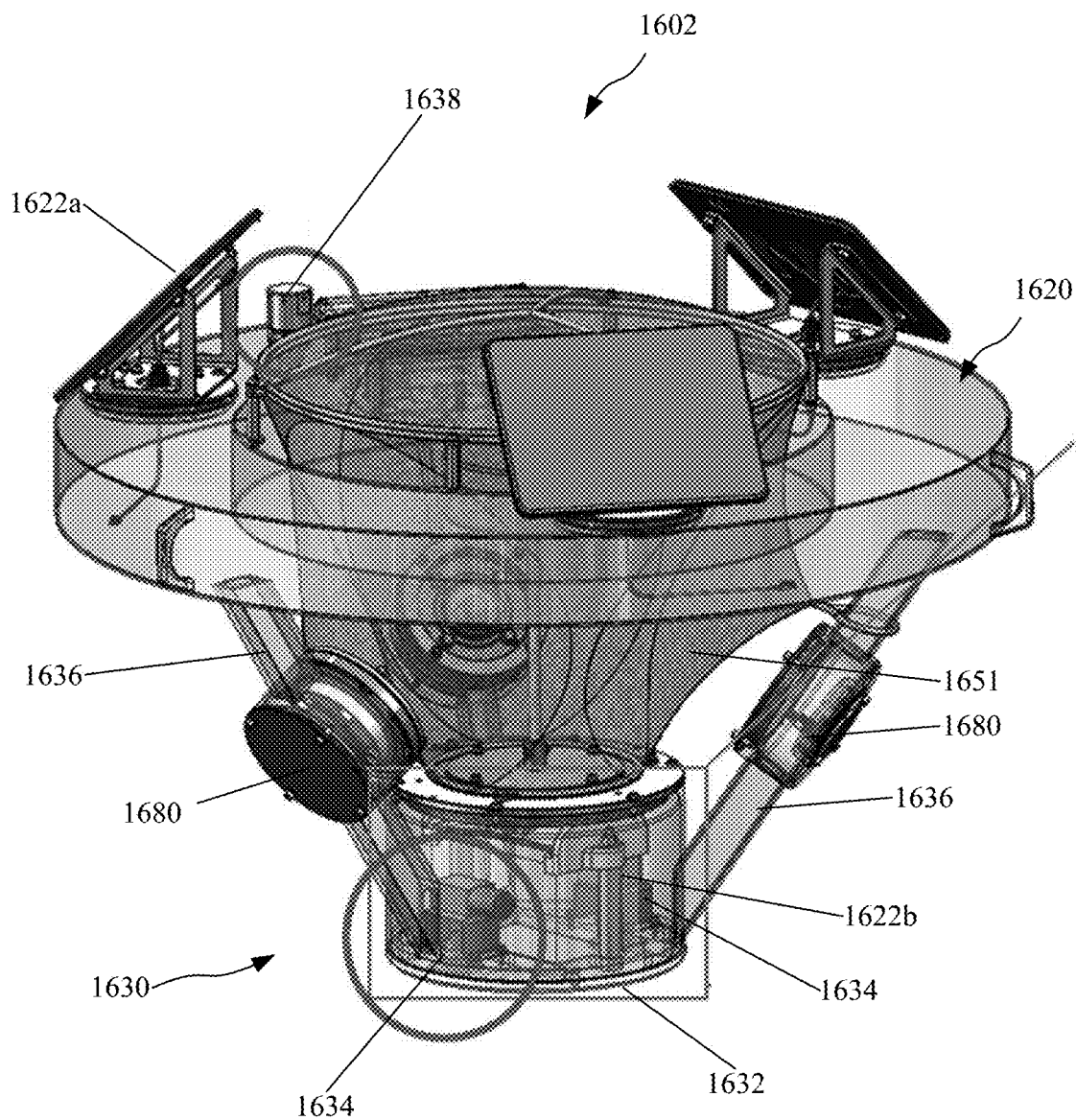
FIG. 20 is an illustration of a sensor buoy including a scuttling device, according to an embodiment.

As shown in FIG. 20, the scuttling device 1630 includes a scuttling chamber 1632, a set of connectors 1636 (e.g., arms, tubes, fluid conduits, and/or the like), and a valve 1638. The scuttling chamber 1632 includes one or more motor assemblies 1634. In some implementations, including more than one motor assembly 1634 provides redundancy as well as increases the flood rate (e.g., a rate at which the scuttling device 1630 fills with water). Each motor assembly 1634 is configured to open a valve in the scuttling device 1630 that allows for water to enter the scuttling chamber 1632, which in-turn decreases the buoyancy of the sensor buoy 1602, leading the sensor buoy 1602 to sink when no longer positively buoyant. The set of connectors 1636 are coupled between the scuttling chamber 1632 and the first member 1620. More specifically, the connectors 1636 can be substantially hollow and/or can otherwise define a flow path that fluidically couples the scuttling chamber 1632 to an inner volume of the first member 1620. As described in further detail herein, the valve 1638 can be coupled to the first member 1620 and in communication with the inner volume thereof. In some embodiments, the valve 1638 can be a one-way valve (e.g., a check valve or the like) that allows for air to flow out of the inner volume of the first member 1620 (e.g., in response to the scuttling chamber 1632 being flooded. In some embodiments, the scuttling chamber 1632 may include additional components for operating the scuttling device 1630 such as a power source, communication system, controller, and the like. In some embodiments, the scuttling device 1630 may include solar panels for powering the operations of the components of the scuttling device 1630.

Figure 21A:
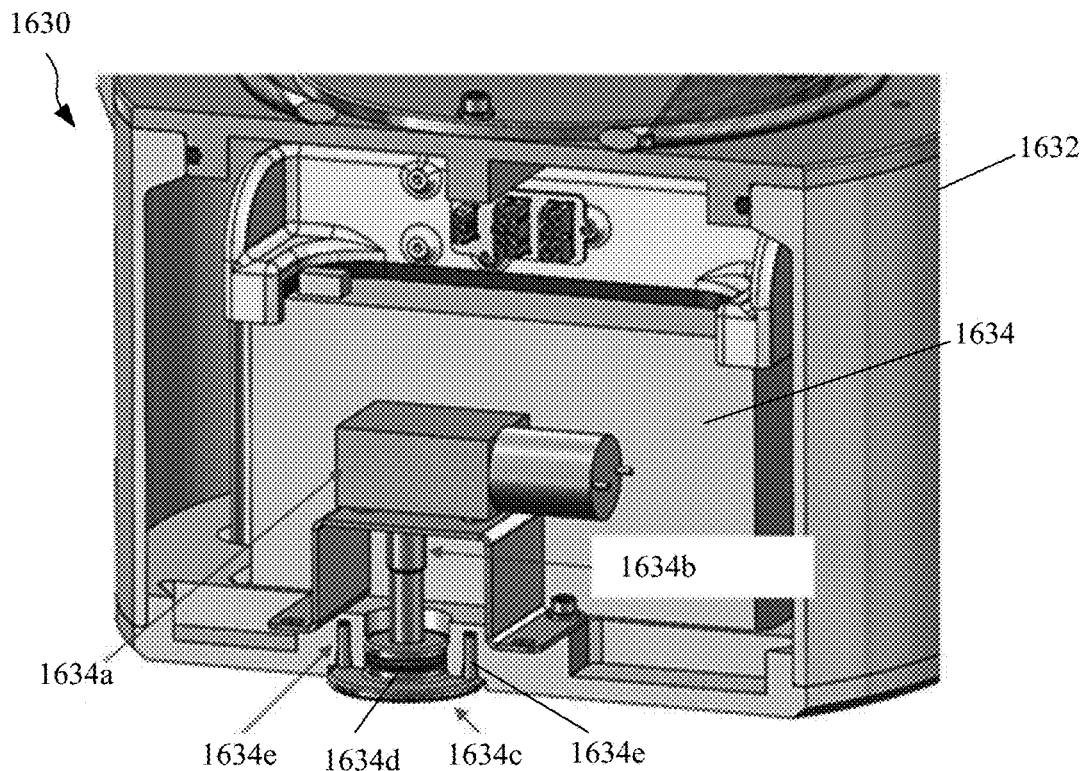
FIGS. 21A and 21B are various cross-sectional view of portions of the scuttling device included in the sensor buoy of FIG. 20.
Figure 21B:
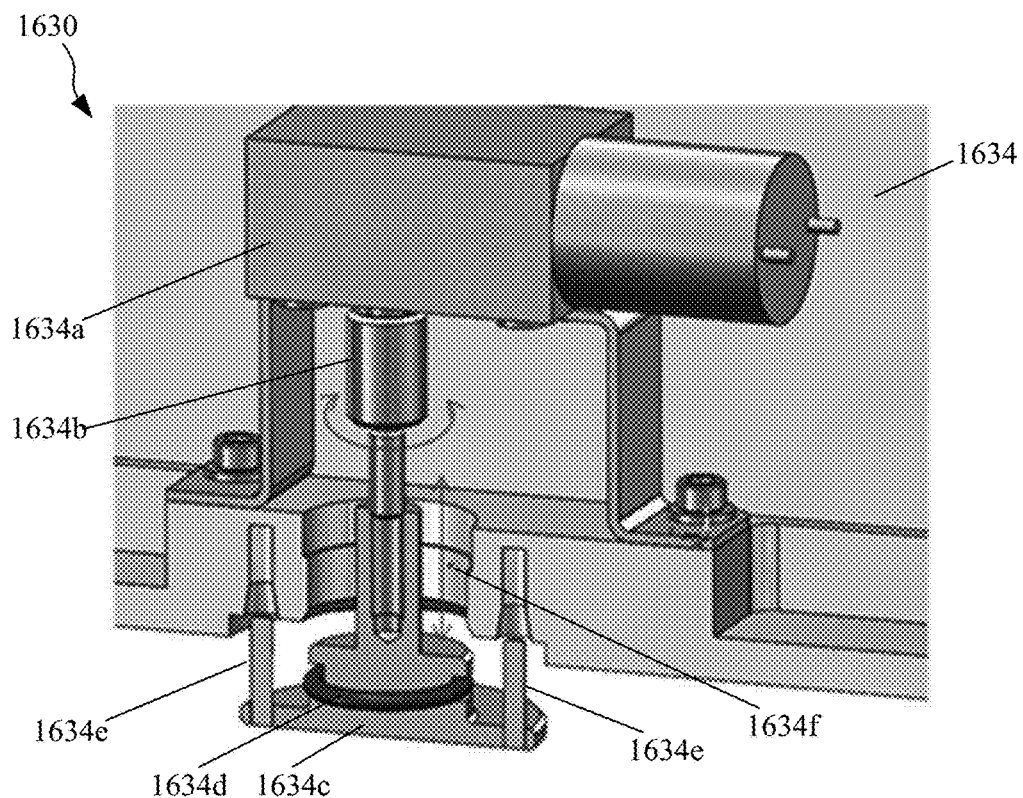

FIGS. 21A and 21B are cross-sectional views of the motor assembly 1634 of the scuttling device 1630 of FIG. 20. The motor assembly 1634 includes a scuttle motor 1634*a* coupled to a motor shaft 1634*b*. The motor shaft 1634*b* couples to a plug 1634*c* which includes a sealing ring 1634*d* and pins 1634*e*. The scuttle motor 1634*a* may be a DC motor configured to rotate the motor shaft 1634*b* when activated, which in turn, rotates the plug 1634*c* between a closed position (e.g., as seen in FIG. 21A), where water cannot enter the scuttling chamber 1632, and an open position (e.g., as seen in FIG. 21B), where water can enter the scuttling chamber 1632.

In some embodiments, the interface between the motor shaft 1634b and the plug 1634c can be a threaded interface. In such embodiments, the pins 1634e prevent the plug 1634c from rotating together with the motor shaft 1634b and allow for the plug 1634c to translate away from a sealing surface 1634f of the scuttling chamber 1632 when the motor shaft 1634b is activated, thus allowing for water to enter the scuttling chamber 1632. For example, when the plug 1634c is in a closed position, the sealing ring 1634d engages and/or contacts the sealing surface 1634f, forming a water-tight seal therebetween, as shown in FIG. 21A. When the plug 1634c is translated to the open position, the sealing ring 1634d is disengaged and/or otherwise not in contact with the sealing surface 1634f, thereby allowing water to flow into the scuttling chamber 1632.

Figure 22A:
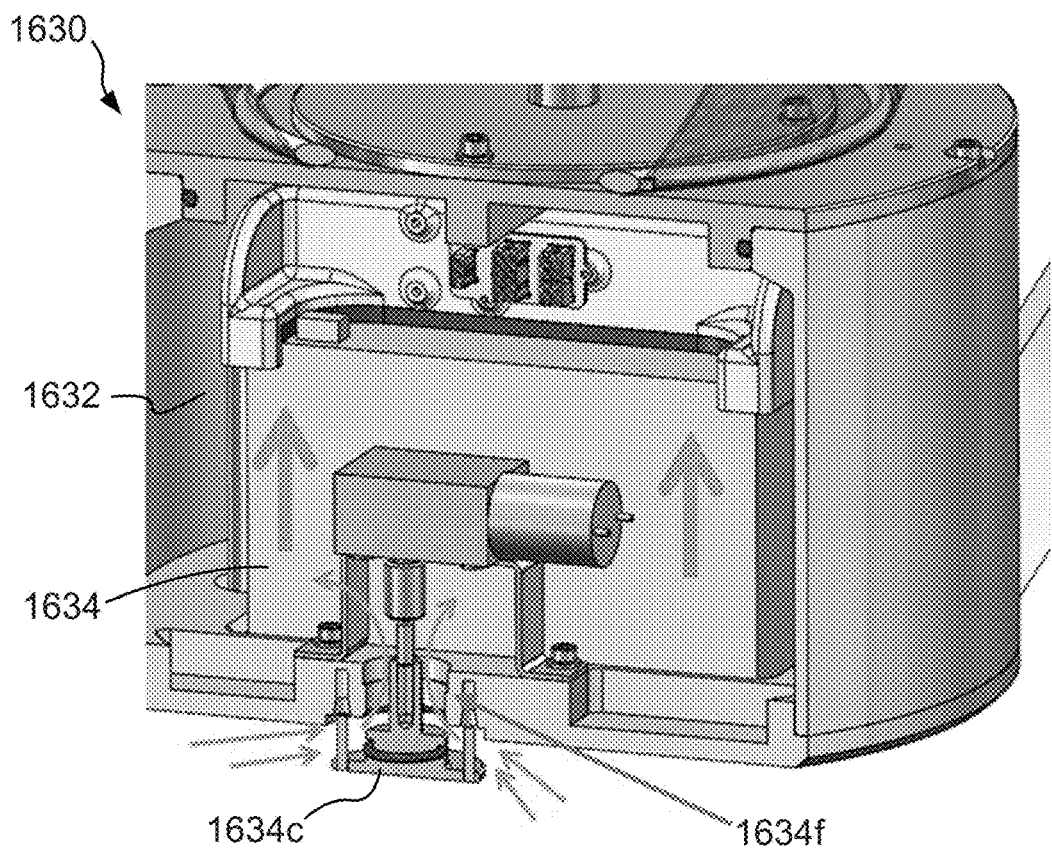
FIGS. 22A-22C are various cross-sections view of portions of the scuttling device of FIG. 20, illustrating the scuttling device in operation.
Figure 22B:
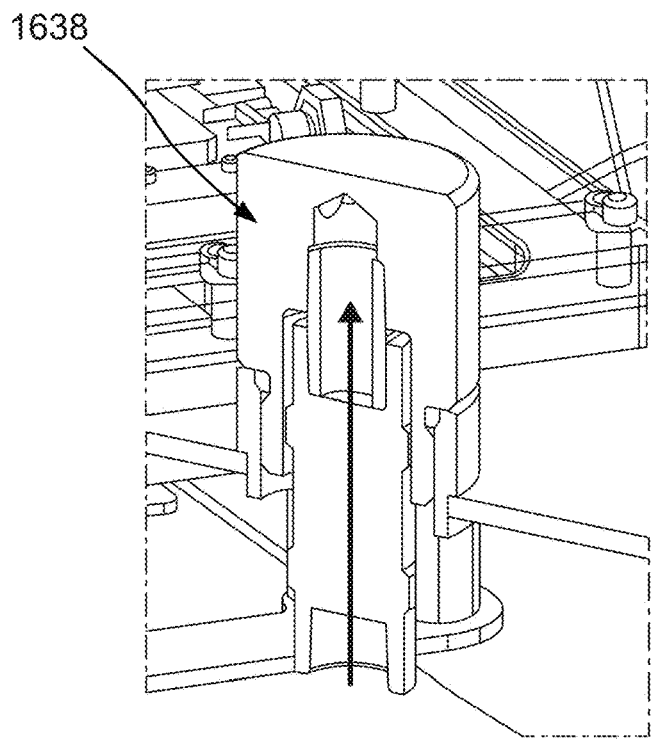
Figure 22C:
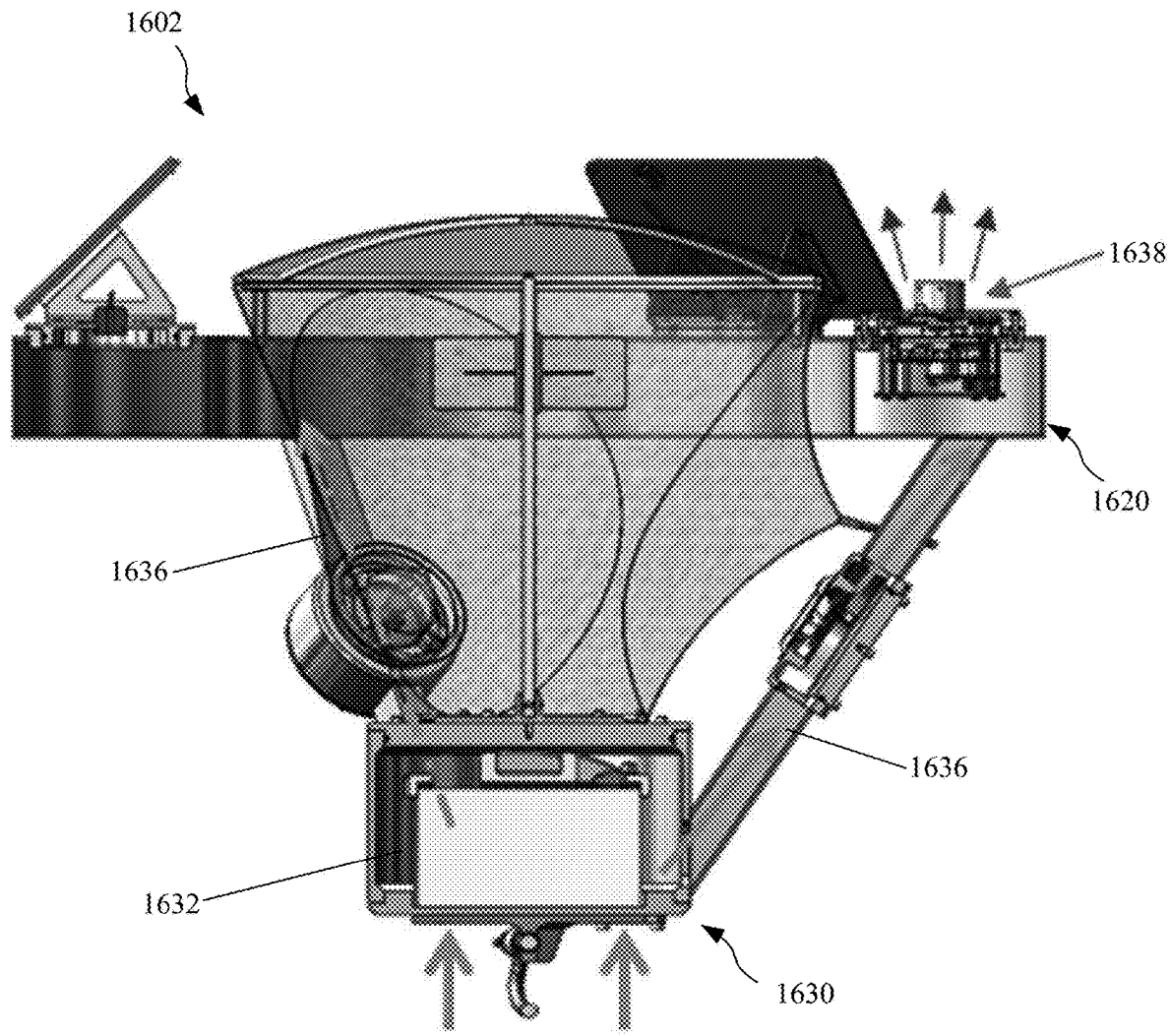

FIGS. 22A, 22B, and 22C are cross-sectional view of the scuttling device 1630 of FIG. 20 in operation (e.g., after being activated). FIG. 22A illustrates the plug 1634c in an open position after the motor assembly 1634 was activated, allowing water to enter the scuttling chamber 1632. In some instances, water can enter the scuttling chamber 1632 until the scuttling chamber 1632 is full. As water enters the scuttling chamber 1632, air or other gases are forced out of the scuttling chamber 1632. As seen in FIG. 22B, the valve 1638 coupled to the first member 1620 can be configured to allow air to leave the scuttling chamber 1632 as water displaces the air. More specifically, the inflow of water can force the air (or other gases) to flow into and/or through the connectors 1636 and into the inner volume of the first member 1620. In some implementations, the inflow of air into the inner volume of the first member 1620 increases an internal pressure to an extent sufficient to transition the valve 1638 from a closed state to an open state. As such, air can flow out of the sensor buoy 1602 via the valve 1638 as water is allowed to flow into the scuttling chamber 1632. In some embodiments, the scuttling device 1630 may include a motorized system that forces air out of the valve 1638 to increase the rate at which water flows into the scuttling chamber 1632. In some embodiments, the scuttling device 1630 may include multiple valves 1638 to provide redundancy and/or improve the flow rate. FIG. 22C illustrates a flow of water entering the scuttling chamber 1632. As water fills the scuttling chamber 1632, air leaves the scuttling chamber 1632 through the connectors 1636 and is expelled from the sensor buoy 1602 via the valve 1638. In some embodiments, water may continue up the connectors 1636 until the sensor buoy 1602 is filled with a sufficient volume of water to cause the sensor buoy 1602 to sink or otherwise lose positive buoyancy.

FIG. 23 is a flowchart illustrating a method 10 of monitoring ocean-based carbon dioxide removal devices and/or accumulation of a target product, according to an embodiment. The method 10 includes releasing a deployment including passive substrates seeded with a target product and a sensor buoy, at 11. In some embodiments, the deployment can be structurally and/or functionally similar to the deployment 1101, the passive substrates can be structurally and/or functionally similar to the carbon capture apparatus 1102A, and the sensor buoy can be structurally and/or functionally similar to the sensor buoys 1102, 1402, 1502, and/or 1602. In some embodiments, the deployment may include any number of passive substrates and sensor buoys. For example, the deployment may include a sensor buoy for every 1, 10, 100, 1,000, 10,000 passive substrates. In some embodiments, the sensor buoy may also be seeded with a target product or may include a containment area for growing a target product. The sensor buoy is configured to monitor various characteristics of the target product and/or the passive substrates. For example, the sensor buoy may monitor the growth and development of the target product. In some embodiments, the sensor buoy may monitor the location, direction, and other similar movement characteristics of the deployment as a whole. In some embodiments, sensor buoy may monitor the characteristics (e.g., temperature, currents, mineral content, etc.) of the body of water.

The method 10 includes obtaining sensor data associated with at least one characteristic of a target product of the sensor buoy, at 12. The characteristics of the target product may include growth rate, growth amount, nutrient usage, or other characteristics that may be utilized to determine carbon sequestration. In some embodiments, the sensor buoy may provide sensor data that requires processing to determine characteristics of a target product. For example, a computer vision tool may be utilized on sensor data received from an imaging device to determine an amount of target product growth. In some embodiments, the sensor data can be any suitable data captured and/or obtained by any of the sensing modules described herein.

The method 10 includes allowing the passive substrates and the target product thereon to sink as a result of the passive substrates transitioning from a positively buoyant state to a negatively buoyant state at 13. The passive substrates, after growing a sufficient amount of target product, become negatively buoyant and sink to the bottom of the body of water. For example, the passive substrates can be configured to become infiltrated with water over a given time such that when the target product has accumulated a desired amount of biomass, the passive substrate and the target product are negatively buoyant, allowing the passive substrate and the target product to sink. As described in detail herein, the sinking of the passive substrates moves carbon from the fast cycle to the slow cycle. The method 10 includes determining, based on the sensor data, an amount of biomass accumulation associated with the target product of the sensor buoy when the passive substrates transition to the negatively buoyant state, at 14. For example, the amount of biomass accumulation may be a direct measurement of the total target product or may be an estimate based on sensor data, calibration data, and/or any other suitable data. In some embodiments, the sensor buoy may monitor and collect data associated with a sample target product, which is then extrapolated and/or used to infer corresponding measurements for the passive substrates, thus providing an estimate of biomass accumulation of the passive substrate at the point of transition to negative buoyancy.

As described herein, the amount of biomass accumulation corresponds to the amount of carbon sequestration of the passive substrates included in the deployment. Thus the method 10 includes determining a carbon sequestration capacity associated with the target product of the passive substrates based at least in part on the amount of biomass accumulation associated with the target product of the sensor buoy, at 15. In some instances, the carbon sequestration capacity of a deployment can be valued and sold, for example, as a carbon credit on a carbon credit market.

In some implementations, the method 10 may optionally include retrieving the sensor buoy after allowing the passive substrates to sink. Retrieving the sensor buoy allows for the sensor buoy to be reused for additional passive substrates and reduces the risk of the sensor buoy damaging property and/or ecosystems as a result of drift. In other implementations, the method 10 may optionally include scuttling the sensor buoy. Scuttling the sensor buoy may include utilizing a scuttling device as described in reference to FIGS. 20-22B.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, an FPGA, an ASIC, and/or the like. Software modules (executed on hardware) can be expressed in a variety of software languages (e.g., computer code), including C, C++, Java™, Ruby, Visual Basic™, Python™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools, and/or combinations thereof (e.g., Python™). Additional examples of computer code include, but are not limited to, control signals, encrypted code, and compressed code.

While various embodiments have been particularly shown and described, it should be understood that they have been presented by way of example only, and not limitation. Various changes in form and/or detail may be made without departing from the spirit of the disclosure and/or without altering the function and/or advantages thereof unless expressly stated otherwise. Where schematics and/or embodiments described above indicate certain components arranged in certain orientations or positions, the arrangement of components may be modified.

Although various embodiments have been described as having particular features and/or combinations of components, other embodiments are possible having a combination of any features and/or components from any of embodiments described herein, except mutually exclusive combinations. The embodiments described herein can include various combinations and/or sub-combinations of the functions, components, and/or features of the different embodiments described.

The specific configurations of the various components can also be varied. For example, the size and specific shape of the various components can be different from the embodiments shown, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Where methods and/or events described above indicate certain events and/or procedures occurring in certain order, the ordering of certain events and/or procedures may be modified. Additionally, certain events and/or procedures may be performed concurrently in a parallel process, when possible, as well as performed sequentially as described above.

What is claimed:

1. A method, comprising:
   releasing a deployment of passive substrates into a portion of a body of water, the passive substrates being seeded with a target product, the deployment including a sensor buoy, the sensor buoy including a first member configured to at least temporarily maintain a positive buoyancy of the sensor buoy, a second member seeded with the target product, and a sensing module having a sensor oriented toward at least a portion of the second member;
   obtaining sensor data associated with at least one characteristic of the target product of the second member;
   allowing the passive substrates and the target product seeded thereon to sink as a result of the passive substrates transitioning from a positively buoyant state to a negatively buoyant state;
   determining, based at least in part on the sensor data, an amount of biomass accumulation associated with the target product of the second member when the passive substrates transition to the negatively buoyant state; and
   determining a carbon sequestration capacity associated with the target product of the passive substrates based at least in part on the amount of biomass accumulation associated with the target product of the second member.

2. The method of claim 1, further comprising:
   retrieving the sensor buoy after allowing the passive substrates to sink.

3. The method of claim 1, wherein the sensor buoy includes a scuttling device, the scuttling device includes a chamber that defines an inner volume in communication with an inner volume of the first member, a plug movably coupled to the chamber, and a motor disposed in the inner volume of the chamber, the method further comprising:
   moving the plug, via the motor, from a closed state in which the chamber is sealed allowing the first member to maintain the positive buoyancy of the sensor buoy to an open state in which the plug allows a flow of water into the inner volume of the chamber.

4. The method of claim 3, wherein the first member includes a one way valve in communication with the inner volume of the first member, the method further comprising:

transitioning the one way valve from a closed state to an open state in response to the flow of water into the inner volume of the chamber;

allowing air to flow out of the inner volume of the first member while the one way valve is in the open state until the sensor buoy becomes negatively buoyant; and allowing the sensor buoy to sink as a result of becoming negatively buoyant.

5. The method of claim 3, further comprising:
remotely actuating the motor to move the plug from the closed state to the open state.

6. The method of claim 1, wherein each passive substrate from the plurality of passive substrates is formed from natural materials.

7. The method of claim 1, wherein each passive substrate from the plurality of passive substrates is formed at least in part from wood.

8. The method of claim 1, wherein the sensor includes at least an image capturing device, the sensor data associated with at least one characteristic of the target product of the second member includes imaging data of the target product of the second member captured by the image capturing device.

9. The method of claim 1, wherein the passive substrates are configured to transition from the positively buoyant state to the negatively buoyant state after a period of time of the target product accumulating biomass.

10. The method of claim 1, further comprising:
obtaining, at the sensor buoy, data associated with at least one environmental characteristic of the portion of the body of water in which the deployment is deployed, and wherein the determining the amount of biomass accumulation includes determining the amount of biomass accumulation based on the sensor data and the data associated with the at least one environmental characteristic.

\* \* \* \* \*